US009987348B2

(12) United States Patent
Nitzel et al.

(10) Patent No.: US 9,987,348 B2
(45) Date of Patent: Jun. 5, 2018

(54) PCV2B DIVERGENT VACCINE COMPOSITION AND METHODS OF USE

(71) Applicant: Zoetis Services LLC, Florham Park, NJ (US)

(72) Inventors: Gregory Paul Nitzel, Paw Paw, MI (US); David Ewell Slade, Portage, MI (US)

(73) Assignee: Zoetis Services LLC, Parsippany, NJ (US)

( * ) Notice: Subject to any disclaimer, the term of this patent is extended or adjusted under 35 U.S.C. 154(b) by 27 days.

(21) Appl. No.: 14/917,620

(22) PCT Filed: Sep. 24, 2014

(86) PCT No.: PCT/US2014/057190
§ 371 (c)(1),
(2) Date: Mar. 9, 2016

(87) PCT Pub. No.: WO2015/048115
PCT Pub. Date: Apr. 2, 2015

(65) Prior Publication Data
US 2016/0220658 A1    Aug. 4, 2016

Related U.S. Application Data

(60) Provisional application No. 61/882,289, filed on Sep. 25, 2013.

(51) Int. Cl.
*A61K 39/12* (2006.01)
*A61K 45/06* (2006.01)
*A61K 39/39* (2006.01)
*C12N 7/00* (2006.01)
*A61K 39/00* (2006.01)

(52) U.S. Cl.
CPC ............. *A61K 39/12* (2013.01); *A61K 39/39* (2013.01); *A61K 45/06* (2013.01); *C12N 7/00* (2013.01); *A61K 2039/5252* (2013.01); *A61K 2039/54* (2013.01); *A61K 2039/545* (2013.01); *A61K 2039/552* (2013.01); *A61K 2039/55505* (2013.01); *A61K 2039/55511* (2013.01); *A61K 2039/55566* (2013.01); *A61K 2039/58* (2013.01); *C12N 2710/14043* (2013.01); *C12N 2710/24043* (2013.01); *C12N 2750/10022* (2013.01); *C12N 2750/10034* (2013.01); *C12N 2750/10071* (2013.01)

(58) Field of Classification Search
None
See application file for complete search history.

(56) References Cited

U.S. PATENT DOCUMENTS

| 4,708,871 A | 11/1987 | Geysen et al. |
| 4,745,051 A | 5/1988 | Smith et al. |
| 4,824,785 A | 4/1989 | Acree et al. |
| 4,946,787 A | 8/1990 | Eppstein et al. |
| 5,106,733 A | 4/1992 | Baker et al. |
| 5,147,966 A | 9/1992 | St. Clair et al. |
| 5,238,662 A | 8/1993 | Dubrovsky |
| 5,322,774 A | 6/1994 | Peakman et al. |
| 5,382,425 A | 1/1995 | Cochran et al. |
| 5,436,001 A | 7/1995 | Kramer |
| 5,459,127 A | 10/1995 | Felgner et al. |
| 5,498,413 A | 3/1996 | Casel Alvarez et al. |
| 5,545,412 A | 8/1996 | Eppstein et al. |
| 5,565,205 A | 10/1996 | Petersen |
| 5,580,557 A | 12/1996 | Kramer |
| 5,580,859 A | 12/1996 | Felgner et al. |
| 5,587,164 A | 12/1996 | Sanderson et al. |
| 5,703,055 A | 12/1997 | Felgner et al. |
| 5,705,385 A | 1/1998 | Bally et al. |
| 5,719,131 A | 2/1998 | Harris et al. |
| 5,733,555 A | 3/1998 | Chu |
| 5,756,103 A | 5/1998 | Paoletti et al. |
| 5,770,212 A | 6/1998 | Falkner et al. |
| 5,795,872 A | 8/1998 | Ricigliano et al. |
| 5,800,992 A | 9/1998 | Fodor et al. |
| 5,811,103 A | 9/1998 | Meyers et al. |
| 5,820,869 A | 10/1998 | Wasmoen et al. |
| 5,833,975 A | 11/1998 | Paoletti et al. |
| 5,885,823 A | 3/1999 | Knittel et al. |
| 5,888,513 A | 3/1999 | Plana Duran et al. |
| 5,910,488 A | 6/1999 | Nabel et al. |
| 5,925,359 A | 7/1999 | Van Woensel et al. |

(Continued)

FOREIGN PATENT DOCUMENTS

| CN | 102296089 A | 12/2011 |
| CN | 103122352 A | 5/2013 |

(Continued)

OTHER PUBLICATIONS

US 7,351,579, 04/2008, Jestin et al. (withdrawn)
US 7,622,126, 11/2009, Jestin et al. (withdrawn)
US 7,625,568, 12/2009, Jestin et al. (withdrawn)
Turcitu et al. (Research in Veterinary Science. 2011; 91: e103-e106).*
Sequence alignment of SEQ ID No. 1 with Geneseq database access No. F8V1X0_PCV2 by Turcitu et al in Res Vet Sci vol. 91 pp. E103-E106 Sep. 2011.*

(Continued)

*Primary Examiner* — Shanon A. Foley
(74) *Attorney, Agent, or Firm* — Gloria K. Szakiel

(57) ABSTRACT

This invention provides a vaccine composition for protecting pigs against PCV2, including a highly virulent *porcine circovirus* type 2b (PCV2b) divergent strain, the composition including a PCV2b divergent ORF2 polypeptide, wherein the ORF2 polypeptide comprises Leucine (L) at position 89, Threonine (T) at position 90, and Aspargine (N) at position 134, according to the numbering of SEQ ID NO: 1 herein.

28 Claims, 7 Drawing Sheets

(56) References Cited

U.S. PATENT DOCUMENTS

| | | |
|---|---|---|
| 5,968,525 A | 10/1999 | Fitzgerald et al. |
| 5,990,091 A | 11/1999 | Tartaglia et al. |
| 6,004,777 A | 12/1999 | Tartaglia et al. |
| 6,015,694 A | 1/2000 | Dubensky, Jr. et al. |
| 6,019,980 A | 2/2000 | Li et al. |
| 6,033,904 A | 3/2000 | Cochran et al. |
| 6,143,734 A | 11/2000 | Garvey et al. |
| 6,165,493 A | 12/2000 | Neurath et al. |
| 6,165,995 A | 12/2000 | Hilgers |
| 6,207,165 B1 | 3/2001 | Audonnet et al. |
| 6,217,883 B1 | 4/2001 | Allan et al. |
| 6,287,856 B1 | 9/2001 | Poet et al. |
| 6,294,176 B1 | 9/2001 | Cochran et al. |
| 6,368,601 B1 | 4/2002 | Allan et al. |
| 6,391,314 B1 | 5/2002 | Allan et al. |
| 6,475,779 B2 | 11/2002 | Mathiowitz et al. |
| 6,497,883 B1 | 12/2002 | Bublot et al. |
| 6,517,843 B1 | 2/2003 | Ellis et al. |
| 6,573,081 B2 | 6/2003 | Bernhardt et al. |
| 6,610,310 B2 | 8/2003 | Hilgers |
| 6,660,272 B2 | 12/2003 | Allan et al. |
| 6,703,023 B1 | 3/2004 | Jestin et al. |
| 6,794,163 B2 | 9/2004 | Liu et al. |
| 6,943,152 B1 | 9/2005 | Audonnet et al. |
| 6,953,581 B2 | 10/2005 | Allan et al. |
| 7,109,025 B1 | 9/2006 | Eloit et al. |
| 7,122,192 B2 | 10/2006 | Allan et al. |
| 7,144,698 B2 | 12/2006 | Wang et al. |
| 7,148,015 B2 | 12/2006 | Jestin et al. |
| 7,179,472 B2 | 2/2007 | Jestin et al. |
| 7,192,594 B2 | 3/2007 | Haines et al. |
| 7,223,407 B2 | 5/2007 | Jestin et al. |
| 7,223,594 B2 | 5/2007 | Jestin et al. |
| 7,244,433 B2 | 7/2007 | Jestin et al. |
| 7,258,865 B2 | 8/2007 | Jestin et al. |
| 7,261,898 B2 | 8/2007 | Jestin et al. |
| 7,276,353 B2 | 10/2007 | Meng |
| 7,279,166 B2 | 10/2007 | Meng et al. |
| 7,297,537 B2 | 11/2007 | Jestin et al. |
| 7,312,065 B2 | 12/2007 | Roof et al. |
| 7,314,628 B2 | 1/2008 | Jestin et al. |
| 7,323,330 B2 | 1/2008 | Jestin et al. |
| 7,368,117 B2 | 5/2008 | Fetzer et al. |
| 7,390,494 B2 | 6/2008 | Jestin et al. |
| 7,405,075 B2 | 7/2008 | Jestin et al. |
| 7,407,803 B2 | 8/2008 | Jestin et al. |
| 7,425,444 B2 | 9/2008 | Jestin et al. |
| 7,575,752 B2 | 8/2009 | Meng et al. |
| 7,604,808 B2 | 10/2009 | Jestin et al. |
| 7,722,883 B2 | 5/2010 | Jestin et al. |
| 7,740,865 B2 | 6/2010 | Jestin et al. |
| 7,740,866 B2 | 6/2010 | Jestin et al. |
| 7,741,026 B2 | 6/2010 | Jestin et al. |
| 7,758,865 B2 | 7/2010 | Jestin et al. |
| 7,758,870 B2 | 7/2010 | Roof et al. |
| 7,829,273 B2 | 11/2010 | Roof et al. |
| 7,838,213 B2 | 11/2010 | Roof et al. |
| 7,838,214 B2 | 11/2010 | Roof et al. |
| 7,951,907 B2 | 5/2011 | Jestin et al. |
| 7,959,927 B2 | 6/2011 | Chu et al. |
| 7,968,285 B2 | 6/2011 | Roof et al. |
| 8,058,048 B2 | 11/2011 | Meng et al. |
| 8,124,723 B2 | 2/2012 | Jestin et al. |
| 8,415,525 B2 | 4/2013 | Jestin et al. |
| 8,715,690 B2 | 5/2014 | Jestin et al. |
| 8,916,353 B2 | 12/2014 | Jestin et al. |
| 9,011,868 B2 | 4/2015 | Roof et al. |
| 9,211,324 B2 | 12/2015 | Meng et al. |
| 2002/0055189 A1 | 5/2002 | Bernhardt et al. |
| 2002/0106639 A1 | 8/2002 | Wang et al. |
| 2002/0177216 A1 | 11/2002 | Liu et al. |
| 2003/0170616 A1 | 11/2003 | Wang et al. |
| 2003/0215455 A1 | 11/2003 | Reynolds et al. |
| 2005/0058653 A1 | 3/2005 | Ellis et al. |
| 2006/0246425 A1 | 11/2006 | Allibert et al. |
| 2006/0286123 A1 | 12/2006 | Fetzer et al. |
| 2008/0181910 A1 | 7/2008 | Roof et al. |
| 2008/0226669 A1* | 9/2008 | Roof ............... A61K 39/04 424/201.1 |
| 2008/0267995 A1 | 10/2008 | Roof et al. |
| 2008/0279889 A1 | 11/2008 | Roof et al. |
| 2009/0017064 A1 | 1/2009 | Wu et al. |
| 2009/0042245 A1 | 2/2009 | Elchmeyer et al. |
| 2009/0162398 A1 | 6/2009 | Wu |
| 2011/0091499 A1* | 4/2011 | Fachinger ........... A61K 39/12 424/204.1 |
| 2011/0305725 A1 | 12/2011 | Wu |
| 2015/0056248 A1 | 2/2015 | Haiwick et al. |
| 2015/0175668 A1 | 6/2015 | Jestin et al. |
| 2015/0182616 A1 | 7/2015 | Jestin et al. |
| 2016/0220658 A1* | 8/2016 | Nitzel ............... A61K 39/12 |

FOREIGN PATENT DOCUMENTS

| | | |
|---|---|---|
| CN | 102296089 B | 9/2013 |
| CN | 103122352 B | 2/2015 |
| DE | 10044648 | 3/2002 |
| EP | 0 737 750 | 10/1996 |
| EP | 1 386 617 | 3/2008 |
| EP | 1 036 180 B1 | 10/2008 |
| FR | 2 422 956 | 11/1979 |
| FR | 2 518 755 | 6/1983 |
| FR | 2769321 | 10/1997 |
| FR | 9715396 | 12/1997 |
| FR | 2769322 | 4/1999 |
| FR | 2772047 | 6/1999 |
| SU | 1 538 305 | 12/1994 |
| WO | WO 89/06972 | 8/1989 |
| WO | WO 90/07935 | 7/1990 |
| WO | WO 90/11092 | 10/1990 |
| WO | WO 91/18627 | 12/1991 |
| WO | WO 92/03157 | 3/1992 |
| WO | WO 92/05255 | 4/1992 |
| WO | WO 93/16726 | 9/1993 |
| WO | WO 94/01133 | 1/1994 |
| WO | WO 94/21797 | 9/1994 |
| WO | WO 94/27238 | 11/1994 |
| WO | WO 94/27435 | 12/1994 |
| WO | WO 95/11307 | 4/1995 |
| WO | WO 95/30437 | 11/1995 |
| WO | WO 96/34109 | 10/1996 |
| WO | WO 96/40931 | 12/1996 |
| WO | WO 96/40945 | 12/1996 |
| WO | WO 98/40499 | 9/1998 |
| WO | WO 99/18214 | 4/1999 |
| WO | WO 99/29717 | 6/1999 |
| WO | WO 99/29871 | 6/1999 |
| WO | WO 99/45956 | 9/1999 |
| WO | WO 00/01409 | 1/2000 |
| WO | WO 00/24428 | 5/2000 |
| WO | WO 00/47756 | 8/2000 |
| WO | WO 00/77188 | 12/2000 |
| WO | WO 00/77216 | 12/2000 |
| WO | WO 01/016330 A3 | 3/2001 |
| WO | WO 01/017556 A1 | 3/2001 |
| WO | WO 01/017750 A2 | 3/2001 |
| WO | WO 01/017751 A2 | 3/2001 |
| WO | WO 01/96377 | 6/2002 |
| WO | WO 02/102999 | 12/2002 |
| WO | WO 06/072065 | 11/2006 |
| WO | 2010061000 A1 | 6/2010 |
| WO | WO 2011/116094 A2 | 9/2011 |
| WO | 2015/026912 A1 | 2/2015 |

OTHER PUBLICATIONS

Trible et al. ("Protective Immunity vs. Immunopathogenesis: Recognition of the Structural form of the PCV2 Capsid Determines the Outcome." (2013)).*

Song et al. (Clinical and experimental vaccine research. 2015; 4 (2): 166-176).*

Grau-Roma et al. (Veterinary Journal. 2011; 187: 23-32).*

(56) References Cited

OTHER PUBLICATIONS

Sequence alignment of SEQ ID No. 1 with Geneseq database access No. AZR61798 by Bian et al in CN102296089 on Apr. 2011.*
Sequence alignment of instant SEQ ID No. 66 with GenEmbl database access No. FJ948168 by Yin et al on 2010 in Journal of Virology.*
U.S. Appl. No. 60/069,233, filed Dec. 11, 1997, Wang et al.
U.S. Appl. No. 60/069,750, filed Dec. 16, 1997, Wang et al.
Adams, Mark D. et al. "Complementary DNA Sequencing: Expressed Sequence Tags and Human Genome Project," *Science*, 1651-1656. (1991).
Albina et al., "Premiers résultats du CNEVA sur le dépérissement fatal du porcelet en fin de post-sevrage" *La Semaine Veterinaire des Filieres*, 26:1-2, Nov. 30, 1996.
Albina et al., "*An Experimental Model for Post-weaning Multisystemic Wasting Syndrome (PMWS) in Growing Piglets*," 125 J. Comp. Path 292-303 (2001).
Allan et al., "Porcine Circoviruses: A Review," *J Vet Diagn Invest*. 12: 3-14 (2000).
Allan et al., "Immunostimulation, PCV-2 and PMWS," *Veterinary Record* (2000); 147(6):170-171.
Allan, G.M., et al., "Production, preliminary characterisation and applications of monoclonal antibodies to porcine circovirus," *Veterinary Immunology and Immunopathology*, 43 (1994) 357-371.
Allan, G.M. et al., "Pathogenesis of porcine circovirus; experimental infections of colostrum deprived piglets and examination of pig fetal material," *Vet. Microbiol*., (1995) 44: 49-64.
Allan, G. M. et al., "Isolation of Porcine Circovirus-like Viruses from Pigs with a Wasting Disease in the USA and Europe", *Journal of Veterinary Diagnostic Investigation*, vol. 10, pp. 3-10, Jan. 1998, XP 002068503.
Allan et al., "Experimental infection of colostrum deprived piglets with porcine circovirus 2 (PCV2) and porcine reproductive and respiratory syndrome virus (PRRSV) potentiates PCV2 replication", 145 Arch. Virol. 2421-2429 (2002).
Allan, G. et al., "Islolation and Characterisation of Circoviruses From Pigs With Wasting Syndromes in Spain, Denmark and Northern Ireland," 66 Vet. Microbiology 115-123 (1999).
Allan, G. et al., "Novel Porcine Circoviruses From Pigs With Wasting Disease Syndrome," 142(17) Veterinary Record 467-468 (Apr. 25, 1998).
Altmann, Curtis R. et al. "Microarray-Based Analysis of Early Development in Xenopus laevis," *Developmental Biology*, 236:64-75 (2001).
Author Unknown, GenBank info on AF027217 (Revised Jul. 5, 2002).
Bantle, John A. et al. "Phase III Interlaboratory Study of FETAX Part 3. FETAX Validation using 12 Compounds with and without an Exogenous Metabolic Activation System," *Journal of Applied Toxicology*, 19:447-472 (1999).
Barany, F., *PNAS. USA*, (1991) 88: 189-193.
Bassami, M.R., et al., "Psittacine Beak and Feather Disease Virus Nucleotide Sequence Analysis and Its Relationship to Porcine Circovirus, Plant Circoviruses, and Chicken Anaemia Virus", 1998, Virology, vol. 249, pp. 453-459.
Beach, N. et al. "Novel chimeric porcine circovirus (PCV) with the capsid gene of the emerging PCV2b subtype cloned in the genomic backbone of the non-pathogenic PCV1 is attenuated in vivo and induces protective and cross-protective immunity against PCV2b and PCV2a subtypes in pigs," Vaccine 29 (2011) pp. 221-232.
Behr, J.P., "Gene Transfer with Synthetic Cationic Amphiphiles: Prospects for Gene Therapy" *Bioconjugate Chem*. 5(5):382-389 (1994).
Bei, R. et al., "The Use of a Cationic Liposome Formulation (DOTAP) Mixed with a Recombinant Tumor-Associated Antigen to Induce Immune Responses and Protective Immunity in Mice," *Journal of Immunotherapy*, 21(3):159-169 (1998).
Blanchard et al., "An ORF2 Protein-Based ELISA for Procine Circovirus Type 2 Antibodies in Post-Weaning Multisystemic Wasting Syndrome", *Veterinary Microbiology*, (2003) 94:183-184.

Blanchard et al., "Protection of Swine Against Post-Weaning Multisystemic Wasting Syndrome (PMWS) by Porcine Circovirus Type 2 (PCV2) Proteins", *Vaccine* (2003) 21:4565-4575.
Bolin et al., "*Postweaning multisystemic wasting syndrome induced after experimental inoculation of cesarean-derived, colostrum-deprived piglets with type 2 porcine circovirus*," 13 J. Vet. Diagn. Invest. 185-194 (2001).
Bowie et al., "*Deciphering the Message in Protein Sequences: Tolerance to Amino Acid Substitutions*," 247 Science 1306-1310 (1990).
Buckholz, R.G., "Yeast systems for the expression of heterologous gene products." *Curr. Op. Biotechnology* (1993) 4:538-542.
Buhk, H.J. et al., "Cloning and Sequencing of the Porcine Circovirus (PCV) Genome," Series A 260(4) Zentralblatt fur Bakteriologie Mikrobiologie and Hygiene 465 (Dec. 1985).
Burg, J.L. et al., "Single molecule detection of RNA reporter probes by amplification with QB replicase," *Mol. and Cell. Probes*, (1996) 10: 257-271.
Cheung, A. K. et al., "Detection of two porcine circovirus type 2 genotypic groups in United States swine herds," Arch Virol (2007) 152: pp. 1035-1044.
Chianini, F. et al. "Immunohistochemical characterisation of PCV2 associate lesions in lymphoid and non-lymphoid tissues of pigs with natural postweaning multisystemic wasting syndrome (PMWS)," Veterinary Immunology and Immunopathology, vol. 94 (2003), pp. 63-75.
Cho et al., "Enhanced cellular immunity of hepatitis C virus nonstructural proteins by codelivery of granulocyte macrophage-colony stimulating factor gene in intramuscular DNA immunization," *Vaccine* 17:1136-1144 (1999).
Choi, Jiwon et al., "Sequence analysis of old and new strains of porcine circovirus associated with congenital tremors in pigs and their comparison with strains involved with postweaning multisystemic wasting syndrome," the Canadian Journal of Veterinary Research, 2002; 66:217-224.
Chu, B.C.F. et al., "Synthesis of an amplifiable reporter RNA for bioassays," *NAR*, (1986) 14: 5591-5603.
Chu, P.W.G. et al., "Putative full length clones of the genomic DNA segments of subterranean cover stunt virus and identification of the segment coding for the viral coat protein," *Virus Research*, (1993) 27: 161-171.
Chu, Te-Hua Terina et al., "Toward Highly Efficient Cell-Type-Specific Gene Transfer with Retroviral Vectors Displaying Single-Chain Antibodies", *J. Virol*., (1997) 71(1):720-725.
Clark, E.G., "Post-weaning multisystemic wasting syndrome," *American Association of Swine Practitioners*, (1997) 499-501.
Cortey, et al., "Further comments on porcine circovirus type 2 (PCV2) genotype definition and nomenclature," Veterinary Microbiology 149 (2011) 522-523.
Cosset, Francois-Loic et al., "Retroviral Retargeting by Envelopes Expressing an N-Terminal Binding Domain", *J. Virol*., (1995) 69:6314-6322.
Cruse et al., "The Illustrated Dictionary of Immunology," Boca Raton: CRC Press (1995) p. 156.
Cruse et al., "The Illustrated Dictionary of Immunology," 2nd edition. Boca Raton: CRC Press (2003) p. 613.
Daft, B. et al., 39th Annual Meeting of American Association of Veterinary Laboratory Diagnosticians, "Interstitial Pneumonia and Lymphadenopathy Associated with Circovirus Infection in a Six-Week Old Pig," *American Association of Veterinary Laboratory Diagnosticians*, Oct. 12-18, 1996 32.
Database Accession No. Q9YTB6, May 1, 1999.
de Boisseson, C. et al., "Molecular characterization of *Porcine circovirus* type 2 isolates from post-weaning multisystemic wasting syndrome-affected and non-affected pigs," 2004, Journal of General Virology, vol. 85, pp. 293-304.
Dedet, V., "Seule certitude: un maladie àpart entière," *La Semaine Veterinaire* p. 54, May 24, 1997.
Derse, D. et al., *J. Virol*.,(1995) 69(3): 1907-1912.
Doe, B. et al., "Induction of HIV-1 envelope (gpUO)-specific cytotoxic T lymphocyte responses in mice by recombinant CHO cell-derived gp120 is enhanced by enzymatic removal of N-linked glycans," Eur. J. Immunol. 1994. 24: 2369-2376.

(56) References Cited

OTHER PUBLICATIONS

Donnelly, John J. et al., "Immunization with DNA" *Journal of Immunological Methods*, 176:145-152 (1994).
Dorland's Illustrated Medical Dictionary, 28th edition. Philadelphia. WB Saunders p. 1787 (1994).
Duck, P. et al., "Probe amplifier system based on Chimeric Cycling Oligonucleotides," *Biotechniques*, (1990) 9:142-147.
Dulac, G.C. et al., *Can. J. Vet. Res.*, (1989) 53:431-433.
Edwards, C.P. et al., "Current applications of COS cell based transient expression systems." *Curr. Op. Biotechnology* (1993) 4:558-563.
Edwards, S. et al., "Evidence of Circovirus Infection in British pigs," *Vet. Rec.*, (1994) 134:680-681.
Ellis et al., "Reproduction of lesions of postweaning multisystemic wasting syndrome in gnotobiotic piglets," *J. Vet. Diagn. Invest.* 11:3-14 (1999).
Ellis et al., "Coinfection by porcine circoviruses and porcine parvovirus in pigs with naturally acquired postweaning multisystemic wasting syndrome" *J. Vet. Diagn. Invest.* 12(1):21-27 (2000).
Ellis, J. et al., "Isolation of Circovirus from legions of Pigs with Postweaning Multisystemic Wasting Syndrome", *Canadian Veterinary Journal*, col. 39, pp. 44-51, Jan. 1998, XP-002068502.
Erickson, A.L. et al., "Hepatitis C Virus-Specific CTL Responses in the Liver of Chimpanzees with Acute and Chronic Hepatitis C", 1993, the Journal of immunology, vol. 151, pp. 4189-4199.
Ertl, H.C.J. et al., "Genetic Immunization" *Viral Immunology*, 9(1):1-9 (1996).
Felgner, et al., "Lipofection: a highly efficient, lipid-mediated DNA-transfection procedure," *Proc. Natl. Acad. Sci.*, (1987) 84: 7413-7417.
Felgner J.H. et al., "Enhanced gene delivery and mechanism studies with a novel series of cationic lipid formulations," *The journal of biological chemistry*, 269(4)2550-2561 (1994).
Fenaux, M. et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2," *Journal of Clinical Microbiology*, Jul. 2000, 38(7):2494-2503.
Fontes, E.P.B. et al., "Interaction between a Geminivirus Replication Protein and Origin DNA is Essential for Viral Replication," *J. Biol. Chem.*, (1994) vol. 269, No. 11:8459-8465.
Fort, Douglas J. et al. "Evaluation of the Developmental Toxicity of Thalidomide Using Frog Embryo Teratogenesis Assay—Xenopus (FETAX): Biotransformation and Detoxification," *Teratogensis, Carcinogenesis, and Mutagenesis*, 20:35-47 (2000).
Fort, M. et al., "Porcine circovirus type 2 (PCV2) vaccination of conventional pigs prevents viremia against PCV2 isolates of different genotypes and geographic origins," Vaccine 26 (2008), 1063-1071.
Fraley et al., "Introduction of Liposome-encapsulated SV40 DNA into cells," *J. Biol. Chem.*, (1980) 255:10431-10435.
GenBank Accession No. AAC61738, Version AAC61738.1, GI:3661517, Sep. 29, 1998.
Genbank Accession # AAF87231, PCV2 ORF2 Protein (2000).
GenBank Accession No. AF027217; May 14, 1998.
GenBank Accession No. AF055391, AF055392, AF055393, and AF055394 and Genbank revision histories (1998).
GenBank Accession No. AF086834, Sep. 29, 1998.
GenBank Accession No. AF086835, Sep. 29, 1998.
GenBank Accession No. AF086836, Sep. 29, 1998.
GenBank Accession No. AF085695, Sep. 30, 1998.
GenBank Accession No. AJ223185, Jul. 7, 1998.
Geysen, H. Mario et al., "Use of peptide synthesis to probe viral antigens for epitopes to a resolution of a single amino acid," 1984, Proceedings of the National Academy of Science USA, vol. 81, pp. 3998-4002.
Geysen, H. Mario et al., "A *PRIORI* Delineation of a Peptide which Mimics a Discontinouous Antigenic Determinant," 1986, Molecular Immunology. vol. 23, No. 7, pp. 709-715.
Gregoriadis G. et al., "Liposome-mediated DNA vaccination" FEBS Letters, Feb. 3, 1997; 402:107-110.
Gregoriadis, Gregory, "Genetic vaccines: strategies for optimization" *Pharmaceutical Research*, 15( 5):661-670 (1998).
Grierson, S.S., et al., "Detection and genetic typing of type 2 porcine circoviruses in archived pig tissues from the UK," 2004, Arch Virol, vol. 149, pp. 1171-1183.
Groner, A. The Biology of Baculoviruses, vol. I, Biological Properties and Molecular Biology, Chapter 9, Specificity and Safety of Baculoviruses 177-202 (1986).
Grierson, S.S., et al., "Genome sequence analysis of 10 Dutch porcine circovirus type 2 (PCV-2) isolates from a PMWS case-control study," 77 *Research in Veterinary Science* 265-268 (2004).
Guateli, J.C. et al., "Isothermal, in vitro amplification of nucleic acids by a multienzyme reaction modeled after retroviral replication," 87 *Proc. Nat'l Acad. Sci., USA* 1874-1878 (1990).
Hackland, A.F. et al., "Coat protein-mediated resistance in transgenic plants," *Arch. Virol.*, (1994) 139: 122.
Haddad, D. et al., "Comparative study of DNA-based immunization vectors: effect of secretion signals on the antibody responses in mice," *FEMS Immunology and Medical Microbiology*, 18(3):193-202 (1997).
Hamel et al., Database EMBL/Genbank/DDBJ (Sep. 26, 1997).
Hamel, A. et al., "Nucleotide Sequence of Procine Circovirus Associated with Postweaning Multisystemic Wasting Syndrome in Pigs", *Journal of Virology*, col. 72, No. 6, pp. 5262-5267, Jun. 1998, XP-002078783.
Hamel, A. et al., "PCR Detection and Characterization of Type-2 Porcine Circovirus," 64 Can. Journal of Vet. Research 44-52 (2000).
Hanson, S.F. et al., "Mutational Analysis of a putative NTP-Binding Domain in the Replication-Associated Protein (ACI) of Bean Golden Mosaic Geminivirus," *Virology*, (1995) 211: 1-9.
Harding, J.C. et al., "Recognizing and diagnosing post-weaning multisystemic wasting syndrome (PMWS)," *Swine Health and Production*, (1997) vol. 5, No. 5: 201-203.
Harding, J.C., "Post-weaning Multisystemic Wasting Syndrome (PMWS): Preliminary Epidemiology and Clinical Presentation," *American Association of Swine Practitioners*, (1997) 503.
Harding, J.C., "The Clinical Expression and Emergence of Porcine Circovirus 2," 98 Veterinary Microbiology 131-135 (2004).
Harding, R.M. et al., "Nucleotide sequence of one compartment of the banana bunchy top virus genome contains a putative replicase gene," *Journal of General Virology*, (1993) 74: 323-328.
Heyraud-Nitschke, F. et al., "Determination of the origin cleavage and joining domain of geminivirus rep proteins," *Nucleic Acids Research*, (1995) vol. 23, No. 6: 910-916.
Horner, G.W., "Pig Circovirus Antibodies present in New Zealand pigs," *Surveillance* (1991) 18(5): 23.
Huygen, K. et al., "Immunogenicity and protective efficacy of a tuberculosis DNA vaccine," *Nature Medicine*, (1996) 2(8): 893-898.
Innis, M.A. et al., "A guide to Methods and Applications," *PCR Protocols* (1990) San Diego, Academic Press.
Inumaru, S. et al., "cDNA Cloning of Porcine Granulocyte-Macrophage Colony-Stimulating Factor" *Immunology and Cell Biology*, 73:474-476, XP-000946635 (1995).
Inumaru et al, "Expression of biologically active recombinant porcine GM-CSF by baculovirus gene expression system", 76 Immunology and Cell Biology 195-201 (1998).
Ishii N. et al., "Cationic liposomes are a strong adjuvant for a DNA vaccine of human immunodeficiency virus type 1" *AIDS Res Hum Retroviruses*, Nov. 1, 1997 13(6):1421-1428.
Izumida, et al., "Establishment of the Attenuated Strain of Porcine Parvovirus of the Live Vaccine and its Biological-Immunological Characteristics," *Japanese Veterinary Science*, 48(2):293-303 (1996).
Kaneda, et al., "Increased Expression of DNA Cointroduced with Nuclear Protein in Adult Rat Liver," *Science*, (1989) 243: 375-378.
Kasahara, N. et al., "Tissue-Specific Targeting of Retroviral Vectors Through Ligan-Receptor Interactions", *Science*, (1994) 266: 1373-1376.

(56) References Cited

OTHER PUBLICATIONS

Kessler, C., "Overview of Amplification on Systems in Non-radioactive Labeling and Detection of Biomolecules," (1992), Springer Verlag, Berlin, New-York: 197-205.
Kievitis, T. et al., "NASBA™ isothermal enzymatic in vitro nucleic acid amplification optimized for the diagnosis of HIV-1 infection," *J. Virol. Methods*, (1991) 35: 273-286.
Kim, Yuna et al., "Characterization of the Recombinant Proteins of Porcine Circovirus Type2 Field Isolate Expressed in the Baculovirus System," *J. Vet Sci*. 2002; 3(1), 19-23.
Kim, J.H. et al., "Genetic characterization of porcine circovirus-2 field isolates from PMWS pigs," *Journal of. Veterinary Science* (2002), vol. 3(1), pp. 31-39.
Klavinskis, Linda S. et al., "Intranasal Immunization with Plasmid DNA-Lipid Complexes Elicits Mucosal Immunity in the Female Genital and Rectal Tracts" *J. Immunol* 1999, pp. 254-262.
Knell, S. et al., "Comparative genetic characterization of Porcine Circovirus type 2 samples from German wild boar populations," *Veterinary Microbiology*, 109 (2005) pp. 169-177.
Kohler, G. et al., "Continuous cultures of fused cells secreting anti-body of predefined specificity," *Nature*, (1975) 256(5517): 495-497.
Krakowka et al., "Activation of the Immune System in the Pivotal Event in the Production of Wasting Disease in Pigs Infected with Porcine Circovirus-2 (PCV-2)," *Vet Pathology*. 38:31-42 (2001).
Krakowka et al., "Immunologic Features of Porcine Circovirus Type-2 Infection," *Viral Immunology*. 15 (4): 567-582 (2002).
Krakowka et al "Viral Wasting Syndrome of Swine: Experimental Reproduction . . . ," 37 Vet. Pathol. 254-263 (2000).
Kwoh, D.Y. et al., "Transcription-based amplification system and detection of amplified human immunodeficiency virus type I with a bead-based sandwich hybridization format," *Proc. Nat'l Acad. Sci., USA*, (1989) 86: 1173-1177.
Ladany, S. et al., "Enzyme immunoassay to determine exposure to Chlamydia pneumoniae (strain TWAR)," *J. Clin. Microbiol*. (1989) 27: 2778-2783.
Lazarowitz, S.G. et al., "Maize streak virus genes essential for systemic spread and symptom development," *The EMBO Journal*, (1989) vol. 8 No. 4: 1023-1032.
LeCann et al., "Piglet Wasting disease,"*Veterinary Record*, p. 660, Dec. 20-27, 1997.
Lekcharoensuk, P. et al., "Epitope Mapping of the Major Capsid Protein of Type 2 Porcine Circovirus (PCV2) by Using Chimeric PCV1 and PCV2," *Journal of Virology*, vol. 78, No. 15, Aug. 2004, pp. 8135-8145.
Li et al., "Genetic analysis of porcine circovirus type 2 (PCV2) strains isolated between 2001 and 2009: genotype PCV2b predominate in postweaning multisystemic wasting syndrome occurrences in eastern China," *Virus Genes* (2010) 40:244-251.
Liu et al., "Maize streak virus coat protein binds single- and double-stranded DNA in vitro," *J. Gen. Virol*., (1997) 78 (Pt 6), 1265-1270.
Liu Q, et al., "Bacterial Expression of an Immunologically Reactive PCV2 ORF2 Fusion Protein," *Protein Expr Purif*. 2001; 21:115-20).
Liu, et al., "Efficient production of type 2 porcine circovirus-like particles by a recombinant baculovirus", *Arch. Virol*. (2008) 153:2291-2295.
Luckow, V.A., "Baculovirus systems for the expression of human gene products." *Curr. Op. Biotechnol*. (1993) 4:564-572.
Mahé et al., "Differential Recognition of ORF 2 Protein from Type 1 and Type 2 Porcine Circoviruses and Identification of Immunorelevant Epitopes", *Journal of General Virology* 81:1815-1824 (2000).
Mankertz et al., "Porcine Circovirus Complete Genome", EMBL Sequence Database XP-002104869 May 22, 1997.
Mankertz, A. et al., "Mapping and Characterization of the Origin of DNA Replication of Porcine Circovirus.", *Journal of Virology* vol. 71, No. 3, pp. 2562-2566, Mar. 1997, XP-002078782.
Mankertz, J. et al., "Transcription Analysis of Porcine Circovirus (PCV)", 1998, Virus Genes, vol. 16, pp. 267-276.

Mankertz, A., "Cloning and sequencing of columbid circovirus (CoCV) a new circovirus from pigeons," 2000, Archives of Virology, vol. 145, pp. 2469-2479.
Mankertz, A., "Characterisation of PCV-2 isolates from Spain, Germany and France," Virus Research, 66 (2000), pp. 65-77.
Marglin, A. et al., "The Synthesis of Bovine Insulin by the Solid Phase Method," *J. Am. Chem. Soc*., (1966) 88(21): 5051-5052.
Mateu et al., "*A single amino acid substitution affects multiple overlapping epitopes in the major antigenic site of foot-and-mouth disease virus of serotype C,*" 71 Journal of General Virology 629-637 (1990).
Matthews, J.A. et al., "Analystical Strategies for the Use of DNA Probes," *Anal. Biochem*., (1988) 169: 1.
McCluskie, Michael J. et al., "Route and Method of Delivery of DNA Vaccine Influence Immune Responses in Mice and Non-Human Primates" *Molecular Medicine* 5:287-300 (1999).
McInnes, C.J. et al., "Cloning and Expression of a cDNA Encoding Ovine Granulocyte-Macrophage Colony-Stimulating Factor" *Gene*, 105: 275-279, XP-002148815 (1991).
McNeilly, F. et al., "Effect of porcine circovirus infection on porcine alveolar macrophage function," *Vet. Immunol. Immunopathol*., (1996) 49: 295-306.
Meehan, B.M. et al., "Sequence of porcine circovirus DNA: affinities with plant circoviruses.", *Journal of General Virology*, vol. 78, No. 1, pp. 221-227, Jan. 1997.
Meehan et al., "Porcine Circovirus Complete Genome", EMBL Sequence Database XP-002104868 (1997).
Meehan, B.M. et al., "Characterization of noval circovirus DNAs associated with wasting syndromes in pigs", *Journal of General Virology*, vol. 79, No. 9, pp. 2171-2179, Sep. 1998, XP-002090386.
Midoux, P. et al., "Specific gene transfer mediated by lactosylated poly-L-lysine into hepatoma cells," *Nucleic Acids Research*, (1993) 21: 871-878.
Miele, E.A. et al., "Autocatalytic Replication of a Recombinant RNA," *J. Mol. Biol*., (1983) 171: 281-295.
Miller, J.S. et al., "The nucleotide sequence of RNA-1 of Indian peanut *Clump furovirus*" *Arch. Virol*. 141:2301-2312, (1996).
Morozov, I. et al., "Detection of a Novel Strain of Procine Circovirus in Pigs with Postweaning Multisystemic Wasting Syndrome", *Journal of Clinical Microbiology*, col. 36, No. 9, pp. 2535-2541, Sep. 1998, XP-002090921.
Morris et al, "Promoter Influence on Baculovirus-Mediated Gene Expression in Permissive and Nonpermissive Insect Cell Line", 66(12) J. Virol 7397-7405 (Dec. 1992).
Morris et al, "Characterization of Productive and Non-Productive ACMNPV Infection in Selected Insect Cell Lines"; 197 J. Virol 339-348 (1993).
Mumford J. A. et al. "Antigenicity and immunogenicity of equine infleuenza vaccines containing a Carbomer adjuvant," *Epidemiol. Infect*. 112: 421-437 (1994).
Nakakura, Norihiko et al. "Synthesis of Heterogeneous mRNA-like RNA and Low-Molecular-Weight RNA before the Midblastula Transition in Embryos of *Xenopus laevis,"* *Developmental Biology*, 123:421-429 (1987).
Nash RA et al., "Molecular cloning and in vivo evaluation of canine granulocyte-macrophage colony-stimulating factor" *Blood* 78(4):930-937, XP 002133949 (1991).
Nawagtigul et al., "Open Reading Frame 2 of Porcine Circovirus Type 2 Encodes a Major Capsid Protein", *Journal of General Virology* 81:2281-2287 (2000).
Nawagitgul et al., Modified Indirect Porcine Circovirus (PCV) Type 2-Based and Recombiant Capsid Protein (ORF2)-Based Enzyme-Linked Immunosorbent Assays for Detection of Antibodies to PCV, *Clinical and Diagnostic Laboratory Immunology*, Jan. 2002, vol. 9, No. 1, pp. 33-40, see the abstract.
Nayer et al., "Detection and Characterization of Porcine Circovirus Associated With Postweaving Multisystemic Wasting Syndrome Pigs", *Can Vet. J*. 38(6):385-386 (1997).
Neddleman, S.B. et al., "A General Method Applicable to the Search for Similarities in the Amino Acid Sequence of Two Proteins", *J. Mol. Biol*., (1970) 48(3):443-453.

(56) References Cited

OTHER PUBLICATIONS

Newport, John et al. "Major Developmental Transition in Early Xenopus Embryos: I. Characterization and Timing of Cellular Changes at the Midblastula Stage," Cell 30:675-686 (1982).

Newport, John et al. "A Major Developmental Transition in Early Xenopus Embryos: II. Control of the Onset of Transcription," Cell 30:687-696 (1982).

Nieuwkoop and Faber "Normal Table of Xenopus laevis (Daudin)—A Systematic and chronological survey of the development from the fertilized egg to the end of metamorposis," Chapter VII, 162-188 Garland Publishing (1994).

Norman, JA et al., "Development of Improved Vectors for DNA-Based Immunization and other Gene Therapy Applications," Vaccine, 15(8): 801-803 (1997).

Nuwaysir, Emile F. et al. "Microarrays and Toxicology: The Advent of Toxicogenomics," Molecular Carcinogenesis, 24:153-159 (1999).

Okada, E. et al., "Intranasal immunization of a DNA vaccine with IL-I2- and Granulocyte-macrophage colony-stimulating Factor (GM-(SF))—expressing plasmids in Liposomes Induces Strong Mucosal and Cell-Mediated immune responses against HIV-1 antigens," The Journal of Immunology, 159:3638-3647 (1997).

Olins, P.O. et al., "Recent advances in heterologous gene expression in Escherichia coli," Curr. Op. Biotechnol. (1993) 4:520-525.

Opriessnig, T. et al., "Emergence of a novel mutant PCV2b variant associated with clinical PCVAD in two vaccinated pig farms in the U.S. concurrently infected with PPV2," Veterinary Microbiology 163 (2013) 177-133.

Opriessnig, T. et al., A PCV2 vaccine based on genotype 2b is more effective than a 2a-based vaccine to protect against PCV2b or combined PCV2a/2b viremia in pigs with concurrent PCV2, PRRSV and PPV infection, Vaccine 31 (2013) 487-494.

Pagano et al., "Factors Influencing the Enhancement of the Infectivity of Poliovirus Ribonucleic Acid by Diethylaminoethyl-Dextran," J. Virol., (1967) 1: 891-897.

Parker, SE et al., " Plasmid DNA gene therapy: Studies with the human interleukin-2 gene in tumor cells in vitro and in the murine B16 melanoma model in vivo," Cancer Gene Therapy, 3(3):175-185 (1996).

Pearson, W.R. et al., "Improved Tools for Biological Sequence Comparison", Proc. Nat'l Acad, Sci., USA, (1988) 85: 2444-2448.

Quintana et al., "Clinical and pathological observations on pigs with postweaning multisystemic wasting syndrome," 149 the Veterinary Record 357-361 (2001).

Ragona et al., "The transcriptional Factor Egr-1 Is Synthesized by Baculovirus-Infected Insect Cells in an Active, DNA-Binding Form", 10(1) DNA and Cell Biology (Jan. 1991).

Restifo, N.P. et al. "The promises of nucleic acid vaccines," Gene Therapy, 7:89-92 (2000).

Rueda et al., "*Effect of different baculovirus inactivation procedures on the integrity and immunogenicity of porcine parvo virus-like particles*," 19 Vaccine 726-734 (2001).

Rolfs, A. et al., "PCR Topics: Usage of Polymerase Chain Reaction in Genetic and Infectious Disease" (1991), Springer-Verlag, Berlin.

Rose, N. et al., "Risk Factors for Porcine Post-Weaning Multisystemic Wasting Syndrome (PMWS) in 149 French Farrow-to-Finish Herds", Preventive Veterinary Microbiology, (2002) 61: 209-225.

Ruitenberg, K. M. et al., "DNA-Mediated Immunization with Glycoprotein D of Equine Herpesvirus 1 (EHV-1) in a Murine Model of EHV-1 Respiratory Infection," Vaccine, 17:237-244 (1999).

Sambrook, J. et al., "Molecular cloning: A Laboratory Manual." Cold Spring Harbor, NY: Cold Spring Harbor Laboratory Press (1989).

Sanchez-Pescador, R., "Rapid chemiluminescent nucleic assays for detection of TEM-1 beta-lactamase-mediated penicillin resistance in Neisseria gororrhoeae and other bacteria," J. Clin. Microbiol., (1988) 26(10): 1934-1938.

Schena, Mark, et al. "Quantitative Monitoring of Gene Expression Patterns with a Complementary DNA Microarray," Science, 270:467-470 (1995).

Schena, Mark et al. "Parallel human genome analysis: Microarray-based expression monitoring of 1000 genes," Proc. Natl. Acad. Sci. USA, 93:10614-10619 (1996).

Schultz, J et al., "Update on Antiviral DNA Vaccine Research (1998-2000)," Intervirology; 43:197-217 (2000).

Segales, J. et al., "First Report of Post-Weaning Multisystemic Wasting Syndrome in Pigs in Spain", Veterinary Record, col. 141, No. 23, pp. 600-601, Dec. 1997, XP-002068504.

Segales et al., "*Changes in peripheral blood leukocyte populations in pigs with natural postweaning multisystemic wasting syndrome (PMWS)*," 81 Veterinary Immunology and Immunopathology 37-44 (2001).

Segales et al, "PCV-2 genotype definition and nomenclature," Vet. Rec. 162: 867-868.

Shiver, J.W., "Immune Responses to HIV gp120 Elicited by DNA Vaccination," Vaccines, (1995), eds Chanock, et al., pp. 95-98, Cold Spring Harbor Laboratory Press, Cold Spring Harbor, New York.

Sin, J-I et al., "Protective Immunity Against Heterologous Challenge with Encephalomyocarditis Virus by VP1 DNA Vaccination: Effect of Coinjection with a Granulocyte-Macrophage Colony Stimulating Factor Gene," Vaccine 15:1827-1833 (1997).

Smith, T.F. et al., "Comparison of Biosequences", Advances in Applied Mathematics, (1981) 2:482-489.

Somasundaram, C. et al., "Enhanced Protective Response and Immuno-Adjuvant Effects of Porcine GM-CSF on DNA Vaccination of Pigs against Aujeszky's Disease Virus," Veterinary Immunology and Immunopathology 70:277-287 (1999).

Sorden et al., "Development of a polyclonal-antibody-based immunohistochemical method for the detection of type 2 porcine circovirus in formalin-fixed, paraffin-embedded tissue", 11 J Vet Diagn Invest 528-530 (1999).

Sparger, E. et al., "Infection of Cats by Injection with DNA of a Feline Immunodeficiency Virus Molecular Clone", 1997, Virology, vol. 238, 157-160.

Tascon, R.E. et al., "Vaccination against tuberculosis by DNA injection," Nature Medicine, (1996) 2(8):888-892.

Terpstra et al., "Potentcy control of modified live viral vaccines for veterinary use," Vaccine 14(6):570-575 (1996).

Tischer, I. et al., "A very small porcine virus with circular single-stranded DNA," Nature, (1982) 295:64-66.

Tischer, I. et al., "Studies on Epideniology and Pathologenicity of Porcine Circovirus," Arch. Virol., (1986) 91:271-276.

Tischer, I. et al., "Replication of Porcine Circovirus: Induction by Glucosamine and Cell Cycle Dependence," 96 Arch Virol 35-57 (1987).

Tischer, I. et al., "Viral DNA from Cells Infected With Porcine Circovirus," Zentralbl Bakteriol Mikrobiol Hyg [A] (1988) 270:280-287.

Tischer, I. et al., "Distribution of antibodies to porcine circovirus in swing populations of different breeding farms", Archives of Virology, vol. 140, No. 4, pp. 737-743, 1995, XP-002104704.

Todd, D. et al., "Purification and Biochemical Characterization of Chicken Anaemia Agent," 71 Journal of General Virology 819-823 (1990).

Todd et al., "Comparison of Three Animal Viruses with Circular Single-Stranded DNA Genomes," Arch Virol., 117:129-135 (1991).

Todd, D. et al., "Dot Blot Hybridization Assay for Chicken Anemia Agent Using a Cloned DNA Probe," 29(5) Journal of Clinical Microbiology 933-939 (May 1991).

Turcitu, et al. "Genetic diversity of porcine circovirus type 2 (PCV2) in the Romanian wild boar population," Research in Veterinary Science 91 (2011) e103-e106.

Urdea, M.S., "A comparison of non-radioisotopic hybridization assay methods using fluorescent chemiluminescent and enzyme labeled synthetic oligodeooxyribonucleotide probes," Nucleic Acids Research, (1988) 11: 4937-4957.

Valsesia-Wittmann, S. et al., "Improvement of Retroviral Retargeting by Using Amino Acid Spacers between an Additional Binding Domain and the N Terminus of Moloney Nurine Leukemia Virus SU", J. Virol, (1996) 70(3):2059-2064.

(56) References Cited

OTHER PUBLICATIONS

Vannier, et al., "Study of the Efficacy of an Inactivated Virus Vaccine Against Porcine Parvovirus," *Ann. Rech. Vet.* 17(4):425-432 (1986).
Verma I., Nature, 389:239-242 (1997).
Vogel, et al., "Nucleic Acid Vaccines," *Clinical Microbiology Reviews* 8(3):406-410 (1995).
Walker, G.T. et al., "Strand displacement amplification—an isothermal, in vitro DNA amplification technique," *Nucleic Acids Res.* (1992) 20: 1691-1696.
Walker, G.T. et al., "Isothermal in vitro amplification of DNA by a restriction enzyme/DNA polymerase system," *Proc. Nat'l Acad. Sci., USA*, (1992) 89: 392-396.
Walker, Ian W., et al., "Development and application of a competitive enzyme-linked immunosorbent assay for the detection of serum antibodies to porcine circovirus," *J Vet Diagn Invest.* 2000; 12:400-5).
Wang, et al., "Genetic variation analysis of Chinese strains of porcine circovirus type 2," *Virus Research* 145 (2009) 151-156.
Watanabe, Y et al., "Highly Efficient Transfection into Primary Cultured Mouse Hepatocytes by Use of Cation-Liposomes: An Application for Immunization," *J. Biochem.* 116:1220-1226 (1994).
Welsh and McClelland et al., Nucleic Acids Research, 18:7213-7218 (1990).
Wen, L. et al., "Genotyping of porcine circovirus type 2 from a variety of clinical conditions in China," *Veterinary Microbiology*, 110 (2005) pp. 141-146.
West et al., "Myocarditis and abortion associated with intrauterine infection of sows with porcine circovirus 2" *J Vet Diagn Invest.* 11: 530-532 (1999).
Wheeler, C.J. et al., "Converting an alcohol to an amine in a cationic lipid dramatically alters the co-lipid requirement, cellular transfection activity and the ultrastructure of DNA-cytofectin complexes," *Biochemica et Biophysica Acta* 1280:1-11, XP 002035803 (1996).
White, B.A. et al. Eds, "PCR Cloning Protocol" *Methods in Molecular Biology*, 67, Humana Press, Towota, (1997).
Willems, Luc et al., "In Vivo Transfection of Bovine Leukemia Provirus into Sheep," 1992, Virology, vol. 189, pp. 775-777.
Xiang Z. et al., "Manipulation of the immune response to a plasmid-encoded viral antigen by coinoculation with plasmids expressing cytokines," *Immunity*, 2:129-135 (1995).
Yang et al.; A Survey on Porcine Circovirus Type 2 Infection and Phylogenetic Analysis of Its ORF2 . . . ; Journal of Zhejiang Unversity Science B ISSN 1673-1581; pp. 148-153; Sep. 2008; Hangzhou City, China.
Yokoyama et al. "DNA immunization: Effects of vehicle and route of administration on the induction of protective antiviral immunity," *FEMS Immunology and Medical Microbiology*, 14:221-230 (1996).

Young, "Fields Virology" 3rd ed. Philadelphia: Lippencott-Raven Publishers Chapter 70—Parvoviruses; vol. 2, p. 2199-2220 (1996).
Young, John A. T. et al., "Efficient Incorporation of Human CD4 Protein into Avian Leukosis Virus Particles", *Science*, (1990) 250(4986):1421-1423.
Zhang, Michael Q. "Large-Scale Gene Expression Data Analysis: A New Challenge to Computational Biologists," *Genome Research*, 9(8):681-688 (1999).
Zhao, T.M. et al., "Infectivity of chimeric human T-cell leukemia virus type I molecular clones assessed by naked DNA inoculation," *Proc. Natl. Acad. Sci., USA* (1996) 93(13): 6653-6658.
Zoller, Mark J. et al., "Oligonucleotide-Directed Mutagenesis: A Simple Method Using Two Oligonucleotide Primers and a Single-Stranded DNA Template," DNA, vol. 3, No. 6, 1984, pp. 479-488.
Does Stress-Free Livestock Mean Safer Food?; http://www.foodnavigator.com; Jun. 4, 2004; Decisionnews Media SAS; 1 page.
U.S. Appl. No. 61/869,353, Aug. 23, 2013, Gregory Haiwick.
Long J. Guo, et al., "Porcine circovirus type 2 (PCV2): genetic variation and newly emerging genotypes in China", Virology Journal 2010, 7:273.
Li Yu, et al., "Genetic Characterization of Porcine Circovirus Type 2 (PVC2) from Pigs in Auhul Province", Journal of Animal and Veterinary Advances 10(8): 1024-1031, 2011.
Olvera et al., "Molecular evolution of porcine circovirus type 2 genomes: Phylogeny and clonality"Virology 357 (2007), pp. 175-185.
Yin et al.,"Self-assembly of virus-like particles of porcine circovirus type 2 capsid protein expressed from *Escherichia coli*", Virology Journal 2010, 7:166.
Guo et al., "First construction of infectious clone for newly emerging mutation porcine circovirus type 2 (PCV2) followed by comparison with PCV2a and PCV2b genotypes in biological characteristics in vitro," Virology Journal 2011, 8:291.
Guo et al., "A Porcine Circovirus Type 2 (PCV2) Mutant with 234 Amino Acids in Capsid Protein Showed More Virulence In Vivo, Compared with Classical PCV2a/b Strain,"PLoS One Jul. 2012, vol. 7, Issue 7, e41463.
Li et al., "Complete Genome Sequence of a Highly Prevalent Porcine Circovirus 2 isolated from Piglet Stool Samples in China,"Journal of Virology, 2012, p. 4716.
Xiao et al., "Complete Genome Sequence of a Novel Porcine Circovirus Type 2b Variant Present in Cases of Vaccine Failures in the United States", Journal of Virology, 2012, vol. 86, No. 22, p. 12469.
GenBank: AY713470.1—Aug. 4, 2005.
GenBank: JQ413808.1—Apr. 8, 2012.
GenBank: HM038017.1—Oct, 22, 2010.
GenBank: FJ948168.1—Aug. 11, 2010.

\* cited by examiner

PCV2B DIVERGENT VACCINE COMPOSITION AND METHODS OF USE

FIELD OF THE INVENTION

The present invention relates to *porcine circovirus*. More particularly, the invention relates to a vaccine composition including a PCV2b divergent ORF2 antigen and its use in a vaccine for protecting pigs against PCV2, including a highly virulent *porcine circovirus* type 2b (PCV2b) divergent strain, and Post-weaning Multisystemic Wasting Syndrome (PMWS).

BACKGROUND OF THE INVENTION

*Porcine circovirus* type 2 (PCV2), a member of Circoviridae family, genus *Circovirus*, is a small nonenveloped circular virus which was initially discovered in 1998. PCV2 is one of the two most prevalent pathogens encountered in the pig industry, the other being *Mycoplasma hyopneumoniae* (M. hyo). Swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In addition to PMWS, PCV2 has been associated with several other diseases, including pseudorabies, *porcine* reproductive and respiratory syndrome (PRRS), enzootic pneumonia, Glasser's disease, streptococcal meningitis, salmonellosis, postweaning colibacillosis, dietetic hepatosis, and suppurative bronchopneumonia. The various clinical manifestations of PCV2 infection in pigs across the age groups has become known as *porcine circovirus*-associated disease (PCVAD), and are characterized by wasting and growth retardation. PRRS virus, Swine Influenza Virus (SIV), M. hyo, and other bacteria have been implicated as major co-factors in the development of PCVAD. PCVAD has continuously been a threat to the global swine industry, causing high economic losses.

PCV2 isolates are currently further subdivided into three genotypes: PCV2a, PCV2b, and PCV2c. PCV2 contains two major open reading frames (ORFs), which encode a protein associated with replication (ORF1, 945 nt), and the virus capsid (ORF2, 702 nt). PCV2 has undergone significant genetic variation in recent years. A newly emergent PCV2 mutant with an additional lysine (K) at the C-terminus of the ORF2-encoded capsid protein compared with classical PCV2a and PCV2b genotypes was isolated in 2008 from a serum sample from an aborted pig (Guo et al., 2010, Virology Journal 7: 273). In this newly emerging PCV2 mutant, a one-base deletion at position 1039 in the genomic sequence resulted in a mutation of the stop codon (from UAA to AAG) in ORF2, to give an ORF2 gene of 705 nt and a new stop codon (Guo et al., 2011, Virology Journal 8: 291). In addition, Knell et al. have reported previously that mutations could occur in the ORF2 gene, because a deletion (T) was found at position 1042 in the 1767 nt genome of one strain (GenBank no. AY713470), which led to elongation by one amino acid (lysine) in the C terminus of the ORF2-encoded capsid protein (Knell et al., 2005, Veterinary Microbiology 109: 169-177). Olvera et al. have also reported elongation by one lysine residue of the C terminus of the capsid protein due to a mutation in the stop codon of ORF2 (Olvera et al., 2007, Virology 357: 175-185). Additionally, a PCV2 strain termed "JSTZ", with GenBank accession No. JQ413808, was detected and identified in stool samples of a piglet with severe diarrhea in China, and its complete 1767 nt genome was sequenced (Li et al., 2012, Journal of Virology (jvi.asm.org), p. 4716). Phylogenetic analyses based on the genome of PCV2 strain JSTZ and the ORFs of other Chinese PCV2 strains indicated that PCV2 strain JSTZ belonged to a novel genotype in China (Li et al., 2012, supra).

Guo et al. assessed the relative virulence of a PCV2 mutant strain termed PCV2b/rBDH or BDH (Gen Bank accession No. HM038017), which had been recovered in 2008 from a sample from an aborted pig with PMWS, and confirmed the greater virulence of the PCV2 mutant strain in piglets than that associated with the classical PCV2a and PCV2b genotypes (Guo et al., 2012, PLoS ONE (plosone.org), Vol. 7, Issue 7, e41463, 1-10). This PCV2 mutant strain demonstrated more severe signs compatible with PMWS, characterized by wasting, coughing, dyspnea, diarrhea, rough hair-coat and depression. Moreover, the pathological lesions and viremia, as well as the viral loads in lymph nodes, tonsils, and spleen, were significantly more severe for piglets challenged with the PCV2 mutant strain compared with those in the groups challenged with classical PCV2a and PCV2b. In addition, a significantly lower average daily weight gain was recorded in the group challenged with the PCV2 mutant strain than in the groups challenged with the prevailing PCV2a and PCV2b genotypes (Guo et al., 2012, supra).

Two PCV2 strains, US22625-33 and US22664-35, were recently identified in cases of suspected vaccine failure in PMWS-affected pigs in a production system located in the United States (Xiao et al., 2012, Journal of Virology (jvi.asm.org), Vol. 86, No. 22, p. 12469). The full genome of these two US strains was found to be comprised of 1767 nt, and the size of its ORF2 gene was 705 nt, encoding an ORF2 protein of 234 aa, which was one amino acid longer than that of common PCV2. Phylogenetic analysis with the nucleotide sequences of ORF2 of classical PCV2a and PCV2b strains suggested that both U.S. PCV2 strains US22625-33 and US22664-35 are closely related to PCV2b. Compared with classic PCV2b, a single base deletion within the ORF2 gene resulted in the addition of a single amino acid (lysine) to the C-terminus of the ORF2 protein. Further sequence BLAST and comparison showed that both U.S. PCV2 strains had a high level of identity (99.9%) with the PCV2 strain, BDH, found in China, and reported to be of increased virulence. One silent mutation (1677A→1677T) in ORF1 was found between BDH and the two U.S. mutant PCV2s. According to the new PCV2 genotype definition and nomenclature criteria (Cortey, et al., 2011, Vet. Microbiol. 149: 522-523; Segales, et al., 2008, Vet. Rec. 162:867-868), all of these novel mutant PCV2 strains could be classified into genotype PCV2b, based on the phylogenetic analysis of the nucleotide sequence of the ORF2 gene (Xiao et al., 2012, supra).

In view of the reported increased virulence of the new PCV2b divergent, as well its presence in cases of suspected vaccine failures in the United States, what is needed is an efficacious vaccine against this new PCV2b divergent. Preferably, this vaccine will be compatible with other *porcine* antigens, such as M. hyo and PRRS virus.

SUMMARY OF THE INVENTION

The present invention provides a vaccine composition for protecting pigs against PCV2, including a highly virulent *porcine circovirus* type 2b (PCV2b) divergent strain, the composition including a PCV2b divergent ORF2 polypeptide, wherein the ORF2 polypeptide comprises Leucine (L)

at position 89, Threonine (T) at position 90, and Aspargine (N) at position 134, according to the numbering of SEQ ID NO: 1. In one embodiment, the composition also provides heterologous protection against classical PCV2a and PCV2b strains.

In one embodiment, the composition is in the form of an inactivated, PCV2b divergent whole virus that comprises and/or expresses the PCV2b divergent ORF2 polypeptide.

In another embodiment, the composition is in the form of an inactivated chimeric virus, wherein the chimeric virus comprises an inactivated recombinant *porcine circovirus* type 1 that comprises and/or expresses the PCV2b divergent ORF2 polypeptide.

In yet another embodiment, the composition is in the form of an isolated, recombinant PCV2b divergent ORF2 polypeptide. In one embodiment, the isolated, recombinant PCV2b divergent ORF2 polypeptide is expressed from a vector. In another embodiment, the vector is a baculovirus or *parapoxvirus*. In a further embodiment, the vector is a live or inactivated vector.

In one embodiment, the PCV2b divergent ORF2 polypeptide which includes Leucine (L) at position 89, Threonine (T) at position 90, and Aspargine (N) at position 134, according to the numbering of SEQ ID NO: 1, further includes at least one residue selected from the group consisting of: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In another embodiment, the PCV2b divergent ORF2 polypeptide which includes Leucine (L) at position 89, Threonine (T) at position 90, and Aspargine (N) at position 134, according to the numbering of SEQ ID NO: 1, further includes a Lysine (K) at residue 59 and a Lysine (K) at residue 234, according to the numbering of SEQ ID NO: 1.

In a further embodiment, the PCV2b divergent ORF2 polypeptide which includes Leucine (L) at position 89, Threonine (T) at position 90, Aspargine (N) at position 134, a Lysine (K) at residue 59 and a Lysine (K) at residue 234, according to the numbering of SEQ ID NO: 1, further includes a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment, the PCV2 divergent ORF2 polypeptide is represented by the amino acid sequence of SEQ ID NO: 1, or a fragment thereof.

In another embodiment, the composition including the PCV2 divergent ORF2 polypeptide further includes at least one additional *porcine* antigen. In one embodiment, the at least one additional antigen is protective against a disease in pigs caused by a microorganism.

In one embodiment, the microorganism includes a bacterium, virus, or protozoan. In another embodiment, the microorganism is selected from, but is not limited to, the following: *porcine reproductive and respiratory syndrome virus* (PRRSV), porcine parvovirus (PPV), Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae, leptospira bacteria, Lawsonia intracellularis, swine influenza virus (SIV), *Escherichia coli* antigen, *Brachyspira hyodysenteriae*, *porcine respiratory coronavirus*, *Porcine Epidemic Diarrhea* (PED) virus, *rotavirus*, Torque teno virus (TTV), *Porcine Cytomegalovirus*, *Porcine enteroviruses*, Encephalomyocarditis virus, a pathogen causative of Aujesky's Disease, Classical Swine fever (CSF) and a pathogen causative of Swine Transmissable Gastroenteritis, or combinations thereof.

In some embodiments, the composition of the present invention further includes an adjuvant. In one embodiment, the adjuvant is selected from, but is not limited to, an oil-in-water adjuvant, a polymer and water adjuvant, a water-in-oil adjuvant, an aluminum hydroxide adjuvant, a vitamin E adjuvant and combinations thereof. In another embodiment, the composition of the present invention further includes a pharmaceutically acceptable carrier.

The present also provides a method of immunizing a pig against PCV2, including a PCV2b divergent strain, the method including administering to the pig a composition of the present invention, as described above. This composition for administration includes a PCV2b divergent ORF2 polypeptide, wherein the ORF2 polypeptide includes Leucine (L) at position 89, Threonine (T) at position 90, and Aspargine (N) at position 134, according to the numbering of SEQ ID NO: 1. As described above, this PCV2b divergent ORF2 polypeptide can further include at least one residue selected from the following: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment, the composition for administration includes a virus comprising and/or expressing the PCV2b divergent ORF2 polypeptide. In another embodiment, the composition for administration includes an isolated, recombinant PCV2b ORF2 polypeptide.

In one embodiment of the method of the present invention, the composition can be administered intramuscularly, intradermally, transdermally, subcutaneously, intranasally, or orally, or by other routes known to those of skill in the art. In another embodiment, the composition is administered in a single dose. In yet another embodiment, the composition is administered as two doses.

In a further embodiment, the composition is administered to pigs having maternally-derived antibodies against PCV2.

In one embodiment, the composition is administered to pigs at 3 weeks of age or older.

The present invention further provides a kit. This kit includes a bottle comprising a vaccine composition according to the present invention for protecting pigs against a highly virulent *porcine circovirus* type 2b (PCV2b) divergent strain. This vaccine composition includes a PCV2b divergent ORF2 polypeptide, wherein the ORF2 polypeptide includes Leucine (L) at position 89, Threonine (T) at position 90, and Aspargine (N) at position 134, according to the numbering of SEQ ID NO: 1. As described above, this PCV2b divergent ORF2 polypeptide can further include at least one residue selected from the following: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment of the kit, the vaccine composition is in the form of a virus comprising and/or expressing the PCV2b divergent ORF2 polypeptide. In another embodiment of the kit, the vaccine composition is in the form of an isolated, recombinant PCV2b divergent ORF2 polypeptide.

In one embodiment of the kit, the vaccine composition in the bottle is provided as a ready-to-use liquid composition. In another embodiment of the kit, the vaccine composition in the bottle is provided in a lyophilized form. In a further embodiment, the kit can include a diluent. In yet another embodiment, the kit can further include an instruction manual which contains the information for administration of the vaccine composition.

BRIEF DESCRIPTION OF THE SEQUENCES

Figure 1:
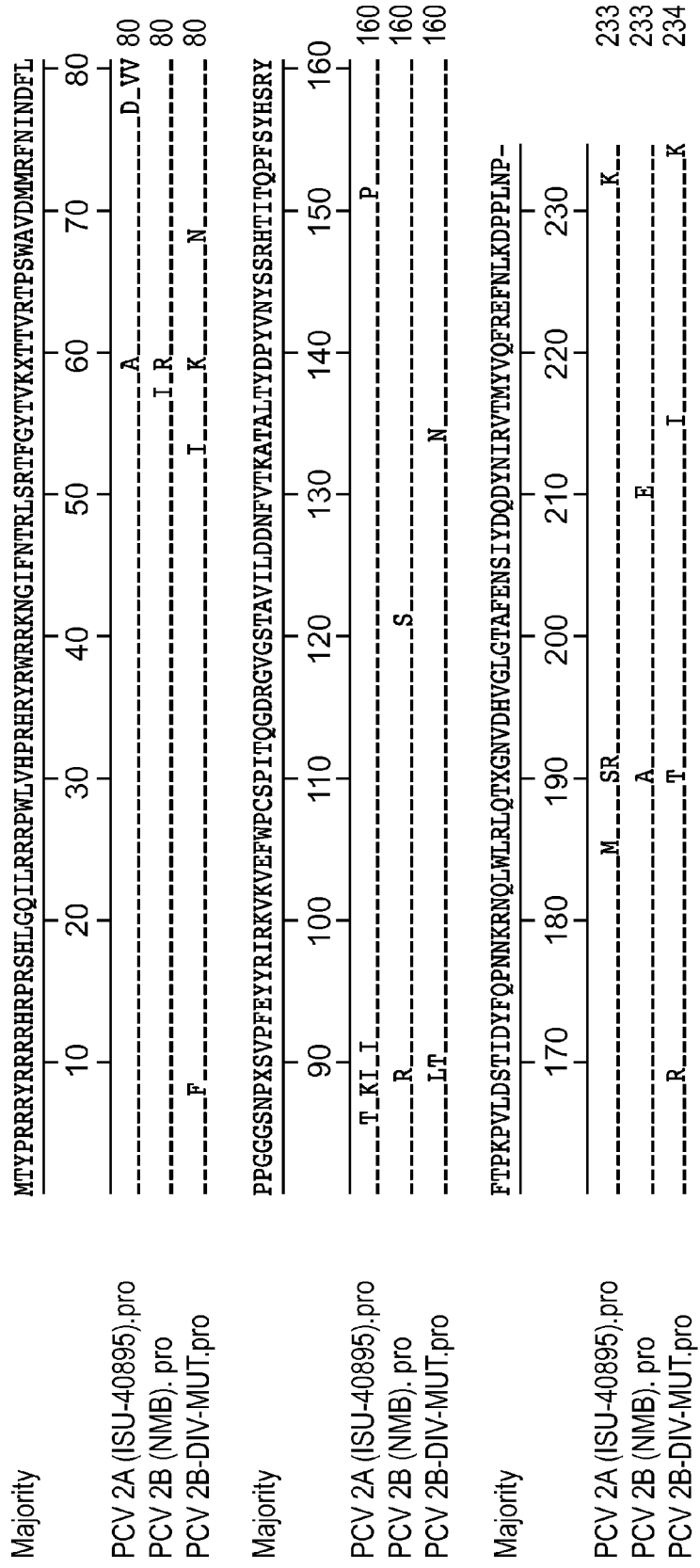
FIG. 1 shows the amino acid sequence alignments between the capsid sequence of the PCV2b divergent strain termed "PCV2B-DIV-MUT", and those of e classical PCV2A strain (termed ISU-40895) end a classical PCV2b strain (termed NMB), The capsid sequences of PCV2 strains PCV2B-DIV-MUT, ISU-40895, and NMB are represented by SEQ ID NO: 1, SEQ ID NO: 58, and SEQ ID NO: 62, respectively. The majority sequence is represented by SEQ ID NO: 67.

As used herein, the PCV2 isolates represented by SEQ ID NOs: 1 to 57 and 66 are representative examples of PCV2b divergent strains.

SEQ ID NO: 1 is the amino acid sequence corresponding to the full-length capsid of a PCV2b divergent strain termed PCV2B-DIV-MUT herein.

SEQ ID NO: 2 is the nucleotide sequence encoding the full-length capsid of a PCV2b divergent strain termed PCV2B-DIV-MUT herein.

SEQ ID NO: 3 is the amino acid sequence corresponding to the full-length capsid of the PCV2 strain: 798-1, with GenBank Accession number AB462384.

SEQ ID NO: 4 is the nucleotide sequence encoding the full-length capsid of the PCV2 strain: 798-1, with GenBank Accession number AB462384.

SEQ ID NO: 5 is the amino acid sequence corresponding to the full-length capsid of the PCV2 strain: FF, with GenBank Accession number DQ231516.

SEQ ID NO: 6 is the nucleotide sequence encoding the full-length capsid of the PCV2 strain: FF, with GenBank Accession number DQ231516.

SEQ ID NO: 7 is the amino acid sequence corresponding to the full-length capsid of the PCV2 strain: VC 2002-k2, with GenBank Accession number EF990645.

SEQ ID NO: 8 is the nucleotide sequence encoding the full-length capsid of the PCV2 strain: VC 2002-k2, with GenBank Accession number EF990645.

SEQ ID NO: 9 is the amino acid sequence corresponding to the full-length capsid of the PCV2 isolate: GY09, with GenBank Accession number GQ845025.

SEQ ID NO: 10 is the nucleotide sequence encoding the full-length capsid of the PCV2 strain: GY09, with GenBank Accession number GQ845025.

SEQ ID NO: 11 is the amino acid sequence corresponding to the full-length capsid of the PCV2 isolate: X509, with GenBank Accession number GQ845028.

SEQ ID NO: 12 is the nucleotide sequence encoding the full-length capsid of the PCV2 strain: X509, with GenBank Accession number GQ845028.

SEQ ID NO: 13 is the amino acid sequence corresponding to the full-length capsid of the PCV2 isolate: SD1d01, with GenBank Accession number HM535640.

SEQ ID NO: 14 is the nucleotide sequence encoding the full-length capsid of the PCV2 isolate: SD1d01, with GenBank Accession number HM535640.

SEQ ID NO: 15 is the amino acid sequence corresponding to the full-length capsid of the PCV2 isolate: SD1d02, with GenBank Accession number HM755880.

SEQ ID NO: 16 is the nucleotide sequence encoding the full-length capsid of the PCV2 isolate: SD1d02, with GenBank Accession number HM755880.

SEQ ID NO: 17 is the amino acid sequence corresponding to the full-length capsid of the PCV2 isolate: HM01, with GenBank Accession number HM755881.

SEQ ID NO: 18 is the nucleotide sequence encoding the full-length capsid of the PCV2 isolate: HM01, with GenBank Accession number HM755881.

SEQ ID NO: 19 is the amino acid sequence corresponding to the full-length capsid of the PCV2 strain: NIVS-1, with GenBank Accession number HQ378157.

SEQ ID NO: 20 is the nucleotide sequence encoding the full-length capsid of the PCV2 strain: NIVS-1, with GenBank Accession number HQ378157.

SEQ ID NO: 21 is the amino acid sequence corresponding to the full-length capsid of the PCV2 isolate: C/2010-2*, with GenBank Accession number JF683394.

SEQ ID NO: 22 is the nucleotide sequence encoding the full-length capsid of the PCV2 isolate: C/2010-2*, with GenBank Accession number JF683394.

SEQ ID NO: 23 is the amino acid sequence corresponding to the full-length capsid of the PCV2 isolate: G/2009-2, with GenBank Accession number JF683408.

SEQ ID NO: 24 is the nucleotide sequence encoding the full-length capsid of the PCV2 isolate: G/2009-2, with GenBank Accession number JF683408.

SEQ ID NO: 25 is the amino acid sequence corresponding to the full-length capsid of the PCV2 isolate: 1/2010, with GenBank Accession number JF927984.

SEQ ID NO: 26 is the nucleotide sequence encoding the full-length capsid of the PCV2 isolate: 1/2010, with GenBank Accession number JF927984.

SEQ ID NO: 27 is the amino acid sequence corresponding to the full-length capsid of the PCV2 isolate: J/2010, with GenBank Accession number JF927985.

SEQ ID NO: 28 is the nucleotide sequence encoding the full-length capsid of the PCV2 isolate: J/2010, with GenBank Accession number JF927985.

SEQ ID NO: 29 is the amino acid sequence corresponding to the full-length capsid of the PCV2 isolate: K/2010, with GenBank Accession number JF927986.

SEQ ID NO: 30 is the nucleotide sequence encoding the full-length capsid of the PCV2 isolate: K/2010, with GenBank Accession number JF927986.

SEQ ID NO: 31 is the amino acid sequence corresponding to the full-length capsid of the PCV2 isolate: M/2010, with GenBank Accession number JF927988.

SEQ ID NO: 32 is the nucleotide sequence encoding the full-length capsid of the PCV2 isolate: M/2010, with GenBank Accession number JF927988.

SEQ ID NO: 33 is the amino acid sequence corresponding to the capsid of the PCV2 isolate: WB/ROM89, with GenBank Accession number JN006445.

SEQ ID NO: 34 is the nucleotide sequence encoding the capsid of the PCV2 isolate: WB/ROM89, with GenBank Accession number JN006445.

SEQ ID NO: 35 is the amino acid sequence corresponding to the full-length capsid of the PCV2 isolate: EU-RO-F4-3, with GenBank Accession number JN382188.

SEQ ID NO: 36 is the nucleotide sequence encoding the full-length capsid of the PCV2 isolate: EU-RO-F4-3, with GenBank Accession number JN382188.

SEQ ID NO: 37 is the amino acid sequence corresponding to the full-length capsid of the PCV2 isolate: HNing09, with GenBank Accession number JN411096.

SEQ ID NO: 38 is the nucleotide sequence encoding the full-length capsid of the PCV2 isolate: HNing09, with GenBank Accession number JN411096.

SEQ ID NO: 39 is the amino acid sequence corresponding to the full-length capsid of the PCV2 isolate: YWu09, with GenBank Accession number JN411099.

SEQ ID NO: 40 is the nucleotide sequence encoding the full-length capsid of the PCV2 isolate: YWu09, with GenBank Accession number JN411099.

SEQ ID NO: 41 is the amino acid sequence corresponding to the full-length capsid of the PCV2 isolate: CH-IVT4, with GenBank Accession number JX984586.

SEQ ID NO: 42 is the nucleotide sequence of the full-length capsid gene of the PCV2 isolate: CH-IVT4, with GenBank Accession number JX984586.

SEQ ID NO: 43 is the amino acid sequence corresponding to the full-length capsid of the PCV2 isolate: CH-IVT6, with GenBank Accession number JX984588.

SEQ ID NO: 44 is the nucleotide sequence of the full-length capsid gene of the PCV2 isolate: CH-IVT6, with GenBank Accession number JX984588.

SEQ ID NO: 45 is the amino acid sequence corresponding to the full-length capsid of the PCV2 isolate: CH-IVT7, with GenBank Accession number JX984589.

SEQ ID NO: 46 is the nucleotide sequence of the full-length capsid gene of the PCV2 isolate: CH-IVT7, with GenBank Accession number JX984589.

SEQ ID NO: 47 is the amino acid sequence corresponding to the full-length capsid of a PCV2 isolate, with GenBank Accession number JX984590.

SEQ ID NO: 48 is the nucleotide sequence of the full-length capsid gene of a PCV2 isolate, with GenBank Accession number JX984590.

SEQ ID NO: 49 is the amino acid sequence corresponding to the full-length capsid of the PCV2 isolate: CH-IVT9, with GenBank Accession number JX984591.

SEQ ID NO: 50 is the nucleotide sequence of the full-length capsid gene of the PCV2 isolate: CH-IVT9, with GenBank Accession number JX984591.

SEQ ID NO: 51 is the amino acid sequence corresponding to the full-length capsid of the PCV2 isolate: CH-IVT10, with GenBank Accession number JX984592.

SEQ ID NO: 52 is the nucleotide sequence of the full-length capsid gene of the PCV2 isolate: CH-IVT10, with GenBank Accession number JX984592.

SEQ ID NO: 53 is the amino acid sequence corresponding to the full-length capsid of the PCV2 isolate: CH-IVT11, with GenBank Accession number JX984593.

SEQ ID NO: 54 is the nucleotide sequence of the full-length capsid gene of the PCV2 isolate: CH-IVT11, with GenBank Accession number JX984593.

SEQ ID NO: 55 is the amino acid sequence corresponding to the full-length capsid of the PCV2 isolate: GDYX, with GenBank Accession number JX519293.

SEQ ID NO: 56 is the nucleotide sequence encoding the full-length capsid of the PCV2 isolate: GDYX, with GenBank Accession number JX519293.

SEQ ID NO: 57 is the complete genome sequence of the PCV2 isolate: GDYX, with GenBank Accession number JX519293.

SEQ ID NO: 58 is the amino acid sequence corresponding to the full-length capsid of a classical PCV2a isolate: ISU-40895, with GenBank Accession number AF264042.

SEQ ID NO: 59 is the nucleotide sequence encoding the full-length capsid of a PCV2a isolate: ISU-40895, with GenBank Accession number AF264042.

SEQ ID NO: 60 is the amino acid sequence corresponding to the full-length capsid of a classical PCV2a isolate: Imp.1010-Stoon, with GenBank Accession number AF055392.

SEQ ID NO: 61 is the nucleotide sequence encoding the full-length capsid of a classical PCV2a isolate: Imp.1010-Stoon, with GenBank Accession number AF055392.

SEQ ID NO: 62 is the amino acid sequence corresponding to the full-length capsid of a classical PCV2b strain: NMB, with GenBank Accession number GU799576.

SEQ ID NO: 63 is the nucleotide sequence encoding the full-length capsid of a classical PCV2b isolate: NMB, with GenBank Accession number GU799576.

SEQ ID NO: 64 is the amino acid sequence corresponding to the full-length capsid of a classical PCV2c strain: DK1980PMWSfree, with GenBank Accession number EU148503.

SEQ ID NO: 65 is the nucleotide sequence encoding the full-length capsid of a classical PCV2c strain: DK1980PMWSfree, with GenBank Accession number EU148503.

SEQ ID NO: 66 is the complete genome sequence of the PCV2 divergent termed "PCV2b-DIV-MUT".

DETAILED DESCRIPTION OF THE INVENTION

As used in the specification and claims, the singular form "a", "an" and "the" include plural references unless the context clearly dictates otherwise. For example, the term "a protein antigen" includes a plurality of protein antigens, including mixtures thereof.

As used herein, the term "comprising" is intended to mean that the compositions and methods include the recited elements, but do not exclude other elements.

As used herein, the terms "PCV2b divergent strain", "PCV2b divergent", "PCV2 mutant", "novel mutant PCV2", "mutant PCV2", and the like refer to a highly virulent PCV2b strain which encodes an ORF2 capsid polypeptide that includes Leucine (L) at position 89, Threonine (T) at position 90, and Asparagine (N) at position 134, according to the numbering of SEQ ID NO: 1. The encoded PCV2b divergent ORF2 polypeptide can further include at least one residue selected from: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215 according to the numbering of SEQ ID NO: 1.

As used herein, the term "a PCV2b divergent ORF2 polypeptide" is intended to include an virus comprising and/or expressing the PCV2b divergent ORF2 polypeptide, such that the ORF2 polypeptide is a component of the virus itself (e.g., protein coat of the virus). The virus can be PCV, but should not be construed to be limited to such, and can include other viruses. This term is also intended to include an isolated, recombinant PCV2b divergent ORF2 polypeptide.

The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten). The term "antigen" can include a whole virus, a polypeptide, or a fragment thereof.

As used herein, the term "vaccine composition" includes at least one antigen or immunogen in a pharmaceutically acceptable vehicle useful for inducing an immune response in a host. Vaccine compositions can be administered in dosages, and by techniques well known to those skilled in the medical or veterinary arts, taking into consideration factors such as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray, or mixed in food and/or water, or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences" (1990), may be consulted to prepare suitable preparations, without undue experimentation.

As defined herein, an "immunogenic or immunological composition", refers to a composition of matter that comprises at least one antigen which elicits an immunological response in the host of a cellular and/or antibody-mediated immune response to the composition or vaccine of interest.

The term "immune response" as used herein refers to a response elicited in an animal. An immune response may refer to cellular immunity (CMI), humoral immunity, or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response, such that resistance to new infection will be enhanced, and/or the clinical severity of the disease reduced. Such protection will be demonstrated by either a reduction or lack of symptoms normally displayed by an infected host, a quicker recovery time, and/or a lowered viral titer in the infected host.

As used herein, the term "immunogenicity" means capable of producing an immune response in a host animal against an antigen or antigens. This immune response forms the basis of the protective immunity elicited by a vaccine against a specific infectious organism.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right, and are believed to function synergistically.

As used herein, the term "multivalent" means a vaccine containing more than one antigen, whether from the same microbiological species (e.g., different isolates of *Mycoplasma hyopneumoniae* or PCV), from different species (e.g., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

The term "pig" or "piglet" as used herein means an animal of *porcine* origin, while "sow" refers to a female pig of reproductive age and capability. A "gilt" is a female pig who has never been pregnant.

As used herein, the term "virulent" means an isolate that retains its ability to be infectious in an animal host and is capable of causing disease in the host animal.

"Inactivated vaccine" means a vaccine composition containing an infectious organism or pathogen that is no longer capable of replication or growth. The pathogen may be bacterial, viral, protozoal or fungal in origin. Inactivation may be accomplished by a variety of methods, including freeze-thawing, chemical treatment (for example, treatment with β-propiolactone (BPL) or formalin), sonication, radiation, heat, or any other conventional means sufficient to prevent replication or growth of the organism, while maintaining its immunogenicity.

The term "variant" as used herein refers to a polypeptide or a nucleic acid sequence encoding a polypeptide, that has one or more conservative amino acid variations or other minor modifications such that the corresponding polypeptide has substantially equivalent function when compared to the wild-type polypeptide. The term "variant" can also refer to a microorganism comprising a polypeptide or nucleic acid sequence having said variations or modifications as well.

"Conservative variation" denotes the replacement of an amino acid residue by another biologically similar residue, or the replacement of a nucleotide in a nucleic acid sequence such that the encoded amino acid residue does not change, or is another biologically similar residue. Examples of conservative variations include the substitution of one hydrophobic residue, such as isoleucine, valine, leucine or methionine, for another hydrophobic residue, or the substitution of one polar residue with another, such as the substitution of arginine for lysine, glutamic acid for aspartic acid, or glutamine for asparagine, and the like. The term "conservative variation" also includes a substituted amino acid in place of a parent amino acid, provided that antibodies raised to the substituted polypeptide also immunoreact with the parent (unsubstituted) polypeptide.

As used herein, the terms "pharmaceutically acceptable carrier" and "pharmaceutically acceptable vehicle" are interchangeable, and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, coloring additives, and the like.

"North American PRRS virus" means any PRRS virus having genetic characteristics associated with a North American PRRS virus isolate, such as, but not limited to, the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS virus (Mardassi, H. et al., 1995, Arch. Virol. 140:1405-1418); and North American PRRS virus isolate VR 2385 (Meng, X.-J et al., 1994, J. Gen. Virol. 75:1795-1801). Additional examples of North American PRRS virus strains are known in the art. Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus". Further examples of European PRRS virus strains are known in the art.

As used herein, a genetically modified virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of pathological lesions, etc.

An "infectious clone" is an isolated or cloned genome of the disease agent (e.g. viruses) that can be specifically and purposefully modified in the laboratory, and then used to re-create the live genetically-modified organism. A live genetically-modified virus produced from the infectious clone can be employed in a live viral vaccine. Alternatively, inactivated virus vaccines can be prepared by treating the live virus derived from the infectious clone with inactivating agents such as formalin, beta-propriolactone, binary ethylenemine or hydrophobic solvents, acids, etc., by irradiation with ultraviolet light or X-rays, by heating, etc.

The present invention provides a vaccine composition for protecting pigs against PCV2, including a highly virulent *porcine circovirus* type 2b (PCV2b) divergent strain, the composition including a PCV2b divergent ORF2 polypeptide, wherein the ORF2 polypeptide comprises Leucine (L) at position 89, Threonine (T) at position 90, and Aspargine (N) at position 134, according to the numbering of SEQ ID NO: 1. As described above, this PCV2b divergent ORF2 polypeptide can further include at least one residue selected from the following: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment, the PCV2b divergent ORF2 polypeptide which includes Leucine (L) at position 89, Threonine (T) at position 90, and Aspargine (N) at position 134, according to the numbering of SEQ ID NO: 1, further includes a Lysine (K) at residue 59 and a Lysine (K) at residue 234, according to the numbering of SEQ ID NO: 1.

In a further embodiment, the PCV2b divergent ORF2 polypeptide which includes Leucine (L) at position 89, Threonine (T) at position 90, Aspargine (N) at position 134, a Lysine (K) at residue 59 and a Lysine (K) at residue 234, according to the numbering of SEQ ID NO: 1, further includes a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment, the PCV2 divergent ORF2 polypeptide is represented by the amino acid sequence of SEQ ID NO: 1 or a fragment thereof. However, the present invention is not limited to this embodiment. For example, in other embodiments, the PCV2 divergent ORF2 polypeptide can be selected from, but is not limited to, the amino acid sequence of SEQ ID NO: 3 or a fragment thereof, the amino acid sequence of SEQ ID NO: 5 or a fragment thereof, the amino acid sequence of SEQ ID NO: 7 or a fragment thereof, the amino acid sequence of SEQ ID NO: 9 or a fragment thereof, the amino acid sequence of SEQ ID NO: 11 or a fragment thereof, the amino acid sequence of SEQ ID NO: 13 or a fragment thereof, the amino acid sequence of SEQ ID NO: 13 or a fragment thereof, the amino acid sequence of SEQ ID NO: 15 or a fragment thereof, the amino acid sequence of SEQ ID NO: 17 or a fragment thereof, the amino acid sequence of SEQ ID NO: 19 or a fragment thereof, the amino acid sequence of SEQ ID NO: 21 or a fragment thereof, the amino acid sequence of SEQ ID NO: 23 or a fragment thereof, the amino acid sequence of SEQ ID NO: 25 or a fragment thereof, the amino acid sequence of SEQ ID NO: 27 or a fragment thereof, the amino acid sequence of SEQ ID NO: 29 or a fragment thereof, the amino acid sequence of SEQ ID NO: 31 or a fragment thereof, the amino acid sequence of SEQ ID NO: 33 or a fragment thereof, the amino acid sequence of SEQ ID NO: 35 or a fragment thereof, the amino acid sequence of SEQ ID NO: 37 or a fragment thereof, the amino acid sequence of SEQ ID NO: 39 or a fragment thereof, the amino acid sequence of SEQ ID NO: 41 or a fragment thereof, the amino acid sequence of SEQ ID NO: 43 or a fragment thereof, the amino acid sequence of SEQ ID NO: 45 or a fragment thereof, the amino acid sequence of SEQ ID NO: 47 or a fragment thereof, the amino acid sequence of SEQ ID NO: 49 or a fragment thereof, the amino acid sequence of SEQ ID NO: 51 or a fragment thereof, the amino acid sequence of SEQ ID NO: 53 or a fragment thereof, or the amino acid sequence of SEQ ID NO: 55 or a fragment thereof.

In one embodiment, the vaccine compositions of the present invention include at least one additional antigen. In one embodiment, the at least one additional antigen is protective against a disease in pigs caused by a microorganism.

In some embodiments, the at least one additional antigen component is protective against a disease in pigs caused by bacteria, viruses, or protozoans that are known to infect pigs. Examples of such microorganisms include, but are not limited to, the following: M. hyo, *porcine reproductive and respiratory syndrome virus* (PRRSV), *porcine parvovirus* (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae,* leptospira bacteria, *Lawsonia intracellularis,* swine influenza virus (SIV), *Escherichia coli* antigen, *Brachyspira hyodysenteriae, porcine respiratory coronavirus, Porcine Epidemic Diarrhea* (PED) virus, *porcine rotavirus* (e.g., groups A, B, and C), Torque teno virus (TTV), *Porcine Cytomegalovirus, Porcine enteroviruses,* Encephalomyocarditis virus, a pathogen causative of Aujesky's Disease, Classical Swine fever (CSF) and a pathogen causative of Swine Transmissable Gastroenteritis, or combinations thereof.

In one embodiment, the at least one additional antigen is *Mycoplasma hyopneumoniae* (M. hyo). In another embodiment, the at least one additional antigen is a PRRS virus, such as a North American PRRS virus strain, a Chinese PRRS virus strain, or a European PRRS virus strain. It is also anticipated that the at least one additional antigen can be a different isolate of PCV2, such as a classical PCV2a strain, a classical PCV2b strain, or other PCV2 genotypes.

In one embodiment, the composition is in the form of an inactivated, PCV2b divergent whole virus that comprises and/or expresses a PCV2b divergent ORF2 polypeptide.

In one embodiment, the ORF2 capsid gene of the PCV2b divergent whole virus corresponds to SEQ ID NO: 2. In a further embodiment, the amino acid sequence of the PCV2b divergent ORF2 polypeptide which is expressed by the PCV2b divergent whole virus corresponds to SEQ ID NO: 1 or a fragment thereof. However, the present invention is not limited to these embodiments. For example, in some embodiments, the PCV2b divergent ORF2 polypeptide expressed by the PCV2b divergent whole virus can be selected from any of the following sequences or fragments thereof: SEQ ID NO: 3, SEQ ID NO: 5 SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, or SEQ ID NO: 55. The corresponding ORF2 gene sequences are described herein.

In another embodiment, the composition is in the form of an inactivated chimeric virus, wherein the chimeric virus comprises an inactivated recombinant *porcine circovirus* type 1 that comprises and/or expresses a PCV2b divergent ORF2 polypeptide (chimeric PCV1-2b virus). Chimeric *porcine circoviruses* and methods for their preparation are described in WO 03/049703 A2, and also in U.S. Pat. Nos. 7,279,166 and 7,575,752, which are incorporated herein by reference in their entirety.

In one embodiment, the ORF2 capsid gene of the chimeric PCV1-2 virus corresponds to SEQ ID NO: 2. In a further embodiment, the amino acid sequence of the PCV2b divergent ORF2 polypeptide which is expressed by the chimeric PCV1-2b virus corresponds to SEQ ID NO: 1 or a fragment thereof. However, the present invention is not limited to these embodiments. For example, in some embodiments, the PCV2b divergent ORF2 polypeptide expressed by the chimeric PCV1-2b virus can be selected from any of the following sequences or fragments thereof: SEQ ID NO: 3, SEQ ID NO: 5 SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, or SEQ ID NO: 55.

In yet another embodiment, the composition is in the form of an isolated, recombinant PCV2b divergent ORF2 polypeptide. In one embodiment, the isolated, recombinant PCV2b divergent ORF2 polypeptide is expressed from a vector, such as baculovirus. Alternatively, other known expression vectors can be used, such as including, but not limited to, parapox vectors. In one embodiment, the vector can be a live or inactivated vector.

In a further embodiment, the recombinantly-expressed PCV2b divergent ORF2 polypeptide corresponds to SEQ ID NO: 1 or a fragment thereof. Alternatively, in some embodiments, the recombinantly-expressed PCV2b divergent ORF2 polypeptide can be selected from any of the following or fragments thereof: SEQ ID NO: 3, SEQ ID NO: 5 SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, or SEQ ID NO: 55.

In some forms, immunogenic portions of PCV2 divergent ORF2 protein are used as the antigenic component in the composition. For example, truncated and/or substituted forms or fragments of PCV2 divergent ORF2 protein may be employed in the compositions of the present invention.

It is understood by those of skill in the art that variants of the PCV2b divergent ORF2 polypeptides can be employed in the compositions of the present invention, provided they still retain the antigenic characteristics that render it useful in the vaccine compositions of this invention. Preferably, PCV2b divergent variants have at least 80%, preferably at least 85%, more preferably at least 90%, even more preferably at least 95% sequence identity with the full-length genomic sequence of the PCV2 isolate termed PCV2B-DIV-ITT. The antigenic characteristics of an immunological composition can be, for example, estimated by the challenge experiment as provided in the Examples. Moreover, the antigenic characteristic of a modified PCV2b divergent ORF2 antigen is still retained when the modified antigen confers at least 70%, preferably 80%, more preferably 90% of the protective immunity as compared to the wild-type PCV2b divergent ORF2 protein having SEQ ID NO: 1.

The PCV2b divergent ORF2 antigen component is provided in the immunogenic/vaccine composition at an antigen inclusion level effective for inducing the desired immune response, namely reducing the incidence of or lessening the severity of clinical signs resulting from infection with a highly virulent PCV2b strain, an example of which is the virus termed PCV2B-DIV-MUT herein. In some embodiments, the composition also provides heterologous protection against classical PCV2a and PCV2b strains.

In one embodiment, a vaccine composition according to the present invention is in the form of an inactivated recombinant *porcine circovirus* type 1 that comprises and/or expresses a PCV2b divergent ORF2 polypeptide (chimeric PCV1-2bDIV virus). This chimeric virus is included in the compositions of the invention at a level of at least 1.0≤RP≤5.0, wherein RP is the Relative Potency unit determined by ELISA antigen quantification (in vitro potency test) compared to a reference vaccine. In another embodiment, a chimeric PCV1-2bDIV virus is included in the composition of the invention at a final concentration of about 0.5% to about 5% of 20-times (20×) concentrated bulk PCV1-2bDIV antigen.

In another embodiment, a vaccine composition according to the present invention is in the form of an in the form of an inactivated, PCV2b divergent whole virus that comprises and/or expresses a PCV2b divergent ORF2 polypeptide. This virus is included in the compositions of the invention at a level of at least 1.0≤RP≤5.0, wherein RP is the Relative Potency unit determined by ELISA antigen quantification (in vitro potency test) compared to a reference vaccine. In another embodiment, an inactivated PCV2b divergent whole virus is included in the composition of the invention at a final concentration of about 0.5% to about 5% of 20-times (20×) concentrated bulk PCV2b divergent ORF2 antigen.

In yet another embodiment, a vaccine composition according to the present invention is in the form of an isolated, recombinant PCV2b divergent ORF2 polypeptide. The PCV2b divergent ORF2 recombinant protein can be included in the compositions of the invention at a level of at least 0.2 µg antigen/ml of the final immunogenic/vaccine composition (µg/ml). In a further embodiment, the recombinant PCV2b divergent ORF2 polypeptide inclusion level is from about 0.2 to about 400 µg/ml. In yet another embodiment, the recombinant PCV2b divergent ORF2 polypeptide inclusion level is from about 0.3 to about 200 µg/ml. In a still further embodiment, the recombinant PCV2b divergent ORF2 polypeptide inclusion level is from about 0.35 to about 100 µg/ml. In still another embodiment, the recombinant PCV2b divergent ORF2 polypeptide inclusion level is from about 0.4 to about 50 µg/ml.

In one embodiment, a vaccine composition of the present invention includes the combination of a PCV2b divergent ORF2 polypeptide, and at least one M. hyo soluble antigen (e.g., two or more). In one embodiment, a vaccine composition of the invention includes a PCV2b divergent ORF2 polypeptide and one or more of the following M. hyo specific protein antigens: M. hyo proteins of approximately 46 kD (p46), 64 kD (p64) and 97 kD (p97) molecular weights. The M. hyo protein of approximately 64 kD (p64) may be alternatively referred to as the p65 surface antigen from M. hyo described by Kim et al. [Infect. Immun. 58(8):2637-2643 (1990)], as well as in U.S. Pat. No. 5,788,962. Futo et al. described the cloning and characterization of a 46 kD surface protein from M. hyo, which can be employed in the compositions of this invention [J. Bact 177:1915-1917 (1995)]. Zhang et al. described and characterized a p97 adhesin protein of M. hyo [Infect. Immun. 63:1013-1019, 1995]. Additionally, King et al. described a 124 kD protein termed Mhp1 from the P-5722 strain of M. hyo and presented data suggesting that Mhp1 and p97 are the same protein [Vaccine 15:25-35 (1997)]. Such p97 proteins can be employed in the compositions of this invention. Vaccine compositions of the present invention may include further M. hyo specific protein antigens such as, but not limited to, proteins of approximately 41 kD (p41), 42 kD (p42), 89 kD (p89), and 65 kD (p65). See, Okada et al., 2000, J. Vet. Med. B 47:527-533 and Kim et al., 1990, Infect. Immun. 58(8):2637-2643. In addition, the M. hyo component can include M. hyo specific protein antigens of approximately 102 kD (p102) and 216 kD (p216). See, U.S. Pat. Nos. 6,162,435 and 7,419,806 to Minion et al.

In another embodiment, a vaccine composition of the present invention includes the combination of a PCV2b divergent ORF2 polypeptide, at least one M. hyo soluble antigen (e.g., two or more), as well as a PRRS virus antigen. Suitable PRRS virus antigens for use in PCV2b divergent/M. hyo/PRRS compositions of the present invention include North American PRRS virus isolates, Chinese PRRS virus strains, and European PRRS virus strains, as well as genetically modified versions of such isolates/strains. In one embodiment, the PRRS virus antigen component employed in the compositions according to the present invention is a North American PRRS virus.

In some embodiments, the PRRS virus antigen component employed in the compositions of this invention is the North American PRRS virus isolate designated P129 or a live, genetically modified version thereof. Preferably, the genetically modified PRRS virus is unable to produce a pathogenic infection yet is able to elicit an effective immunoprotective response against infection by the wild-type PRRS virus.

A genetically modified PRRS virus for use in the compositions of the invention can be produced from an infectious clone. The preparation of an infectious cDNA clone of the North American PRRS virus isolate designated P129 is described in U.S. Pat. No. 6,500,662 which is hereby incorporated fully by reference. The sequence of P129 cDNA is disclosed in Genbank Accession Number AF494042 and in U.S. Pat. No. 6,500,662.

In one embodiment, a PCV2b divergent/M. hyo combination vaccine is provided as a single-dose, 1-bottle vaccine. In another embodiment, a PCV2b divergent/M. hyo/PRRS virus combination vaccine is provided as a single-dose, 2-bottle vaccine. For example, in some embodiments, a PCV2b divergent/M. hyo combination is provided as a stable liquid composition in a first bottle and a PRRS virus is provided in a lyophilized state in a second bottle. In some embodiments, additional *porcine* antigens can be added to either the first or the second bottle.

In one embodiment, the PRRS virus component is provided as a lyophilized, genetically modified live virus. Prior to administration, the PCV2b divergent/M. hyo liquid from a first bottle can be used to re-hydrate the PRRS virus in a second bottle so that all three antigens can be administered to the animal in a single-dose.

Vaccines of the present invention can be formulated following accepted convention to include pharmaceutically acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, Corynebacterium parvum, Bacillus Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant (N,N-dioctadecyl-N',N'-bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM ½ formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution. In one embodiment, the SP-oil emulsion is present in the final composition in v/v amounts of about 1% to 25%, preferably about 2% to 15%, more preferably about 5% to 12% v/v.

Yet another example of a suitable adjuvant for use in the compositions of the invention is AMPHIGEN™ adjuvant which consists of de-oiled lecithin dissolved in an oil, usually light liquid paraffin.

Other examples of adjuvants useful in the compositions of the invention are the following proprietary adjuvants: Microsol Diluvac Forte® duel emulsion adjuvant system, Emunade adjuvant, and Xsolve adjuvant. Both the Emunade and Xsolve adjuvants are emulsions of light mineral oil in water, but Emunade also contains alhydrogel, and d,1-α-tocopheryl acetate is part of the XSolve adjuvant. A still further example of a suitable adjuvant for use in the compositions of the invention is ImpranFLEX™ adjuvant (a water-in-oil adjuvant). A still further example of a suitable adjuvant is a Carbomer (Carbopol®) based adjuvant. Preferred Carbopol® adjuvants include Carbopol® 934 polymer and Carbopol®941 polymer.

In one embodiment, the adjuvant or adjuvant mixture is added in an amount of about 100 μg to about 10 mg per dose. In another embodiment, the adjuvant/adjuvant mixture is added in an amount of about 200 μg to about 5 mg per dose. In yet another embodiment, the adjuvant/adjuvant mixture is added in an amount of about 300 μg to about 1 mg/dose.

The adjuvant or adjuvant mixture is typically present in the vaccine composition of the invention in v/v amounts of about 1% to 25%, preferably about 2% to 15%, more preferably about 5% to 12% v/v.

Other "immunomodulators" that can be included in the vaccine include, e.g., one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

The present invention also provides a method of immunizing a pig against a PCV2b divergent strain, the method including administering to the pig a composition according to the present invention, as described above. This composition for administration includes a PCV2b divergent ORF2 polypeptide, wherein the ORF2 polypeptide includes Leucine (L) at position 89, Threonine (T) at position 90, and Aspargine (N) at position 134, according to the numbering of SEQ ID NO: 1. As described above, this PCV2b divergent ORF2 polypeptide can further include at least one residue selected from the following: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment, the composition for administration includes a virus comprising and/or expressing the PCV2b divergent ORF2 polypeptide. In another embodiment, the composition for administration includes an isolated, recombinant PCV2b ORF2 polypeptide.

In one embodiment of the method of the present invention, the composition is administered intramuscularly, intradermally, transdermally, subcutaneously, or orally. In another embodiment, the composition is administered in a single dose. In yet another embodiment, the composition is administered as two doses.

In a further embodiment, the composition is administered to pigs having maternally-derived antibodies against PCV2.

In one embodiment, the composition is administered to pigs at 3 weeks of age or older.

Vaccine compositions according to the present invention can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions according to the present invention can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration), such as sterile suspensions or emulsions. Vaccine compositions according to the present invention may be administered as a spray, or mixed in food and/or water, or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired.

The present invention further provides a kit. This kit includes a bottle containing a vaccine composition according to the present invention for protecting pigs against a highly virulent *porcine circovirus* type 2b (PCV2b) divergent strain. This vaccine composition includes a PCV2b divergent ORF2 polypeptide, wherein the ORF2 polypeptide includes Leucine (L) at position 89, Threonine (T) at position 90, and Aspargine (N) at position 134, according to the numbering of SEQ ID NO: 1. As described above, this PCV2b divergent ORF2 polypeptide can further include at least one residue selected from the following: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215, according to the numbering of SEQ ID NO: 1.

In one embodiment of the kit, the vaccine composition is in the form of a virus comprising and/or expressing the PCV2b divergent ORF2 polypeptide. In another embodiment of the kit, the vaccine composition is in the form of an isolated, recombinant PCV2b divergent ORF2 polypeptide.

In one embodiment of the kit of the present invention, the vaccine composition in the bottle is provided as a ready-to-use liquid composition. In another embodiment of the kit, the vaccine composition in the bottle is provided in a lyophilized form. In a further embodiment, the kit can include a diluent. In yet another embodiment, the kit can further include an instruction manual which contains the information for administration of the vaccine composition.

Another aspect of the present invention provides methods of producing a vaccine composition which is in the form of an inactivated chimeric virus, wherein the chimeric virus includes an inactivated recombinant *porcine circovirus* type 1 that expresses a PCV2b divergent ORF2 polypeptide. Chimeric *porcine circoviruses* and methods for their preparation are described in WO 03/049703 A2, and also in U.S. Pat. Nos. 7,279,166 and 7,575,752. Methods of producing a chimeric *porcine circovirus* including an inactivated PCV1 that expresses a PCV2b divergent ORF2 polypeptide are described in Example 1 below. In one embodiment, the final composition is prepared by combining the inactivated cPCV1-2b virus with a suitable adjuvant and/or other pharmaceutically acceptable carrier.

A further aspect of the present invention provides methods of producing a vaccine composition which is in the form of an inactivated, PCV2b divergent whole virus that expresses PCV2b divergent ORF2 polypeptide. Such methods are described in Example 3 below. In one embodiment, the final composition is prepared by combining the inactivated PCV2B-DIV-MUT virus with a suitable adjuvant and/or other pharmaceutically acceptable carrier.

Yet another aspect of the present invention provides methods of producing recombinant PCV2 divergent ORF2 protein, i) by permitting infection of susceptible cells in culture with a recombinant viral vector containing PCV2 divergent ORF2 DNA coding sequences, wherein ORF2 protein is expressed by the recombinant viral vector, and ii) thereafter recovering the ORF2 protein in the supernatant. Typically, high amounts of PCV2 divergent ORF2 protein can be recovered in the supernatant. High amounts of PCV2 divergent ORF2 means more than about 20 μg/mL supernate, preferably more than about 25 μg/mL, even more preferred more than about 30 μg/mL, even more preferred more than about 40 μg/mL, even more preferred more than about 50 μg/mL, even more preferred more than about 60 μg/mL, even more preferred more than about 80 μg/mL, even more preferred more than about 100 μg/mL, even more preferred than about 150 μg/mL, most preferred than about 190 μg/mL.

Preferred cell cultures have a cell count between about $0.3$-$2.0 \times 10^6$ cells/mL, more preferably from about $0.35$-$1.9 \times 10^6$ cells/mL, still more preferably from about $0.4$-$1.8 \times 10^6$ cells/mL, even more preferably from about $0.45$-$1.7 \times 10^6$ cells/mL, and most preferably from about $0.5$-$1.5 \times 10^6$ cells/mL. Preferred cells are determinable by those of skill in the art. Preferred cells are those susceptible for infection with an appropriate recombinant viral vector, containing a PCV2 divergent ORF2 DNA and expressing the PCV2 divergent ORF2 protein. Preferably the cells are insect cells, and more preferably, they include the insect cells sold under the trademark Sf+ insect cells (Protein Sciences Corporation, Meriden, Conn.).

Appropriate growth media will also be determinable by those of skill in the art with a preferred growth media being serum-free insect cell media such as Excell 420 (JRH Biosciences, Inc., Lenexa, Kans.) and the like. Preferred viral vectors include baculovirus such as BaculoGold (BD Biosciences Pharmingen, San Diego, Calif.), in particular if the production cells are insect cells. Although the baculovirus expression system is preferred, it is understood by those of skill in the art that other expression systems will work for purposes of the present invention, namely the expression of PCV2 divergent ORF2 into the supernatant of a cell culture. Such other expression systems may require the use of a signal sequence in order to cause ORF2 expression into the media. However, when ORF2 is produced by a baculovirus expression system, then typically it does not require any signal sequence or further modification to cause expression of ORF2 into the media. It is believed that this protein can independently form virus-like particles (Journal of General Virology 2000, Vol. 81, pp. 2281-2287), and be secreted into the culture supernatant. The recombinant viral vector containing the PCV2 divergent ORF2 DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of $0.35$-$1.9 \times 10^6$ cells/mL, still more preferably of about $0.4$-$1.8 \times 10^6$ cells/mL, even more preferably of about $0.45$-$1.7 \times 10^6$ cells/mL, and most preferably of about $0.5$-$1.5 \times 10^6$ cells/mL with a recombinant viral vector containing a PCV2 divergent ORF2 DNA and expressing the PCV2 divergent ORF protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the Sf+ cells are observed following inoculation for characteristic baculovirus-induced changes. Such observation may include monitoring cell density trends and the decrease in viability during the post-infection period. Peak viral titer is typically observed 3-5 days after infection, and peak ORF2 release from the cells into the supernatant is typically obtained between days 5 and 8, and/or when cell viability decreases to less than 10%.

The recovery process preferably begins with the separation of cell debris from the expressed PCV2 divergent ORF2 polypeptide in media via a separation step. Preferred separation steps include filtration, centrifugation at speeds up to about 20,000×g, continuous flow centrifugation, chromatographic separation using ion exchange or gel filtration, and conventional immunoaffinity methods. Those methods are known to persons skilled in the art (e.g. Harris and Angel (eds.), Protein purification methods—a practical approach, IRL press Oxford 1995). Preferred filtration methods include dead-end microfiltration and tangential flow (or cross flow) filtration, including hollow fiber filtration. Of these, dead-end microfiltration is preferred. Preferred pore sizes for dead-end microfiltration are between about 0.30-1.35 μm, more preferably between about 0.35-1.25 μm, still more preferably between about 0.40-1.10 μm, and most preferably between about 0.45-1.0 μm.

For recovery of recombinant PCV2 divergent ORF2 polypeptide that will be used in an immunogenic or immunological composition such as a vaccine, the inclusion of an inactivation step is preferred in order to inactivate the viral vector. Preferably, this inactivation is done either just before or just after the filtration step, with after the filtration step being the preferred time for inactivation. Any conventional inactivation method can be used for purposes of the present invention. Thus, inactivation can be performed by chemical and/or physical treatments. In preferred forms, the volume of harvest fluids is determined and the temperature is brought to between about 32-42° C., more preferably between about 34-40° C., and most preferably between about 35-39° C. Preferred inactivation methods include the addition cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyleneamine hydrobromide, preferably of about 0.4M, which has been cyclized to 0.2M binary ethylenimine (BEI) in 0.3N NaOH, to the fluids to give a final concentration of about 5 mM BEI. Preferably, the fluids are then stirred continuously for 72-96 hours, and the inactivated harvest fluids can be stored frozen at −40° C. or below or between about 1-7° C. After inactivation is completed, a sodium thiosulfate solution, preferably at 1.0M, is added to neutralize any residual BEI. Preferably, the sodium thiosulfate is added in equivalent amount as compared to the BEI added prior to for inactivation. For example, in the event BEI is added to a final concentration of 5 mM, a 1.0 M sodium thiosulfate solution is added to give a final minimum concentration of 5 mM to neutralize any residual BEI.

A further aspect of the present invention relates to a method for preparing a composition comprising PCV2 divergent ORF2 protein, and inactivated viral vector. This method includes the steps: i) cloning the amplified PCV2 divergent ORF2 gene into a transfer vector; ii) transfecting the portion of the transfer vector containing the recombinant PCV2 divergent ORF2 gene into a virus; iii) infecting cells in media with the transfected viral vector; iv) causing the transfected viral vector to express the PCV2 divergent ORF2 recombinant protein from PCV2 divergent ORF2 gene; v) separating cells from the supernatant; vi) recovering the expressed PCV2 divergent ORF2 protein from the supernatant; and vii) inactivating the recombinant viral vector. Preferably, the recombinant viral vector is a baculovirus-containing ORF2 DNA coding sequences, and the cells are Sf+ cells. Preferred separation steps are those described above, most preferred is the filtration step. Preferred inactivation steps are those described above. Preferably, inactivation is performed between about 35-39° C. and in the presence of 2 to 8 mM BEI, still more preferred in the presence of about 5 mM BEI. Preferably, inactivation is performed for at least 24 hours, even more preferred for 24 to 72 hours.

According to a further aspect, the method for preparing a composition comprising PCV2 divergent ORF2 protein, and inactivated viral vector, as described above, also includes an neutralization step after step vii). This step viii) comprises adding of an equivalent amount of an agent that neutralizes the inactivation agent within the solution. Preferably, if the inactivation agent is BEI, addition of sodium thiosulfate to an equivalent amount is preferred. Thus, according to a further aspect, step viii) comprises adding of a sodium thiosulfate solution to a final concentration of about 1 to about 20 mM, preferably of about 2 to about 10 mM, still more preferably of about 2 to about 8 mM, still more preferably of about 3 to about 7 mM, most preferably of about 5 mM, when the inactivation agent is BEI.

In another aspect of the present invention, a method for preparing a composition, preferably an antigenic composition, such as for example a vaccine, for invoking an immune response against a PCV2 divergent strain is provided. Generally, this method includes the steps of transfecting a construct into a virus, wherein the construct comprises i) recombinant DNA from ORF2 of a PCV2 divergent strain, ii) infecting cells in growth media with the transfected virus, iii) causing the virus to express the recombinant protein from PCV2 divergent ORF2, iv) recovering the expressed ORF2 protein from the supernatant, v) and preparing the composition by combining the recovered protein with a suitable adjuvant and/or other pharmaceutically acceptable carrier.

The following examples set forth preferred materials and procedures in accordance with the present invention. However, it is to be understood that these examples are provided by way of illustration only, and nothing therein should be deemed a limitation upon the overall scope of the invention.

Example 1: Chimeric *Porcine Circovirus* (cPCV)1-2 Production Methods

The cPCV1-2 is constructed by cloning the immunogenic capsid gene of a pathogenic *porcine circovirus* type 2b divergent strain (termed "PCV2B-DIV-MUT") into the genomic backbone of the nonpathogenic *porcine circovirus* type 1 (PCV1). The procedure for construction of the chimeric DNA clone is described, for example, in U.S. Pat. No. 7,279,166, which is incorporated herein by reference in its entirety. An infectious stock of the chimeric virus is used to infect *Porcine* Kidney (PK)-15 cells grown in Minimum Essential Medium (MEM) supplemented with 0.05% lactalbumin hydrolysate (LAH), 30 μg/mL gentamicin sulfate, and 5% fetal bovine serum. The resulting cPCV1-2 infected PK-15 cells is further expanded by serial passing four more times using the same growth medium, except with 2-3% fetal bovine serum. The fifth passage is frozen, thawed and filtered, and the resulting lysates are used to prepare a pre-master seed and subsequent master seed.

The medium which is used for producing virus seeds is the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 μg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 μg/mL gentamicin. Up to 5 g/L glucose and up to 5 mmol/L L-glutamine can be added to the growth medium and/or the virus propagation medium as required to sustain the cells.

The cPCV1-2 master seed virus are added to a cell suspension of PK-15 cells and adsorbed for up to 3 hours. Seed virus is diluted in growth basal medium to provide a multiplicity of infection (MOI) of 0.1 to 0.2.

Cultures of PK-15 cells are initially inoculated with working seed virus at the time of cell planting, or when cells reach approximately 20% to 50% confluency. This initial passage may be referred as "One-Step Infection Method" for the production of antigen stock, or may be further used for serial passages. For serial passages, the cPCV1-2 infected PK-15 cells are further expanded up to passage 7 by serial splits at the ratio of 1:5-20 for virus propagation. Culture medium containing an infected cell suspension from the previous passage can serve as seed material for the next passage. The cPCV1-2 infected cells are incubated for three (3) to 14 days for each passage at 36±2° C. when cells reach ≥90% confluency. The cPCV1-2 virus causes observable cytopathic changes during viral replication. At harvest, rounding of cells and considerable floating debris is observed. Cultures are also observed for visual evidence of bacterial or fungal contamination. The incubation time between harvests for the cPCV antigen is provided in Table 1 below:

TABLE 1

Minimum and Maximum Times for Harvesting cPCV Antigen

| Method | Minimum/ Maximum Time | Temperature Range |
|---|---|---|
| One-Step Infection | 5 to 16 days | 36 ± 2° C. |
| Serial Passage (MSV + 1 to MSV + 4) | 16 to 36 Days | 36 ± 2° C. |

The cPCV1-2 culture fluids are harvested into sterile vessels and are sampled for mycoplasmal contamination using known methods. Multiple harvests may be conducted from roller bottles, bioreactors and perfusion vessels.

Prior to inactivation of the harvested cPCV1-2 virus, one or more antigen lots may be concentrated (e.g., up to 60×) by ultrafiltration. The concentrates may be washed with balanced salt solution to reduce serum proteins.

The method of inactivation, attenuation, or detoxification of the cPCV1-2 virus will now be described. After cPCV antigen concentration, β-propiolactone (BPL) is added to the pooled cPCV1-2 viral material to obtain an approximate concentration of 0.2% v/v. The pooled viral fluids are then agitated for a minimum of 15 minutes and then the inactivating bulk antigen fluids are transferred to a second sterile vessel. The transferred antigen fluids are maintained at 2-7° C., with constant agitation, for a minimum of 24 hours. After a minimum of 24 hours, a second addition of 0.2% v/v of BPL is added to the pooled suspension. The contents are subsequently agitated, transferred to a third vessel, and maintained at 2-7° C., with constant agitation, for an additional time of not less than 84 hours. In general, the total inactivation time is not less than 108 hours and not more than 120 hours. The inactivation method is summarized in Table 2 below.

TABLE 2

Inactivation Method

| Inactivant | Final Concentration | Temp. Range | Time-Hours (Min/Max) |
|---|---|---|---|
| β-propiolactone (BPL) | 0.4% v/v (2 × 0.2% v/v additions) | 2-7° C. (w/Agitation) | 108-120 |

The inactivation is terminated by the addition of a final concentration of not more than 0.1 M solution of sodium thiosulfate. The pH of the inactivated antigen stock is adjusted to about 6.8 using NaOH or HCl. Following inactivation, a representative sample is taken from the pool and tested for completion of inactivation. The inactivated cPCV1-2 antigen product is standardized to a meet a target of greater than 1.0 RP as measured via potency ELISA. In one embodiment, the final composition is prepared by combining the inactivated cPCV1-2b virus with a suitable adjuvant and/or other pharmaceutically acceptable carrier.

Example 2: Methods of Producing Recombinant PCV2b Divergent Capsid Protein

Production of the subunit vaccine is the result of a two phase process: firstly, the production of the ORF2 subunit antigen in the baculovirus expression system and secondly, the formulation/manufacturing of the final product. For the initial steps (the construction of the recombinant baculovirus and the production of the ORF2 antigen), the basic technology process used will now be described. A baculovirus expression system is used for expression of the ORF2 gene from a PCV2b divergent strain. The recombinant baculovirus containing the PCV2 ORF2 gene is generated as follows: viral DNA is isolated from PK-15 cells infected with the PCV2b divergent strain identified herein as "PCV2B-DIV-MUT". The ORF2 gene from this PCV2b divergent strain is PCR amplified to contain a 5' Kozak's sequence (ccgccatg) and a 3' EcoR1 site (gaattc), and is cloned into the pGEM-T-Easy vector (Promega, Madison, Wis.). Then, it is subsequently excised and subcloned into the transfer vector pVL1392 (BD Biosciences Pharmingen, San Diego, Calif.). The pVL1392 plasmid containing the PCV2b divergent ORF2 gene is then co-transfected with BaculoGold®. (BD Biosciences Pharmingen) baculovirus DNA into Spodoptera frugiperda (Sf+) insect cells (Protein Sciences, Meriden, Conn.) to generate the recombinant baculovirus containing the PCV2b divergent ORF2 gene. The recombinant baculovirus containing this PCV2b divergent ORF2 gene is plaque-purified and Master Seed Virus (MSV) is propagated on the SF+ cell line, aliquoted, and stored at −70° C. The MSV is positively identified as PCV2 ORF2 baculovirus by PCR-RFLP using baculovirus-specific primers. Insect cells infected with PCV2 ORF2 baculovirus to generate MSV or Working Seed Virus express the PCV2 ORF2 antigen. Expression of the ORF2 gene of PCV2B-DIV-MUT is confirmed by an immunoassay using hyperimmune serum raised against PCV2B-DIV-MUT in rabbits, or monoclonal antibodies, in an indirect fluorescent antibody assay. Alternatively, expression of the ORF2 gene of PCV2B-DIV-MUT is confirmed by an immunoassay using an antibody raised against classical PCV2a or PCV2b that cross reacts with the PCV2b divergent strain. Additionally, the identity of the PCV2b divergent ORF2 baculovirus is confirmed by N-terminal amino acid sequencing. The PCV2b divergent ORF2 baculovirus MSV is also tested for purity in accordance with 9 C.F.R. 113.27 (c), 113.28, and 113.55.

The recombinant viral vector containing the PCV2 ORF2 DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably, the method described herein comprises the infection of $0.35\text{-}1.9 \times 10^6$ cells/mL, still more preferably of about $0.4\text{-}1.8 \times 10^6$ cells/mL, even more preferably of about $0.45\text{-}1.7 \times 10^6$ cells/mL, and most preferably of about $0.5\text{-}1.5 \times 10^6$ cells/mL with a recombinant viral vector containing a PCV2 ORF2 DNA and expressing the PCV2 ORF protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the Sf+ cells are observed following inoculation for characteristic baculovirus-induced changes. Such observation may include monitoring cell density trends and the decrease in viability during the post-infection period. A peak viral titer is typically observed 3-5 days after infection and peak ORF2 release from the cells into the supernatant is typically obtained between days 5 and 8, and/or when cell viability decreases to less than 10%.

In one embodiment, a 1000 mL spinner flask is seeded with approximately $1.0 \times 10^6$ Sf+ cells/ml in 300 mL of Excell 420 media. The flask is then incubated at 27° C. and agitated at 100 rpm. Subsequently, the flask is seeded with PCV2b divergent ORF2/Bac (recombinant baculovirus containing the PCV2b divergent ORF2 gene) virus seed with a 0.1 MOI after 24 hours of incubation.

The flask is then incubated at 27° C. for a total of 6 days. After incubation, the contents of the flask are centrifuged, and the resulting supernatant is harvested, microfiltered through a 0.45-1.0 µm pore size membrane, and then inactivated. The supernatant is inactivated by bringing its temperature to 37+/−2° C., and adding 10 mM binary ethylenimine (BEI) to the supernatant. The supernatant is then stirred continuously for 48 hrs. A 1.0 M sodium thiosulfate solution to give a final minimum concentration of 5 mM is added to neutralize any residual BEI. The quantity of ORF2 in the neutralized supernatant is then quantified using an ELISA assay procedure such as the one described in Example 1 of U.S. Pat. No. 7,700,285 to Eichmeyer et al. The detection antibody used is a monoclonal antibody to PCV2b divergent ORF2 capsid protein.

The present invention is scalable from small scale production of recombinant PCV2b divergent ORF2 to large scale production of recombinant PCV2b divergent ORF2.

The second phase of the vaccine production is the formulation/manufacturing of the final product. The blending strategy is based on: a) a fixed antigen content per dose, and b) a fixed amount of at least one adjuvant. In one embodiment, the pharmaceutical form of the finished product is equivalent to an oil-in-water emulsion. In order to prepare the final vaccine, the adjuvant is added to the antigenic fraction and stirred until a homogeneous emulsion is obtained. Evidence is provided of satisfactory homogeneity. To ensure that a batch of vaccine will lead to the claimed efficacy, its relative potency is determined by an in vivo assay which has been validated. Based on the analysis performed, the potency test is able to detect sub-potent batches.

Example 3: Methods of Producing Inactivated PCV2b Divergent Whole Virus

An infectious stock of the PCV2b divergent virus: PCV2B-DIV-MUT is used to infect *Porcine* Kidney (PK)-15 cells grown in Minimum Essential Medium (MEM), supplemented with 0.05% lactalbumin hydrolysate (LAH), 30 µg/mL gentamicin sulfate, and 5% fetal bovine serum. The resulting PCV2B-DIV-MUT infected PK-15 cells are further expanded by serial passing four more times using the same growth medium, except with 0.5-3% fetal bovine serum. The fifth passage is frozen, thawed and filtered, and the resulting lysates are used to prepare a pre-master seed and subsequent master seed.

The medium which is used for producing virus seeds is the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 µg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 µg/mL gentamicin. Up to 5 g/L glucose and up to 5 mmol/L L-glutamine can be added to the growth medium and/or the virus propagation medium, as required to sustain the cells.

The PCV2B-DIV-MUT master seed virus is added to a cell suspension of PK-15 cells and adsorbed for up to 3 hours. Seed virus is diluted in growth basal medium to provide a multiplicity of infection (MOI) of 0.1-0.2.

Cultures of PK-15 cells are initially inoculated with working seed virus at the time of cell planting, or when cells reach approximately 20% to 50% confluency. This initial passage may be referred as "One-Step Infection Method" for the production of antigen stock, or may be further used for serial passages. For serial passages, the infected PCV2B-DIV-MUT PK-15 cells are further expanded up to passage 7 by serial splits at the ratio of 1:5-20 for virus propagation. Culture medium containing an infected cell suspension from the previous passage can serve as seed material for the next passage. The PCV2B-DIV-MUT infected cells are incubated for three (3) to 14 days for each passage at 36±2° C. when cells reach ≥90% confluency. The PCV2B-DIV-MUT virus can cause observable cytopathic changes during viral replication. At harvest, rounding of cells and considerable floating debris is observed. Cultures are also observed for visual evidence of bacterial or fungal contamination. The incubation times between harvests for the PCV2B-DIV-MUT antigen are the same as those provided in Table 1 above.

The PCV2B-DIV-MUT culture fluids are harvested into sterile vessels, and are sampled for mycoplasmal contamination using known methods. Multiple harvests may be conducted from roller bottles, bioreactors and perfusion vessels.

Prior to inactivation of the harvested PCV2B-DIV-MUT virus, one or more antigen lots may be concentrated (e.g., up to 60×) by ultrafiltration. The concentrates may be washed with balanced salt solution to reduce serum proteins.

The method of inactivation, attenuation, or detoxification of the PCV2B-DIV-MUT virus is the same as that described in Example 1 and Table 2 above. The inactivation is terminated by the addition of a final concentration of not more than 0.1 M solution of sodium thiosulfate. The pH of the inactivated antigen stock is adjusted to about 6.8 using NaOH or HCl. Following inactivation, a representative sample is taken from the pool and tested for completion of inactivation. The inactivated PCV2B-DIV-MUT antigen product is standardized to a meet a target of greater than 1.0 RP, as measured via potency ELISA. In one embodiment, the final composition is prepared by combining the inactivated PCV2B-DIV-MUT virus with a suitable adjuvant and/or other pharmaceutically acceptable carrier.

Example 4: PCV2b Proof of Principle Study

The objective of the study was to assess a PCV2b divergent candidate vaccine for homologous and heterologous protection. The study design is outlined in Table 3. The IVP for T04, T08 and T12 consisted of a killed PCV2b-divergent virus, adjuvanted with 10% SP-Oil. The IVP for T02, T06 and T10 consisted of a killed chimeric PCV1:2a virus, adjuvanted with 10% SP-Oil. The IVP for T03, T07 and T11 consisted of a killed chimeric PCV1:2b virus, adjuvanted with 10% SP-Oil.

TABLE 3

Proof of Principle Study Design

| Group | N | Investigational Veterinary Product (IVP) | Vaccinations | Challenge Day | Strain | Dose, Route | Necropsy |
|---|---|---|---|---|---|---|---|
| T01 | 10 | Placebo | Day 0 (~3 wks of age) 2 mL IM Left side of neck | Day 21 (~6 wks of age) | PCV2b | 1 mL/IM 2 mL/IN | Necropsy (~9 wks of age) and Tissue Collection |
| T02 | 10 | Chimeric PCV1:PCV2a | | | | | |
| T03 | 10 | Chimeric PCV1:PCV2b | | | | | |
| T04 | 10 | Killed PCV2b-Divergent | | | | | |
| T05 | 10 | Placebo | | | PCV2a | | |
| T06 | 10 | Chimeric PCV1:PCV2a | | | | | |
| T07 | 10 | Chimeric PCV1:PCV2b | | | | | |
| T08 | 10 | Killed PCV2b-Divergent | | | | | |
| T09 | 10 | Placebo | | | PCV2b-Divergent | | |
| T10 | 10 | Chimeric PCV1:PCV2a | | | | | |
| T11 | 10 | Chimeric PCV1:PCV2b | | | | | |
| T12 | 10 | Killed PCV2b-Divergent | | | | | |

Pigs were between 3 and 4 weeks of age on Day 0 for vaccination. A single dose of 2 mL of the assigned vaccine was administered intramuscularly (IM) into the right side of the neck. A single 3 mL sterile syringe with 1" or ¾" needle was used for each pig. Vaccination details were recorded. Pigs were observed within 1 hour (±30 minutes) after each vaccination for abnormal clinical signs, including but not limited to: lethargy, labored breathing, vomiting, and incoordination. Any observed clinical signs were documented on the general health form. A veterinarian was notified to follow up on two pigs which presented with signs of overall poor condition and declining health. Those animals were humanely euthanized.

Challenge was conducted on Day 21, when the pigs are about 6-7 weeks of age. Each pig was inoculated with a total 3 mL of respective challenge virus, pre-diluted to 4.8-5.8 log 10 TCID50/mL, with 1 mL administered intranasally (IN) in each nostril, and 1 mL administered intramuscularly (IM). A reserved aliquot of the challenge viruses was titrated following the challenge to confirm the actual challenge dose.

Individual blood samples (5-10 mL) were collected in serum separator tubes (SST) on Day −1 (prior to vaccination), and Days 7, 14, 20/21, 28, 35, and 42. Samples were aliquoted and stored at ≤−65° C., and later tested for PCV2 antibody titers by ELISA, and PCV2 viremia by qPCR.

The primary outcomes were the homologous and heterologous protection of a candidate vaccine when compared to the placebo. The primary variable was viremia, and the secondary variables were fecal shedding and histopathological lesions.

The results indicated that pigs remained negative for PCV2 viremia and fecal shed prior to challenge, as indicated in Tables 4 and 5. Throughout the study, however, all pigs in all treatment groups became positive at some point for PCV2, as assessed by quantitative PCR for PCV2 viremia (Table 4) and PCV2 fecal shedding (Table 5).

TABLE 4

PCV2 Viremia

| | | Time Point (Geometric LS Mean DNA Copies) | | | | | | |
|---|---|---|---|---|---|---|---|---|
| | | Pre-challenge | | | | Post-challenge | | |
| Trt | Challenge | Day −2 | Day 7 | Day 14 | Day 20 | Day 28 | Day 35 | Day 42 |
| T01 | PCV2b | 0 | 0 | 0 | 0 | 30421 | 280798 | 5184 |
| T02 | PCV2b | 0 | 0 | 0 | 0 | 1866 | 22 | 2 |
| T03 | PCV2b | 0 | 0 | 0 | 0 | 3870 | 238 | 10 |
| T04 | PCV2b | 0 | 0 | 0 | 0 | 615 | 66 | 6 |
| T05 | PCV2a | 0 | 0 | 0 | 0 | 10927 | 22982 | 1906 |
| T06 | PCV2a | 0 | 0 | 0 | 0 | 43 | 2 | 2 |
| T07 | PCV2a | 0 | 0 | 0 | 0 | 25991 | 211465 | 189 |
| T08 | PCV2a | 0 | 0 | 0 | 0 | 309 | 20 | 6 |
| T09 | PCV2b-Divergent | 0 | 0 | 0 | 0 | 413 | 384933 | 50683 |
| T10 | PCV2b-Divergent | 0 | 0 | 0 | 0 | 7 | 314 | 65 |
| T11 | PCV2b-Divergent | 0 | 0 | 0 | 0 | 406 | 427073 | 40711 |
| T12 | PCV2b-Divergent | 0 | 0 | 0 | 0 | 189 | 3315 | 9 |

Individual fecal swabs were also taken from each pig prior to challenge (Day 20/21), and weekly post-challenge. Individual sterile polyester swabs were used for collecting fecal swab, and placed in a tube containing 3 mL sterile PBS medium. Swabs were swirled for 5 seconds in the medium before discarded. Samples were aliquoted and stored at ≤−65° C. The fecal swab samples were tested for virus shedding by standard quantitative PCR procedure.

During necropsy, sections of tracheobronchial, mesentery and superficial inguinal lymph nodes, and tonsil tissues were also collected in duplicate for each pig, individually identified, and fixed in 10% buffered formalin. One set was archived, while the other was submitted for standard histopathology examination for lymphoid depletion (PCVAD), and histiocytic replacement. The conclusion was recorded as Yes (+) or No (−). A pig was considered having lymphoid depletion or histiocytic replacement if one or more tissues were scored "+". In addition, the tissues were also tested for PCV2 antigen by IHC. The results were recorded as 0 (no staining) and 1-3 (different levels of staining) A score 0 was considered as PCV2 IHC (−), and a score of 1 or higher was considered as PCV2 IHC (+). A pig was considered IHC (+) if one or more tissues were IHC (+).

TABLE 5

PCV2 fecal shedding

| | | Time Point (Geometric LS Mean DNA Copies) | | | |
|---|---|---|---|---|---|
| | | Pre-challenge | Post-challenge | | |
| Trt | Challenge | Day 20 | Day 28 | Day 35 | Day 42 |
| T01 | PCV2b | 0 | 257 | 24822 | 106798 |
| T02 | PCV2b | 0 | 7 | 7 | 0 |
| T03 | PCV2b | 0 | 450 | 140 | 111 |
| T04 | PCV2b | 0 | 43 | 288 | 16 |
| T05 | PCV2a | 0 | 184 | 4130 | 23485 |
| T06 | PCV2a | 0 | 0 | 16 | 2 |
| T07 | PCV2a | 0 | 866 | 10072 | 6477 |
| T08 | PCV2a | 0 | 387 | 73 | 20 |
| T09 | PCV2b-Divergent | 0 | 1007 | 199324 | 89204 |
| T10 | PCV2b-Divergent | 0 | 881 | 1880 | 65 |
| T11 | PCV2b-Divergent | 0 | 58519 | 480005 | 219127 |
| T12 | PCV2b-Divergent | 0 | 65 | 541 | 541 |

Pre-challenge titers, as measured by PCV2 ELISA, indicated that the least square (LS) mean titers of all treatment groups were PCV2 antibody negative (Table 6). PCV2 ELISA antibody titers >0.5 are considered to be PCV2 antibody positive.

TABLE 6

PCV2 ELISA

| Trt | Challenge | Day −2 | Day 7 | Day 14 | Day 20 | Day 28 | Day 35 | Day 42 |
|---|---|---|---|---|---|---|---|---|
| T01 | PCV2b | 0.1673 | 0.2741 | 0.1245 | 0.0241 | 0.0223 | 0.0995 | 0.3663 |
| T02 | PCV2b | 0.1828 | 0.2934 | 0.1640 | 0.0644 | 0.3926 | 0.6212 | 0.5712 |
| T03 | PCV2b | 0.1628 | 0.2783 | 0.1700 | 0.0183 | 0.0434 | 0.1833 | 0.2481 |

TABLE 6-continued

| | | PCV2 ELISA | | | | | | |
|---|---|---|---|---|---|---|---|---|
| Trt | Challenge | Day −2 | Day 7 | Day 14 | Day 20 | Day 28 | Day 35 | Day 42 |
| T04 | PCV2b | 0.1673 | 0.2593 | 0.1088 | 0.0278 | 0.1635 | 0.3956 | 0.3491 |
| T05 | PCV2a | 0.2316 | 0.4322 | 0.2580 | 0.0320 | 0.0256 | 0.2396 | 0.3511 |
| T06 | PCV2a | 0.1970 | 0.3726 | 0.2357 | 0.0887 | 0.4316 | 0.5458 | 0.4569 |
| T07 | PCV2a | 0.2582 | 0.3787 | 0.2079 | 0.0399 | 0.0914 | 0.3066 | 0.4831 |
| T08 | PCV2a | 0.1940 | 0.3437 | 0.2012 | 0.0357 | 0.2637 | 0.4717 | 0.4526 |
| T09 | PCV2b-Divergent | 0.1334 | 0.2283 | 0.1603 | 0.0070 | 0.0102 | 0.0989 | 0.2374 |
| T10 | PCV2b-Divergent | 0.1593 | 0.2071 | 0.1400 | 0.0518 | 0.4015 | 0.6827 | 0.6433 |
| T11 | PCV2b-Divergent | 0.1752 | 0.2484 | 0.1340 | 0.0252 | 0.0807 | 0.2255 | 0.3105 |
| T12 | PCV2b-Divergent | 0.1652 | 0.3035 | 0.1669 | 0.0270 | 0.2632 | 0.4868 | 0.4604 |

The experimental PCV2b divergent vaccine treatment (T04, T08, and T12) numerically reduced PCV2 viremia (Table 4) and fecal shed (Table 5). It also led to a decrease in histopathological lesions at most of the time points when compared to placebo, as demonstrated by immunohistochemistry (IHC) scores (Table 7), and lymphoid depletion scores (Table 8). Following challenge, a moderate anamnestic response in PCV2 ELISA antibody titers was observed in all challenge groups (Table 6), potentially suggesting that vaccine antigen dose needed further optimization. Although statistical comparisons were not made in this study, it is evident that the PCV2b divergent vaccine treatment afforded protection against the PCV2a, PCV2b, and PCV2b-Divergent challenge strains.

In assessing PCV2 vaccine efficacy, viremia and lymphoid depletion are considered by many to be the key parameters to measure. In this study, it is important to note that the PCV2b divergent vaccine performed numerically better against PCV2b divergent challenge than did either the PCV2a or PCV2b vaccines.

TABLE 7

| | | Immunohistochemistry (IHC) scores | | | | |
|---|---|---|---|---|---|---|
| | | Ever Abnormal? | | | | Total |
| | | No | | Yes | | Observations |
| Trt | Challenge | # | % | # | % | # |
| T01 | PCV2b | 2 | 22.2 | 7 | 77.8 | 9 |
| T02 | PCV2b | 6 | 66.7 | 3 | 33.3 | 9 |
| T03 | PCV2b | 4 | 50.0 | 4 | 50.0 | 8 |
| T04 | PCV2b | 8 | 80.0 | 2 | 20.0 | 10 |
| T05 | PCV2a | 3 | 30.0 | 7 | 70.0 | 10 |
| T06 | PCV2a | 6 | 60.0 | 4 | 40.0 | 10 |
| T07 | PCV2a | 4 | 44.4 | 5 | 5506 | 9 |
| T08 | PCV2a | 7 | 70.0 | 3 | 30.0 | 10 |
| T09 | PCV2b-Divergent | 4 | 40.0 | 6 | 60.0 | 10 |
| T10 | PCV2b-Divergent | 9 | 100.0 | 0 | 0.0 | 9 |
| T11 | PCV2b-Divergent | 2 | 22.2 | 7 | 77.8 | 9 |
| T12 | PCV2b-Divergent | 7 | 77.8 | 2 | 22.2 | 9 |

TABLE 8

| | | Lymphoid depletion scores | | | | |
|---|---|---|---|---|---|---|
| | | Ever Abnormal? | | | | Total |
| | | No | | Yes | | Observations |
| Trt | Challenge | # | % | # | % | # |
| T01 | PCV2b | 3 | 33.3 | 6 | 66.7 | 9 |
| T02 | PCV2b | 7 | 77.82 | 2 | 22.2 | 9 |
| T03 | PCV2b | 7 | 87.5 | 1 | 12.5 | 8 |
| T04 | PCV2b | 8 | 80.0 | 2 | 20.0 | 10 |
| T05 | PCV2a | 4 | 40.0 | 6 | 60.0 | 10 |
| T06 | PCV2a | 10 | 100.0 | 0 | 0 | 10 |
| T07 | PCV2a | 6 | 66.7 | 3 | 33.3 | 9 |
| T08 | PCV2a | 7 | 70.0 | 3 | 30.0 | 9 |
| T09 | PCV2b-Divergent | 5 | 50.0 | 5 | 50.0 | 10 |
| T10 | PCV2b-Divergent | 7 | 77.8 | 2 | 22.2 | 9 |
| T11 | PCV2b-Divergent | 5 | 55.6 | 4 | 44.4 | 9 |
| T12 | PCV2b-Divergent | 8 | 88.9 | 1 | 11.1 | 9 |

Example 5: PCV2b Challenge Model Optimization Study

The objective of this study was to assess PCV2b challenge material titrations, and route of administration. In addition, a preliminary assessment of a new PCV2b divergent challenge preparation was conducted alongside current validated PCV2a and PCV2b challenge models. An outline of the study design is shown in Table 9.

TABLE 9

| | | PCV2b Challenge Model Optimization Study Design | | |
|---|---|---|---|---|
| | | Challenge | | |
| Group | N | Strain | Titration | Dose, Route | Necropsy |
| T01 | 12 | PCV2b | 4.7 log/3 mL | 1 mL/IM 2 mL/IN | Necropsy (~9 wks of age) and Tissue Collection |
| T02 | 12 | | 5.4 log/3 mL | 1 mL/IM 2 mL/IN | |
| T03 | 12 | | 6.1 log/3 mL | 1 mL/IM 2 mL/IN | |
| T04 | 12 | | 5.4 log/3 mL | 3 mL/IN | |
| T05 | 12 | PCV2a | 4.45 log/3 mL | 1 mL/IM 2 mL/IN | |
| T06 | 12 | | 5.15 log/3 mL | 1 mL/IM 2 mL/IN | |
| T07 | 12 | | 5.85 log/3 mL | 1 mL/IM 2 mL/IN | |
| T08 | 12 | | 5.15 log/3 mL | 3 mL/IN | |
| T09 | 12 | PCV2b-Divergent | 4.38 log/3 mL | 1 mL/IM 2 mL/IN | |
| T10 | 12 | | 5.08 log/3 mL | 1 mL/IM 2 mL/IN | |

TABLE 9-continued

PCV2b Challenge Model Optimization Study Design

| Group | N | Challenge Strain | Titration | Dose, Route | Necropsy |
|---|---|---|---|---|---|
| T11 | 12 | | 5.78 log/3 mL | 1 mL/IM 2 mL/IN | |
| T12 | 12 | | 5.08 log/3 mL | 3 mL/IN | |

Crossbred pigs, approximately 6 weeks of age at Day 0, with low to negative serum antibody to PCV2, and PCV2 viremia-free, were placed in assigned pens/rooms in a BSL-2 facility with separate air spaces. There were 4 pens in each of the 3 rooms, with 12 pigs per pen. Pigs remained in the assigned pens throughout the study. Pigs had ad libitum access to water, and a non-medicated age-appropriate complete ration throughout the study. All pigs were allowed to acclimate for a minimum of 3 days.

Challenge was conducted on Day 0, when the pigs are about 6 weeks of age. Each pig was inoculated with a total of 3 mL of respective challenge virus, pre-diluted to 4.0-6.0+/−0.5 log 10 TCID50/mL, with 2 mL administered intranasally (IN) in each nostril and 1 mL intramuscularly (IM), or 3 mL IN, depending on the treatment group. A reserved aliquot of the challenge viruses was titrated following the challenge to confirm the actual challenge dose.

Individual blood samples (5-10 mL) were collected in serum separator tubes (SST) at Day−21, Day−1 (prior to vaccination), and Days 7, 14, and 21. Samples were aliquoted and stored at ≤65° C. Serum of Days −21, −1, 7, 14 and 21 was tested for PCV2 antibody titers by ELISA, and PCV2 viremia by qPCR.

Individual fecal swabs were taken from each pig prior to challenge (Day −1), and weekly post-challenge. Individual sterile polyester swabs were used for collecting fecal swabs, and placed in a tube containing 3 mL sterile PBS medium. Swabs were swirled for 5 seconds in the medium before being discarded. Samples were aliquoted and stored at ≤−65° C. The fecal swab samples were tested for virus shedding by standard quantitative PCR procedures.

During necropsy, sections of tracheobronchial, mesentery and superficial inguinal lymph nodes, and tonsil tissues were collected in duplicate for each pig, individually identified, and fixed in 10% buffered formalin. One set was submitted for standard histopathology examination for lymphoid depletion (PCVAD), and histiocytic replacement. The conclusion was recorded as Yes (+) or No (−). A pig was considered having lymphoid depletion or histiocytic replacement if one or more tissues were scored "+". In addition, the tissues were also tested for PCV2 antigen by IHC. The results were recorded as 0 (no staining) and 1-3 (different levels of staining) A score of 0 was considered as PCV2 IHC (−), and a score of 1 or higher was considered as PCV2 IHC (+). A pig was considered IHC (+) if one or more tissues were IHC (+).

Due to the actual complexity of PCV epidemiology and the sensitivity of PCV2 qPCR, it is possible that some pigs may become viremic prior to challenge. Pigs that test viremic prior to challenge may be removed from the study, and may be excluded in the data analysis based on the discretion of the clinical sponsor.

The primary outcomes are the PCV2b divergent challenge isolate tested in comparison to the validated models for PCV2a and PCV2b.

Results

Animals administered the PCV2b Divergent challenge isolate had an increase in antibody titers from prior to challenge to the end of study across treatment groups. The undiluted challenge group followed by the T12 group (Diluted 1:5, administered IN) had the peak viremia at 14 days after challenge, with over 4 million and 1 million DNA copies/mL, respectively. The peak PCV2 shedding of the undiluted challenge material was 754,114 DNA copies/mL. The undiluted IM/IN and 1:5 IN only, resulted in the highest number of animals positive for histopathological abnormalities and PCV2 colonization.

Based on data collected from this PCV2b challenge optimization study (data not shown), challenge route and dose changed to 3 mL intranasal. The change in challenge route and dose is thought to decrease the chances of an adverse event thought to be caused by intramuscular administration and increase overall challenge take.

Example 6: Evaluation of Two Vaccine Candidates Against a PCV2b Challenge

The objective of the study was to assess the protection of a chimeric PCV2b vaccine and a PCV2b divergent vaccine, each represented at a low and high antigen dose, against a PCV2b challenge. The study design is outlined in Table 10. The placebo (T01) was 10% SP-Oil. The IVP's were as follows: T02, killed PCV1:PCV2b capsid chimera low dose (cPCV2b low), adjuvanted with 10% SP-Oil; T03, killed PCV1:PCV2b capsid chimera high dose (cPCV2b high), adjuvanted with 10% SP-Oil; T04, killed PCV2b-divergent vaccine low dose (PCV2b DIV low), adjuvanted with 10% SP-Oil; T05, killed PCV2b-divergent vaccine high dose (PCV2b DIV high), adjuvanted with 10% SP-Oil. The vaccines were produced using 20× concentrated antigen and then formulating the vaccine at: 0.69% antigen input=low dose or 3.00% antigen input=high dose.

TABLE 10

Study Design

| Group | N | Investigational Veterinary Product (IVP) | Vaccinations | Challenge Day | Strain | Dose, Route | Necropsy |
|---|---|---|---|---|---|---|---|
| T01 | 12 | Placebo | Day 0 (~3 wks of age) 2 mL IM Right side of neck | Day 21 (~6 wks of age) | PCV2b | 3 mL IN | Day 42 (~9 wks of age) and Tissue Collection |
| T02 | 12 | Killed, adjuvanted PCV1:PCV2b chimera (low dose) | | | | | |
| T03 | 12 | Killed, adjuvanted PCV1:PCV2b chimera (high dose) | | | | | |

TABLE 10-continued

| | | | Study Design | | | | |
|---|---|---|---|---|---|---|---|
| | | Investigational | | Challenge | | | |
| Group | N | Veterinary Product (IVP) | Vaccinations | Day | Strain | Dose, Route | Necropsy |
| T04 | 12 | Killed, adjuvanted PCV2b-Divergent (low dose) | | | | | |
| T05 | 12 | Killed, adjuvanted PCV2b-Divergent (high dose) | | | | | |

Pigs were ~3 weeks of age (21±7 days of age) on Day 0 for vaccination. A treatment administrator administered a single dose of 2 mL of the assigned vaccine intramuscularly (IM) into the right side of the neck. A single 3 mL sterile syringe with 1" or ¾" needle was used for each pig. Vaccination details were recorded. Pigs were observed within 1 hour (±30 minutes) after each vaccination for abnormal clinical signs, including but not limited to: lethargy, labored breathing, vomiting, and incoordination. Any observed clinical signs were documented on the general health form. A veterinarian was notified to follow up on the pig(s) with any of the signs described above.

Challenge was conducted on Day 21 when the pigs were about 6 weeks of age. Each pig was inoculated with a total 3 mL intranasally (IN) of a culture of a virulent PCV2b strain, pre-diluted to 4.8-5.8 log 10 TCID50/mL. A reserved aliquot of the challenge viruses was titrated following the challenge to confirm the actual challenge dose.

Individual blood samples (5-10 mL) were collected in serum separator tubes (SST) on Day −1 (prior to vaccination), and Days 7, 14, 20/21, 28, 35, and 42. Samples were aliquoted and stored at ≤−65° C. They were later tested for PCV2 antibody titers by ELISA and PCV2 viremia by qPCR.

During necropsy, sections of tracheobronchial, mesentery and superficial inguinal lymph nodes, and tonsil tissues were collected in duplicate for each pig, individually identified and fixed in 10% buffered formalin. One set was archived, while the other was submitted for standard histopathology examination for lymphoid depletion (PCVAD), and histiocytic replacement. The conclusion was recorded as Yes (+) or No (−). A pig was considered having lymphoid depletion or histiocytic replacement if one or more tissues were scored "+". In addition, the tissues were also tested for PCV2 antigen by IHC. The results were recorded as 0 (no staining) and 1-3 (different levels of staining) A score 0 was considered as PCV2 IHC (−), and a score of 1 or higher was considered as PCV2 IHC (+). A pig was considered IHC (+) if one or more tissues are IHC (+).

The primary outcome was the protection of one of the four candidate vaccines against the PCV2b challenge, when compared to the placebo. The primary variable was viremia, and the secondary variables were fecal shed and histopathological lesions.

Results

PCV2 Viremia

Figure 2:
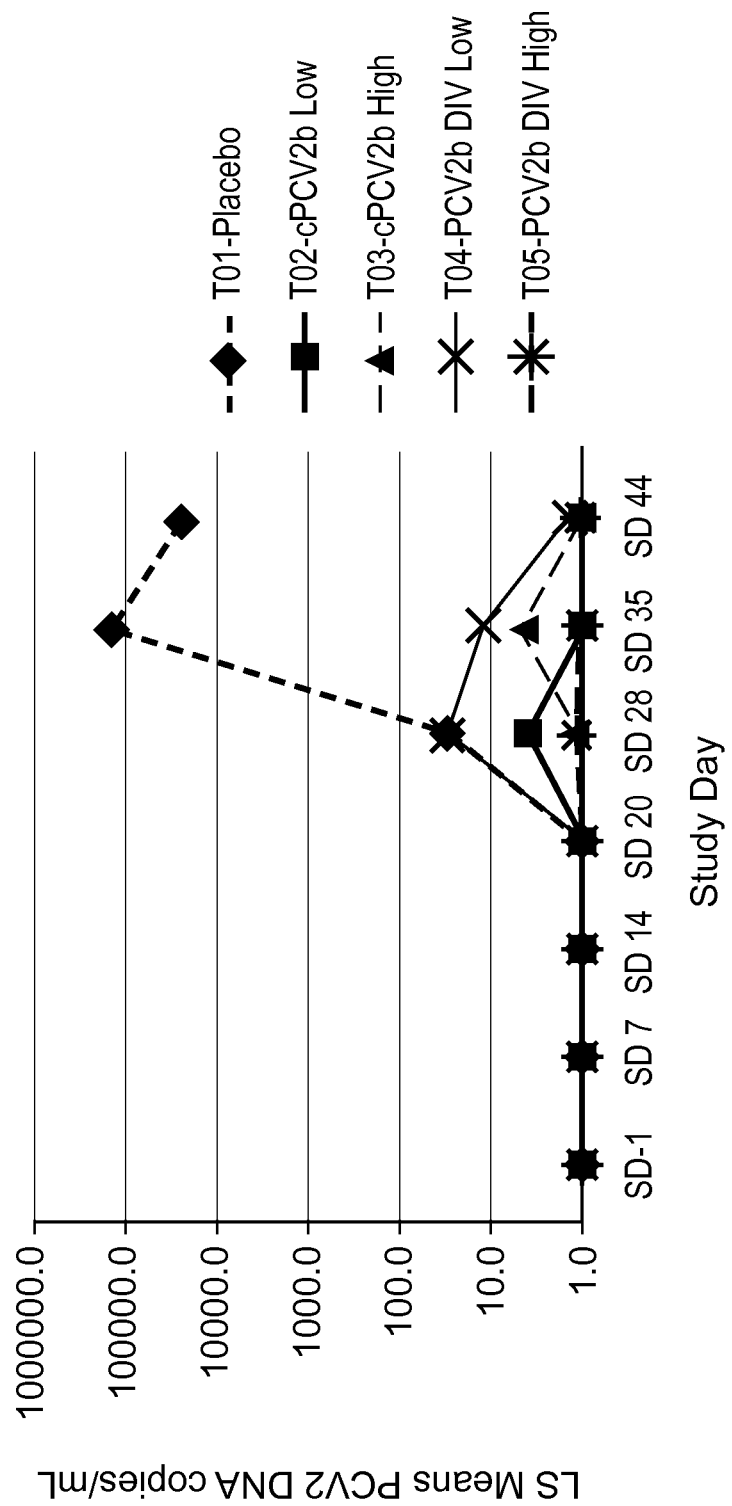
FIG. 2 is a graph showing geometric Least Squares Means of DNA copies by treatment day. *All "0"s were converted to 1 for graphing purposes.

Serum was collected weekly and analyzed for PCV2 viremia by quantitative PCR. Geometric least square means of each study day are illustrated in FIG. 2. All pigs stayed negative for PCV2 viremia prior to challenge, as demonstrated in Table 11 below.

TABLE 11

PCV2 Viremia (DNA Copies) as Tested by qPCR by Study Day

| | | Time Point (Geometric LS Mean DNA Copies) | | | | | | |
|---|---|---|---|---|---|---|---|---|
| | | Pre-challenge | | | | Post-challenge | | |
| Trt | Serial | Day −1 | Day 7 | Day 14 | Day 20 | Day 28 | Day 35 | Day 44 |
| T01 | Placebo | 0 | 0 | 0 | 0 | 30 | 132010.6 | 24113.9 |
| T02 | cPCV2b low | 0 | 0 | 0 | 0 | 3.8 | 0 | 0 |
| T03 | cPCV2b high | 0 | 0 | 0 | 0 | 1.2 | 4.5 | 0 |
| T04 | PCV2b DIV low | 0 | 0 | 0 | 0 | 29.9 | 12.1 | 1.4 |
| T05 | PCV2b DIV high | 0 | 0 | 0 | 0 | 1.2 | 0 | 0 |

Individual fecal swabs were taken from each pig prior to challenge (Day 20/21), and weekly post-challenge. Individual sterile polyester swabs were used for collecting fecal swab and placed in a tube containing 3 mL sterile PBS medium. Swabs were swirled for 5 seconds in the medium before discarded. Samples were aliquoted and stored at ≤−65° C. The fecal swab samples were tested for virus shedding by standard quantitative PCR procedure.

PCV2 Viremia (DNA Copies) by treatment and challenge are described below in Table 12. All treatment groups were significantly different from the T01 group post challenge on days 35 and 44 (P<0.0001).

Percent of animals that were ever positive throughout the course of the study are listed below (Table 12). The placebo group had a significantly higher number of animals that were ever positive compared to the vaccinated groups (P<0.0124).

TABLE 12 qPCR Qualitative Serum Viremia - Percent Ever Positive

| | Ever Positive? | | | | Total | |
| --- | --- | --- | --- | --- | --- | --- |
| | Pos | | Neg | | Observations | |
| Serial | # | % | # | % | Number | P-Value |
| Placebo | 11 | 100.0 | 0 | 0 | 11 | |
| cPCV2b low | 2 | 16.7 | 10 | 83.3 | 12 | 0.0001 |
| cPCV2b high | 2 | 16.7 | 10 | 83.3 | 12 | 0.0001 |
| PCV2b DIV low | 5 | 45.5 | 6 | 54.5 | 11 | 0.0124 |
| PCV2b DIV high | 1 | 8.3 | 11 | 91.7 | 12 | 0.0001 |

PCV2 Fecal Shedding

Figure 3:
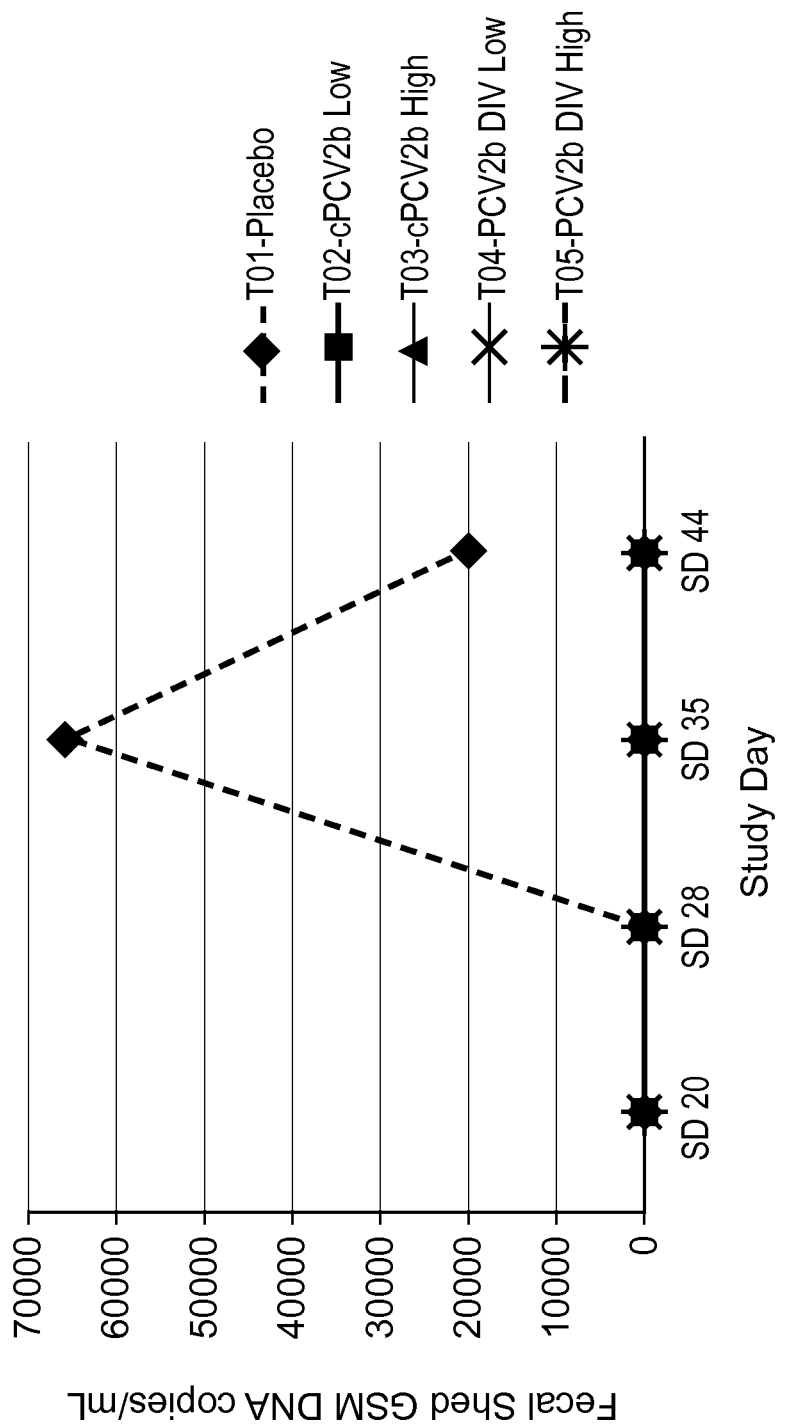
FIG. 3 is a graph showing geometric Least Squares Means of Fecal Shed (DNA Copies) by treatment day post challenge.*All "0"s were converted to 1 for graphing purposes.

Fecal shedding geometric least square means by study day are illustrated in FIG. 3. PCV2 fecal shedding (DNA Copies) by treatment and challenge are described below in Table 13. All treatment groups were significantly different from the T01 group post challenge on days 35 and 44 (P<0.0001).

TABLE 13

PCV2 Fecal Shed (DNA Copies) as Tested by qPCR

| | | Time Point (Geometric LS Mean DNA Copies) | | | |
| --- | --- | --- | --- | --- | --- |
| | | Prior to Challenge | Post-challenge | | |
| Trt | Serial | Day 20 | Day 28 | Day 35 | Day 44 |
| T01 | Placebo | 0 | 29.9 | 65713.8 | 19996.2 |
| T02 | cPCV2b low | 0 | 3.8 | 3.8 | 0 |
| T03 | cPCV2b high | 0 | 1.2 | 1.3 | 0 |
| T04 | PCV2b DIV low | 0 | 29.9 | 12.1 | 1.4 |
| T05 | PCV2b DIV high | 0 | 1.2 | 9.6 | 0 |

Percent of animals that were ever positive for shedding throughout the course of the study are listed below (Table 14). The placebo group had a significantly higher number of animals that were ever shedding compared to the vaccinated groups (P<0.0124).

TABLE 14 qPCR Qualitative Fecal shedding - Percent Ever Positive

| | Ever Positive? | | | | Total | |
| --- | --- | --- | --- | --- | --- | --- |
| | Pos | | Neg | | Observations | |
| Serial | # | % | # | % | Number | P-Value |
| Placebo | 11 | 100.0 | 0 | 0 | 11 | |
| cPCV2b low | 3 | 25.0 | 9 | 75.0 | 12 | 0.0003 |
| cPCV2b high | 1 | 8.3 | 11 | 91.7 | 12 | ≤0.0001 |
| PCV2b DIV low | 5 | 45.5 | 6 | 54.5 | 11 | 0.0124 |
| PCV2b DIV high | 4 | 33.3 | 8 | 66.7 | 12 | 0.0013 |

Serum Antibody Response

Figure 4:
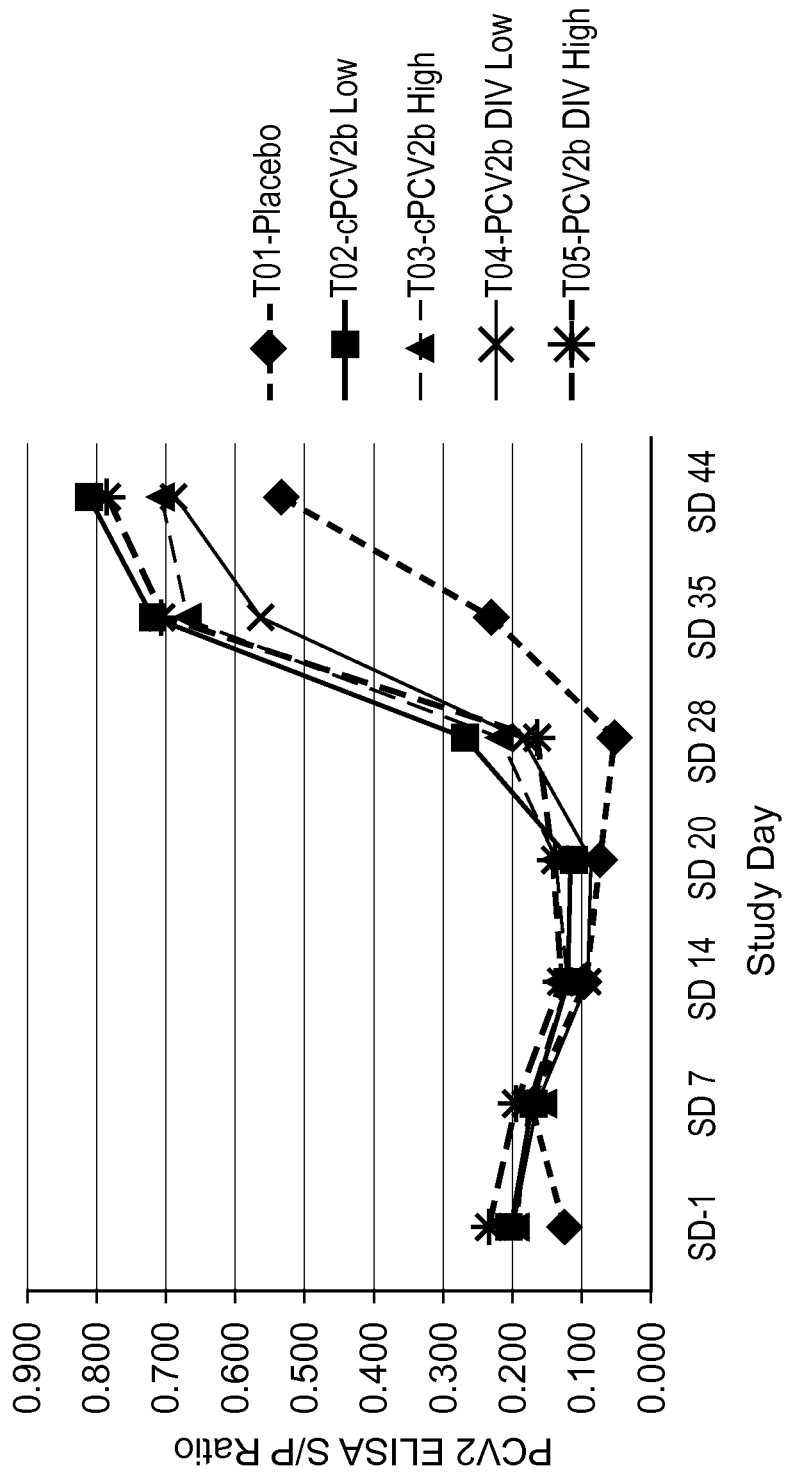
FIG. 4 is a graph showing PCV2 ELISA S/P LS Mean titers by treatment day and treatment.

PCV2 antibody titer means of each treatment by study day are illustrated in FIG. 4. All pigs were PCV2 seronegative prior to vaccination. Pigs in the Placebo group remained seronegative prior to challenge.

PCV2 ELISA antibody titers are summarized in Table 15 below. All titers >0.5 are considered to be PCV2 antibody positive. Pigs in all vaccine groups showed significant increases (P≤0.0895) of PCV2 antibody titer on Days 28-44 post vaccination when compared to placebo, indicating the active immune response to PCV2 following vaccination. In addition, the T03 and T05 also had significantly higher titers on day 20 post vaccination (P≤0.0684 and P≤0.0738, respectively).

TABLE 15

PCV2 ELISA S/P LS Mean Titers by Study Day

| Treatment | Day −1 | Day 7 | Day 14 | Day 20 | Day 28 |
| --- | --- | --- | --- | --- | --- |
| Placebo | 0.215 | 0.172 | 0.092 | 0.066 | 0.046 |
| cPCV2b low | 0.203 | 0.168 | 0.119 | 0.113 | 0.266* |
| cPCV2b high | 0.195 | 0.156 | 0.118 | 0.138* | 0.214* |
| PCV2b DIV low | 0.193 | 0.176 | 0.090 | 0.086 | 0.172* |
| PCV2b DIV high | 0.233 | 0.191 | 0.125 | 0.137* | 0.157* |

| Treatment | Day 35 | Day 44 |
| --- | --- | --- |
| Placebo | 0.225 | 0.526 |
| cPCV2b low | 0.715* | 0.807* |
| cPCV2b high | 0.667* | 0.706* |
| PCV2b DIV low | 0.563* | 0.685* |
| PCV2b DIV high | 0.702* | 0.783* |

Histopathology: Lymphoid Depletion (LD) and Virus Infection in Lymphoid Tissues (IHC)

PCV2 percent abnormal histopathology scores (data not shown) did not demonstrate a significant difference between the placebo and vaccinated groups when considering lymphoid lesions and the presence of PCV2 antigens.

The data from this study indicated that all pigs on study up to the challenge on Day 21 remained free of PCV2 infection as evidenced by 1) lack of detectable PCV2 DNA in serum collected at weekly intervals from the time of vaccination to the time of challenge and 2) Lack of serologic evidence among the T01 group that there was any unintended exposure to PCV2 prior to challenge. All vaccines significantly protected vaccinated animals from becoming viremic post challenge. Also, all vaccines significantly reduced fecal shedding of PCV2 post challenge in vaccinated animals. Pigs in all vaccine groups showed significant increases (P≤0.0895) of PCV2 antibody titer on Days 28-44 post vaccination when compared to placebo, indicating an active immune response to PCV2 following vaccination. There was a numerical reduction in colonization (IHC) in all vaccinated groups versus controls, but it was not statistically significant. The lack of significant difference between the groups could have been due to the weak challenge take seen in the control group.

Example 7: Evaluation of Two Vaccine Candidates Against a PCV2b-Divergent Challenge The objective of the study was to assess the protection of a chimeric PCV2b vaccine and a PCV2b divergent vaccine, each represented at a low and high antigen dose, as well as a PCV2a capsid expressed in baculovirus, against a PCV2b divergent challenge. The study design is outlined in Table 16. The placebo (T01) was 10% SP-Oil. The IVP's were as follows: T02, killed PCV1:PCV2b capsid chimera low dose (cPCV2b low), adjuvanted with 10% SP-Oil; T03, killed PCV1:PCV2b capsid chimera high dose (cPCV2b high), adjuvanted with 10% SP-Oil; T04, killed PCV2b-divergent vaccine low dose (PCV2b DIV low), adjuvanted with 10% SP-Oil; T05, killed PCV2b-divergent vaccine high dose (PCV2b DIV high), adjuvanted with 10% SP-Oil; T06, killed baculovirus expressing a PCV2a capsid, in an aqueous-based adjuvant (comparative product). The T02-T05 vaccines were produced using 20× concentrated antigen and then formulating the vaccine at: 0.69% antigen input=low dose or 3.00% antigen input=high dose.

TABLE 16

Study Design

| Group | N | Investigational Veterinary Product (IVP) | Vaccinations | Challenge Day | Challenge Strain | Dose, Route* | Necropsy |
|---|---|---|---|---|---|---|---|
| T01 | 12 | Placebo | Day 0 (~3 wks of age) 2 mL IM Right side of neck | Day 21 (~6 wks of age) | PCV2b-divergent | 3 mL IN | Day 42 (~9 wks of age) and Tissue Collection |
| T02 | 12 | Killed, adjuvanted PCV1:PCV2b chimera (low dose) | | | | | |
| T03 | 12 | Killed, adjuvanted PCV1:PCV2b chimera (high dose) | | | | | |
| T04 | 12 | Killed, adjuvanted PCV2b-Divergent (low dose) | | | | | |
| T05 | 12 | Killed, adjuvanted PCV2b-Divergent (high dose) | | | | | |
| T06 | 12 | Killed baculovirus expressing PCV2a capsid | 1 mL IM Right side of neck | | | | |

Pigs were ~3 weeks of age (21±8 days of age) on Day 0 for vaccination. A treatment administrator administered a single dose of 2 mL (T01-T05) or 1 ml (T06) of the assigned vaccine intramuscularly (IM) into the right side of the neck. A single 3 mL sterile syringe with 1" or ¾" needle was used for each pig. Vaccination details were recorded. Pigs were observed within 1 hour (±30 minutes) after each vaccination for abnormal clinical signs, including but not limited to: lethargy, labored breathing, vomiting, and incoordination. Any observed clinical signs were documented on the general health form. A veterinarian was notified to follow up on the pig(s) with any of the signs described above.

Challenge was conducted on Day 21 when the pigs were about 6 weeks of age. Each pig was inoculated with a total 3 mL intransally (IN) of a culture of a virulent PCV2b-divergent strain, pre-diluted to 4.8-5.8 log 10 TCID50/mL. A reserved aliquot of the challenge viruses was titrated following the challenge to confirm the actual challenge dose.

Individual blood samples (5-10 mL) were collected in serum separator tubes (SST) on Day −1 (prior to vaccination), and Days 7, 14, 20/21, 28, 35, and 42. Samples were aliquoted and stored at ≤−65° C. They were later tested for PCV2 antibody titers by ELISA and PCV2 viremia by qPCR.

Individual fecal swabs were taken from each pig prior to challenge (Day 20/21), and weekly post-challenge. Individual sterile polyester swabs were used for collecting fecal swab and placed in a tube containing 3 mL sterile PBS medium. Swabs were swirled for 5 seconds in the medium before discarded. Samples were aliquoted and stored at ≤−65° C. The fecal swab samples were tested for virus shedding by standard quantitative PCR procedure.

During necropsy, sections of tracheobronchial, mesentery and superficial inguinal lymph nodes, and tonsil tissues were collected in duplicate for each pig, individually identified and fixed in 10% buffered formalin. One set was archived, while the other was submitted for standard histopathology examination for lymphoid depletion (PCVAD), and histiocytic replacement. The conclusion was recorded as Yes (+) or No (−). A pig was considered having lymphoid depletion or histiocytic replacement if one or more tissues were scored "+". In addition, the tissues were also tested for PCV2 antigen by IHC. The results were recorded as 0 (no staining) and 1-3 (different levels of staining) A score 0 was considered as PCV2 IHC (−), and a score of 1 or higher was considered as PCV2 IHC (+). A pig was considered IHC (+) if one or more tissues were IHC (+).

The primary outcome was the protection of one of four candidate vaccines and the baculovirus vaccine against the PCV2b-divergent challenge, when compared to the placebo. The primary variable was viremia, and the secondary variables were fecal shed and histopathological lesions.

Figure 5:
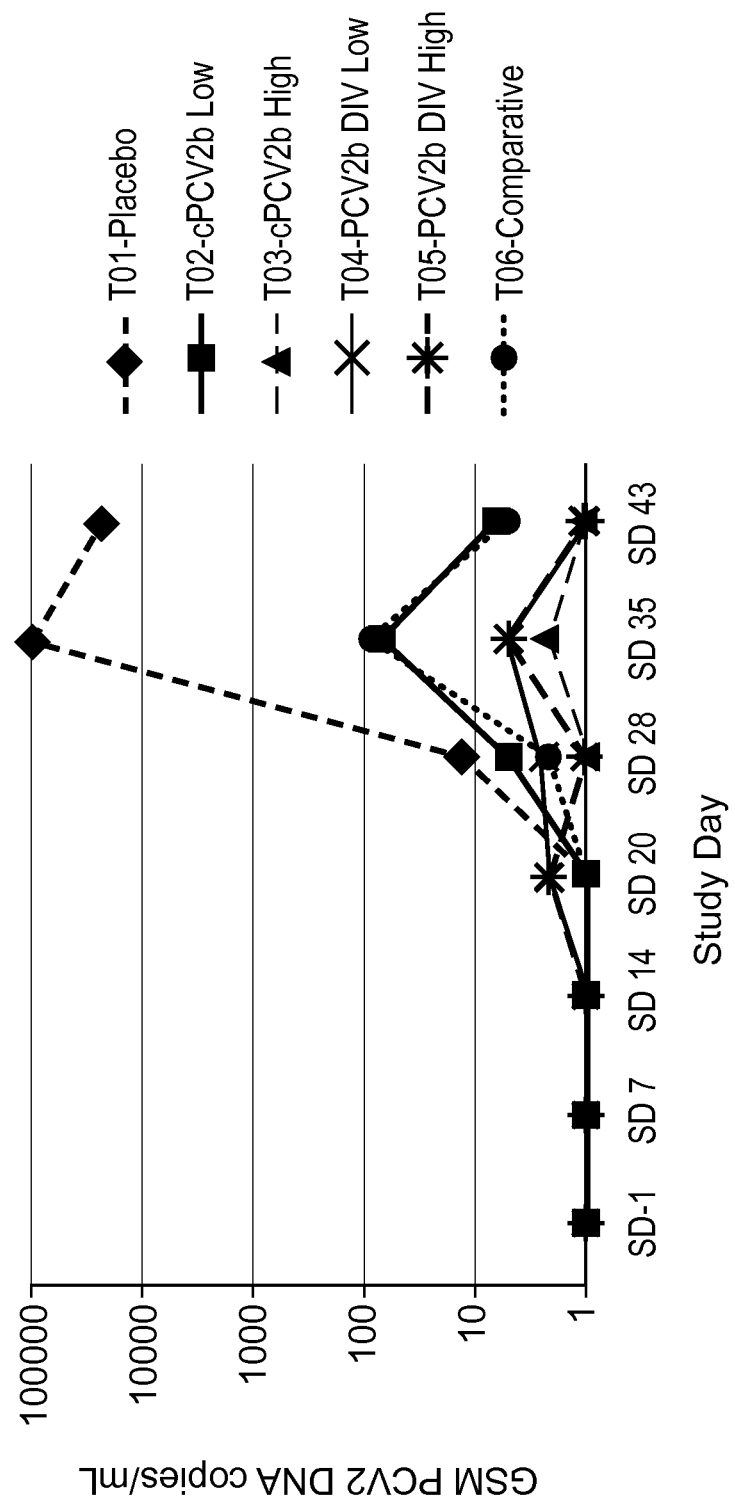
FIG. 5 is a graph of backtransformed geometric Least Squares Means of DNA copies by treatment day.

PCV2 Viremia Serum was collected weekly and analyzed for PCV2 viremia by quantitative PCR. Geometric least square means of each study day are illustrated in FIG. 5. All pigs except one animal in both the T04 and T05 groups stayed negative for PCV2 viremia prior to challenge, as demonstrated in Table 17 below.

TABLE 17

PCV2 Viremia (DNA Copies) as Tested by qPCR by Study Day

| | | Time Point (LS Mean DNA Copies) | | | | | | |
|---|---|---|---|---|---|---|---|---|
| | | Pre-challenge | | | | Post-challenge | | |
| Trt | Serial | Day −1 | Day 7 | Day 14 | Day 20 | Day 28 | Day 35 | Day 44 |
| T01 | Placebo | 0 | 0 | 0 | 0 | 12.2 | 91196.2 | 22165.7 |
| T02 | cPCV2b low | 0 | 0 | 0 | 0 | 3.8 | 68 | 4.9 |

TABLE 17-continued

PCV2 Viremia (DNA Copies) as Tested by qPCR by Study Day

| | | Time Point (LS Mean DNA Copies) | | | | | |
|---|---|---|---|---|---|---|---|
| | | Pre-challenge | | | | Post-challenge | |
| Trt | Serial | Day −1 | Day 7 | Day 14 | Day 20 | Day 28 | Day 35 | Day 44 |
| T03 | cPCV2b high | 0 | 0 | 0 | 0 | 0.0 | 1.2 | 0.0 |
| T04 | PCV2b DIV low | 0 | 0 | 0 | 1.2 | 1.5 | 3.8 | 0.0 |
| T05 | PCV2b DIV high | 0 | 0 | 0 | 1.2 | 0.0 | 3.8 | 0.0 |
| T06 | baculovirus expressing PCV2a capsid | 0 | 0 | 0 | 0.0 | 1.2 | 86.0 | 3.8 |

Percent of animals that were ever positive throughout the course of the study are listed below (Table 18). The placebo group had a significantly higher percentage of animals that were ever positive compared to the vaccinated groups (P≤0.0046).

TABLE 18 qPCR Qualitative Serum Viremia - Percent Ever Positive

| | | Ever Positive? | | | | Total | |
|---|---|---|---|---|---|---|---|
| | | Pos | | Neg | | Observations | |
| Trt | Serial | # | % | # | % | Number | P-Value |
| T01 | Placebo | 12 | 100.0 | 0 | 0 | 12 | |
| T02 | cPCV2b low | 5 | 41.7 | 7 | 58.3 | 12 | 0.0046 |
| T03 | cPCV2b high | 1 | 8.3 | 11 | 91.7 | 12 | 0.0001 |
| T04 | PCV2b DIV low | 2 | 16.7 | 10 | 83.3 | 12 | 0.0001 |
| T05 | PCV2b DIV high | 2 | 16.7 | 10 | 83.3 | 12 | 0.0001 |
| T06 | baculovirus expressing PCV2a capsid | 5 | 41.7 | 7 | 58.3 | 12 | 0.0046 |

PCV2 Fecal Shedding

Figure 6:
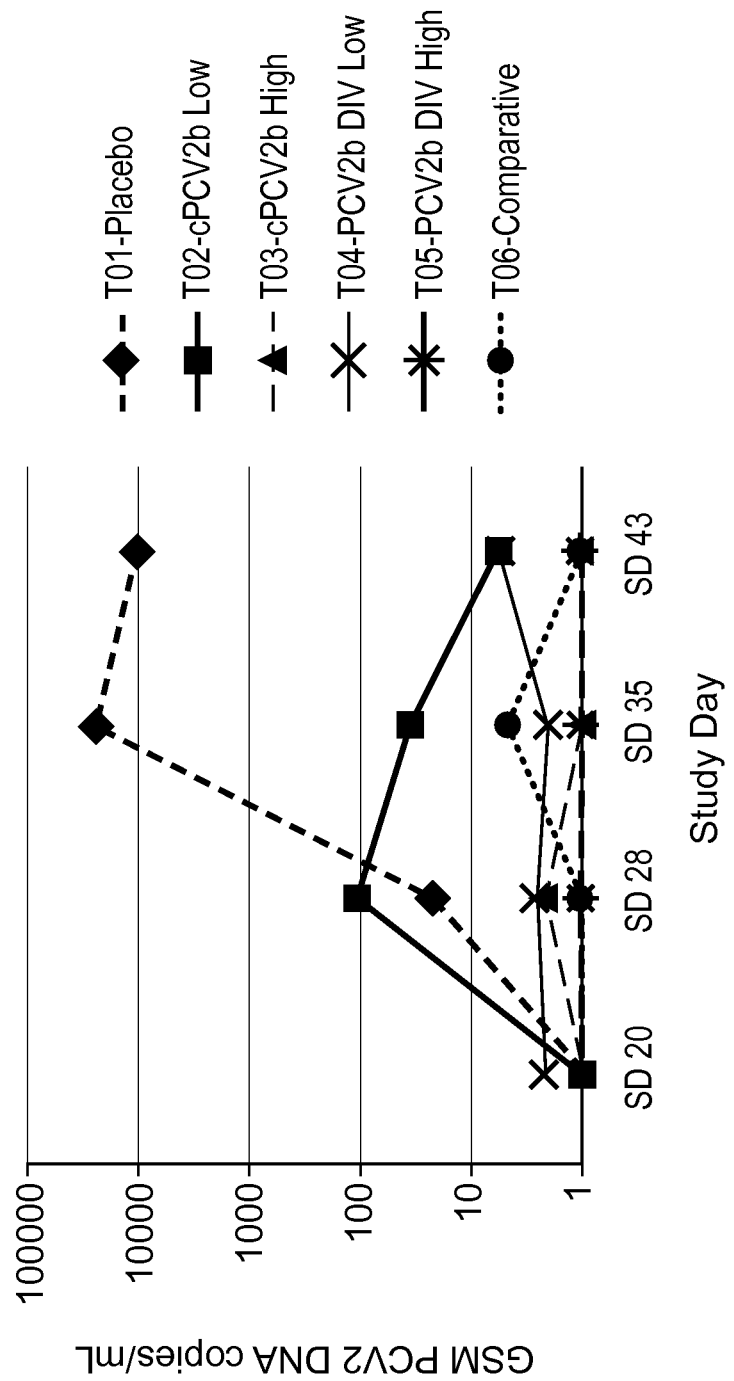
FIG. 6 is a graph of backtransformed geometric Least Squares Means of fecal shed (DNA Copies) by treatment day post challenge.

Fecal shedding geometric least square means by study day are illustrated in FIG. 6. PCV2 fecal shedding (DNA Copies) by treatment and challenge are described below in Table 19. One animal in the T04 group was shedding the day prior to challenge. All vaccine groups were shedding significantly lower (P≤0.0001) least squares mean PCV2 DNA copy numbers than the placebo group on Days 35 and 43 post challenge. In addition, the T03, T05 and T06 groups were also noted with shedding significantly lower least squares mean DNA copies (P≤0.0830) on Day 28 of study.

TABLE 19

PCV2 Fecal Shed (DNA Copies) as Tested by qPCR

| | | Time Point (Geometric LS Mean DNA Copies) | | | |
|---|---|---|---|---|---|
| | | Prior to Challenge | Post-challenge | | |
| Trt | Serial | Day 20 | Day 28 | Day 35 | Day 44 |
| T01 | Placebo | 0 | 22.3 | 24228.5 | 10281.5 |
| T02 | cPCV2b low | 0 | 111.3 | 36.2 | 5.1 |
| T03 | cPCV2b high | 0 | 1.2 | 0.0 | 0.0 |
| T04 | PCV2b DIV low | 1.2 | 1.7 | 1.2 | 5.0 |
| T05 | PCV2b DIV high | 0 | 0.0 | 0.0 | 0.0 |
| T06 | baculovirus expressing PCV2a capsid | 0 | 0.0 | 3.8 | 0.0 |

The percent of animals that were ever positive for shedding throughout the course of the study are listed below (Table 20). Following challenge, when compared to the placebo group, groups T03-T06 had a significant reduction (P≤0.0028) in the percent of pigs shedding PCR detectable PCV2 DNA.

TABLE 20 qPCR Qualitative Fecal shedding - Percent Ever Positive

| | Ever Positive? | | | | Total | |
|---|---|---|---|---|---|---|
| | Pos | | Neg | | Observations | |
| | # | % | # | % | Number | P-Value |
| Placebo | 11 | 91.7 | 1 | 8.3 | 12 | |
| cPCV2b low | 8 | 66.7 | 4 | 33.3 | 12 | 0.3168 |
| cPCV2b high | 1 | 8.3 | 11 | 91.7 | 12 | 0.0001 |
| PCV2b DIV low | 3 | 25.0 | 9 | 75.0 | 12 | 0.0028 |
| PCV2b DIV high | 0 | 0 | 12 | 100.0 | 12 | 0.0001 |
| baculovirus expressing PCV2a capsid | 2 | 16.7 | 10 | 83.3 | 12 | 0.0006 |

Serum Antibody Response

Figure 7:
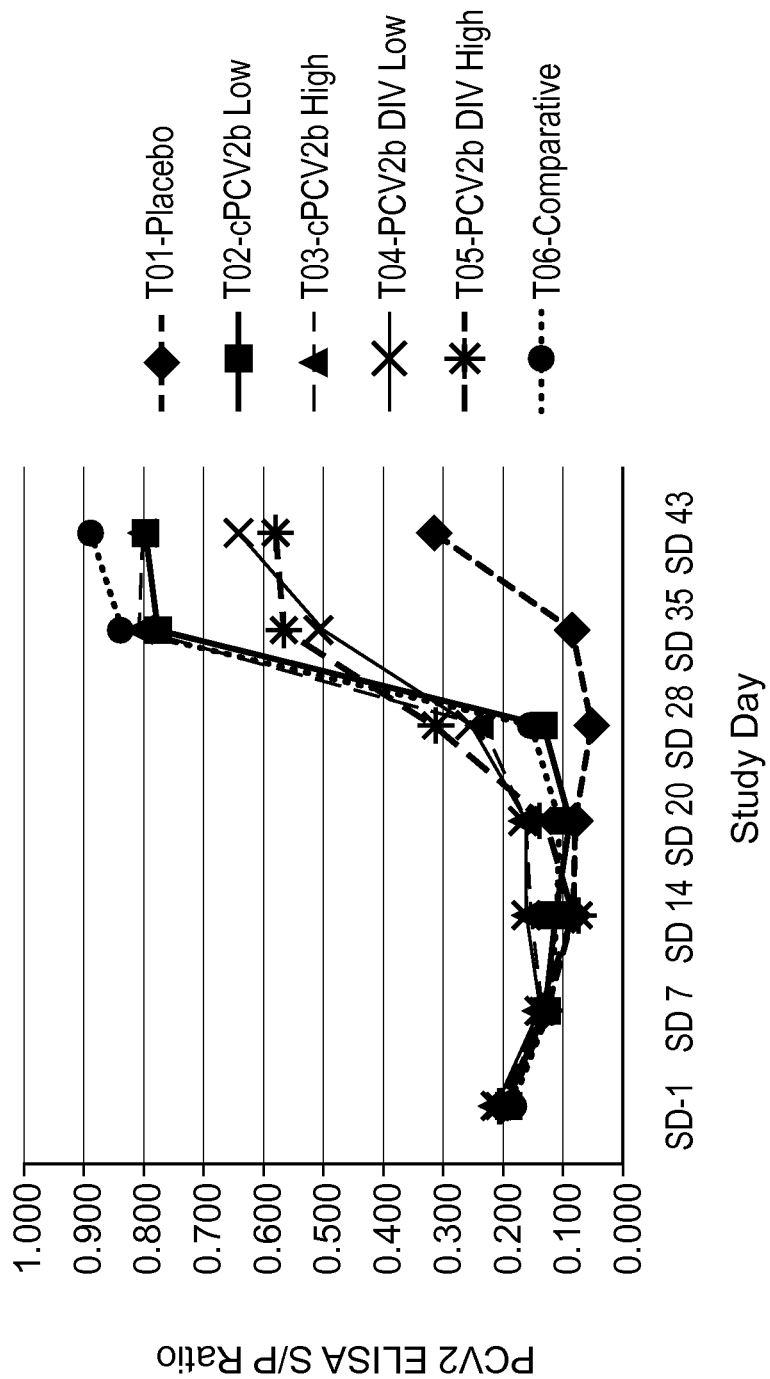
FIG. 7 is a graph showing PCV2 ELISA S/P LS Mean Titers by Study Day

With respect to PCV2 antibody titers, the results indicated that the PCV2b divergent vaccine treatments (T04; T05) had a stronger serologic response compared to the other treatments prior to challenge at Study Day 21, as assessed by ELISA (Table 21; FIG. 7). Following challenge, however, the PCV2b divergent treatments did not respond as strongly as the other treatments (FIG. 7). One possible conclusion is that the animal already had a specific strong anti-PCV2b divergent antibody response, and was able to neutralize and eliminate the challenge virus very quickly. This translated to a decreased antibody response post-challenge, when compared to that of the heterologous vaccines. While serology is not the same as efficacy, it has been demonstrated that declining antibody titers in pigs receiving an efficacious vaccine indicates protection (Thacker et al., 2013, Proc AASV, 217).

TABLE 21

PCV2 ELISA

| Treatment | Study Day | | | | | | |
|---|---|---|---|---|---|---|---|
| | −1 | 7 | 14 | 20 | 28 | 35 | 43 |
| T01 | 0.2094 | 0.1427 | 0.0937 | 0.0824 | 0.0539 | 0.0877 | 0.3064 |
| T02 | 0.1943 | 0.1249 | 0.1133 | 0.0981 | 0.1328 | 0.7637* | 0.7935* |
| T03 | 0.2102 | 0.1377 | 0.1458 | 0.1671* | 0.2362* | 0.8084* | 0.7973* |
| T04 | 0.1856 | 0.1399 | 0.1467 | 0.1560 | 0.2388* | 0.4836* | 0.6209* |
| T05 | 0.2064 | 0.1274 | 0.0772 | 0.1362 | 0.2902* | 0.5438* | 0.5749* |
| T06 | 0.1814 | 0.1283 | 0.0999 | 0.1089 | 0.1627 | 0.8350* | 0.8902* |

*P-Value <0.10 vs. T01

Histopathology: Lymphoid Depletion (LD), and Virus Infection in Lymphoid Tissues (IHC)

At the time of necropsy, when compared to the placebo group, all vaccine groups had significantly less percentage of animals with microscopic lymphoid lesions (LD) and PCV2 antigen colonization (IHC), P≤0.0995.

The PCV2 IHC data are summarized in Table 22 below.

TABLE 22

PCV2 IHC Scores: If lymphoid or tonsil tissues ever abnormal

| Trt | Serial | Ever Abnormal? | | | | Total Obs |
|---|---|---|---|---|---|---|
| | | No | | Yes | | |
| | | # | % | # | % | Number |
| T01 | Placebo | 4 | 33.3 | 8 | 66.7 | 12 |
| T02 | cPCV2b low | 9 | 75 | 3 | 25 | 12 |
| T03 | cPCV2b high | 10 | 83.3 | 2 | 16.7 | 12 |
| T04 | PCV2b DIV low | 11 | 91.7 | 1 | 8.3 | 12 |
| T05 | PCV2b DIV high | 12 | 100 | 0 | 0 | 12 |
| T06 | baculovirus expressing PCV2a capsid | 12 | 100 | 0 | 0 | 12 |

The PCV2 Lymphoid Depletion (LD) data are summarized in Table 23 below.

TABLE 23

PCV2 Lymphoid Depletion Scores: If lymphoid or tonsil tissues ever abnormal

| Serial | Ever Abnormal? | | | | Total Obs |
|---|---|---|---|---|---|
| | No | | Yes | | |
| | # | % | # | % | Number |
| Placebo | 4 | 33.3 | 8 | 66.7 | 12 |
| cPCV2b low | 9 | 75 | 3 | 25 | 12 |
| cPCV2b high | 12 | 100 | 0 | 0 | 12 |
| PCV2b DIV low | 10 | 83.3 | 2 | 16.7 | 12 |
| PCV2b DIV high | 11 | 91.7 | 1 | 8.3 | 12 |
| baculovirus expressing PCV2a capsid | 12 | 100 | 0 | 0 | 12 |

The data from this study indicated that all treatment groups least squares mean PCV2 titers were seronegative prior to vaccination. Pigs in the Placebo group remained seronegative prior to challenge. One animal in both the T04 and T05 groups were viremic the day prior to challenge. The animal in the T04 group was also shedding, however less than 10% of the animals became viremic prior to challenge and the study was considered valid. Following challenge, when compared to the placebo group, all vaccinated groups had a significant reduction in the percent of viremic pigs. Following challenge, when compared to the placebo group, groups T03-T06 had a significant reduction in the percent of pigs shedding PCR detectable PCV2 DNA. At necropsy, when compared to the placebo group, all vaccine groups had significantly less percentage of animals with microscopic lymphoid lesions (LD) and PCV2 antigen colonization. The study demonstrated that the cPCV1-2b, PCV2b divergent and baculovirus expressing PCV2a capsid vaccines cross protect against a PCV2b divergent strain challenge.

It is to be understood that the examples above are provided by way of illustration only, and nothing therein should be deemed a limitation upon the overall scope of the invention.

SEQUENCE LISTING

<160> NUMBER OF SEQ ID NOS: 67

<210> SEQ ID NO 1
<211> LENGTH: 234
<212> TYPE: PRT
<213> ORGANISM: Porcine circovirus

<400> SEQUENCE: 1

Met Thr Tyr Pro Arg Arg Arg Phe Arg Arg Arg His Arg Pro Arg
1               5                   10                  15

```
Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 2
<211> LENGTH: 705
<212> TYPE: DNA
<213> ORGANISM: Porcine circovirus

<400> SEQUENCE: 2

```
atgacgtatc cwaggaggcg tttccgcaga cgaagacacc gcccccgcag ccatcttggc      60
cagatcctcc gccgccgccc ctggctcgtc cacccccgcc accgttaccg ctggagaagg     120
aaaaatggca tcttcaacac ccgcctctcc cgcaccatcg gttatactgt caagaaaacc     180
acagtcagaa cgccctcctg gaatgtggac atgatgagat ttaatattaa tgattttctt     240
cccccaggag ggggctcaaa cccccctcact gtgccctttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata acccagccct tctcctacca ctcccggtac     480
tttaccccga aacctgtcct tgataggaca atcgattact tccaacccaa taacaaaaga     540
aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat ttaatcttaa agacccccca cttaacccta agtga                     705
```

<210> SEQ ID NO 3
<211> LENGTH: 234
<212> TYPE: PRT

<213> ORGANISM: Porcine circovirus

<400> SEQUENCE: 3

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro

```
ttcagagaat ttaatcttaa agaccccca cttaaccta agtga                    705
```

<210> SEQ ID NO 5
<211> LENGTH: 234
<212> TYPE: PRT
<213> ORGANISM: Porcine circovirus

<400> SEQUENCE: 5

```
Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Ala Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile His Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 6
<211> LENGTH: 705
<212> TYPE: DNA
<213> ORGANISM: Porcine circovirus

<400> SEQUENCE: 6

```
atgacgtatc caaggaggcg ttaccgaaga cgaagacacc gcccccgcag ccatcttggc    60
cagatcctcc gccgccgccc ctggctcgtc caccccgcc accgttaccg ctggagaagg    120
aaaaatggca tcttcaacac ccgcctctcc cgcaccatcg gttatactgt caaagctacc    180
acagtaagaa cgcccctcctg gaatgtggac atgatgagat taatattaa tgatttctt    240 ccccccaggag ggggctcaaa cccctcact gtgccctttg aatactacag aataaggaag    300
gttaaggttg aattctggcc ctgctcccca atcacccagg gtgacagggg agtgggctcc    360
actgctgtta ttctagatga taactttgta acaaaggcca atgccctaac ctatgacccc    420
tatgtaaact actcctcccg ccataccata ccccagccct tctcctacca ctcccgctat    480
```

```
ttcaccccca aacctgtcct tgataggaca atcgattact tccaacccaa taacaaaaga      540
aatcaactct ggctgagact acaaactact ggaaatgtag accatgtagg cctcggcact      600
gcgttcgaaa acagtataca cgaccaggac tacaatatcc gtataaccat gtatgtacaa      660
ttcagagaat ttaatcttaa agaccccca cttaaccccta agtga                      705
```

<210> SEQ ID NO 7
<211> LENGTH: 234
<212> TYPE: PRT
<213> ORGANISM: Porcine circovirus

<400> SEQUENCE: 7

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Ala Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Lys Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 8
<211> LENGTH: 705
<212> TYPE: DNA
<213> ORGANISM: Porcine circovirus

<400> SEQUENCE: 8

```
atgacgtatc caaggaggcg ttaccgaaga cgaagacacc gccccgcag ccatcttggc       60 cagatcctcc gccgccgccc ctggctcgtc caccccgcc accgttaccg ctggagaagg      120
aaaaatggca tcttcaacac ccgcctctcc cgcaccatcg gttatactgt caaagctacc      180
acagtcagaa cgcctcctg gaatgtggac atgatgagat ttaatattaa tgattttctt      240
cccccaggag ggggctcaaa ccccctcact gtgccctttg aatactacag aataaggaag      300
```

```
gttaaggttg aattctggcc ctgctcccca atcacccagg gtgacagggg agtgggctcc    360
actgctgtta ttctagatga taactttgta acaaaggcca atgccctaac ctatgacccc    420
tatgtaaact actcctcccg ccataccata ccccagccct tctcctacca ctcccgctat    480
ttcaccccca aacctgtcct tgataggaca atcgattact ccaacccaa taacaaaaga    540 aatcaactct ggctgagact acaaactact ggaaatgtag accatgtagg actcggcact    600
gccttcgaaa acagtaaata cgaccaggac tacaatatcc gtataaccat gtatgtacaa    660
ttcagagaat ttaatcttaa agacccccca cttaacccta agtga                     705
```

<210> SEQ ID NO 9
<211> LENGTH: 234
<212> TYPE: PRT
<213> ORGANISM: Porcine circovirus

<400> SEQUENCE: 9

```
Met

```
aaaaatggca tcttcaacac ccgcctctcc cgcaccatcg gttatactgt caagaaaacc      180
acagtcagaa cgcccctcct gaatgtggac atgatgagat ttaatattaa tgattttctt      240
cccccaggag ggggctcaaa ccccctcact gtgccctttg aatactacag ataaggaag       300 gttaaggttg aattctggcc ctgctcccca atcacccagg gtgacagggg agtgggctcc      360
actgctgtta ttctagatga taactttgta acaaaggcca atgccctaac ctatgacccc      420
tatgtaaact actcctcccg ccataccata ccccagccct tctcctacca ctcccggtac      480
tttaccccga aacctgtcct tgataggaca atcgattact ccaacccaa taacaaaga       540 aatcaactct ggctgagact acaaactact ggaaatgtag accatgtagg cctcggcact      600
gcgttcgaaa acagtatata cgaccaggac tacaatatcc gtataaccat gtatgtacaa      660
ttcagagaat ttaatcttaa agaccccccca cttaacccta agtga                    705
```

```
<210> SEQ ID NO 11
<211> LENGTH: 234
<212> TYPE: PRT
<213> ORGANISM: Porcine circovirus

<400> SEQUENCE: 11
```

Met Thr Tyr Pro Met Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Ala Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

```
<210> SEQ ID NO 12
<211> LENGTH: 705
<212> TYPE: DNA
<213> ORGANISM: Porcine circovirus
```

-continued

<400> SEQUENCE: 12

```
atgacgtatc ctatgaggcg tttccgcaga cgaagacacc gcccccgcag ccatcttggc      60
cagatcctcc gccgccgccc ctggctcgtc accccccgcc accgttaccg ctggagaagg     120
aaaaatggca tcttcaacac ccgcctctcc cgcaccatcg gttatactgt caagaaaacc     180
acagtcagaa cgccctcctg gaatgtggac atgatgagat taatattaa tgattttctt      240
cccccaggag ggggctcaaa ccccctcact gtgccctttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata acccagccct ctcctacca ctcccggtac      480
tttgccccga aacctgtcct tgataggaca atcgattact ccaacccaa taacaaaaga      540
aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat ttaatcttaa agacccccca cttaaccctaa gtga                     705
```

<210> SEQ ID NO 13
<211> LENGTH: 233
<212> TYPE: PRT
<213> ORGANISM: Porcine circovirus

<400> SEQUENCE:

<210> SEQ ID NO 14
<211> LENGTH: 702
<212> TYPE: DNA
<213> ORGANISM: Porcine circovirus

<400> SEQUENCE: 14

```
atgacgtatc caaggaggcg tttccgcaga cgaagacacc gcccccgcag ccatcttggc      60
cagatcctcc gctgccgccc ctggctcgtc caccccgcc accgttaccg ctggagaagg      120
aaaaatggca tcttcaacac ccgcctctcc cgcaccatag gttatactgt caagaaaacc     180
acagtcagaa cgcccctcctg gaatgtggac atgatgagat taatattaa tgatttctt     240
cccccaggag ggggctcaaa cccctcact gtgcccttg aatactacag aataaggaag      300
gttaaggttg aattctggcc ctgctcccca atcacccagg gtgacagggg agtgggctcc    360
actgctgtta ttctagatga taactttgta acaaaggcca atgccctaac ctatgacccc    420
tatgtaaact actcctcccg ccataccata cccagccct ctcctacca ctcccggtac      480
tttaccccga aacctgtcct tgataggaca atcgattact ccaacccaa taacaaaga      540
aatcaactct ggctgagact acaaactact ggaaatgtag accatgtagg cctcggcact   600
gcgttcgaaa acagtatata cgaccaggac tacaatatcc gtaaccat gtatgtacaa      660
ttcagagaat ttaatcttaa agacccccca cttaacccctt aa                      702
```

<210> SEQ ID NO 15
<211> LENGTH: 233
<212> TYPE: PRT
<213> ORGANISM: Porcine circovirus

<400> SEQUENCE: 15

Met Thr Tyr Pro Arg Arg Phe Arg Arg Arg His Arg Pro Arg
1               5                   10                  15

Ser His Leu Gly Gln Ile Leu Arg Cys Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

```
Gln Asp Tyr Asn Ile Arg Ile Thr Met Tyr Val Gln Phe Arg Glu Phe
    210                 215                 220
Asn Leu Lys Asp Pro Pro Leu Asn Pro
225                 230
```

<210> SEQ ID NO 16
<211> LENGTH: 702
<212> TYPE: DNA
<213> ORGANISM: Porcine circovirus

<400> SEQUENCE: 16

```
atgacgtatc caaggaggcg tttccgcaga cgaagacacc gcccccgcag ccatcttggc      60
cagatcctcc gctgccgccc ctggctcgtc cacccccgcc accgttaccg ctggagaagg     120
aaaaatggca tcttcaacac ccgcctctcc cgcaccatag gttatactgt caagaaaacc     180
acagtcagaa cgccctcctg gaatgtggac atgatgagat taatattaa tgattttctt     240
cccccaggag ggggctcaaa cccctcact gtgccctttg aatactacag aataaggaag      300
gttaaggttg aattctggcc ctgctcccca atcacccagg gtgacagggg agtgggctcc     360
actgctgtta ttttagatga taactttgta acaaaggcca atgccctaac ctatgacccc     420
tatgtaaact actcctcccg ccataccata acccagccct ctcctacca ctcccggtac      480
tttaccccga aacctgtcct tgataggaca atcgattact ccaacccaa taacaaaga      540
aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa agaccccca cttaacccta aa                         702
```

<210> SEQ ID NO 17
<211> LENGTH: 233
<212> TYPE: PRT
<213> ORGANISM: Porcine circovirus

<400> SEQUENCE: 17

```
Met Thr Tyr Pro Arg Arg Arg Phe Arg Arg Arg His Arg Pro Arg
1               5                   10                  15
Ser His Leu Gly Gln Ile Leu Arg Cys Arg Pro Trp Leu Val His Pro
                20                  25                  30
Arg His Arg Tyr Arg Trp Arg Arg Lys Asn Gly Ile Phe Asn Thr Arg
            35                  40                  45
Leu Ser Arg Thr Met Gly Tyr Thr Val Lys Lys Thr Thr Val Arg Thr
        50                  55                  60
Pro Ser Trp Asn Val Asp Met Met Arg Phe Asn Ile Asn Asp Phe Leu
65                  70                  75                  80
Pro Pro Gly Gly Gly Ser Asn Pro Leu Thr Val Pro Phe Glu Tyr Tyr
                85                  90                  95
Arg Ile Arg Lys Val Lys Val Glu Phe Trp Pro Cys Ser Pro Thr Thr
            100                 105                 110
Gln Gly Asp Arg Gly Val Gly Ser Thr Ala Val Ile Leu Asp Asp Asn
        115                 120                 125
Phe Val Thr Lys Ala Asn Ala Leu Thr Tyr Asp Pro Tyr Val Asn Tyr
    130                 135                 140
Ser Ser Arg His Thr Ile Thr Gln Pro Phe Ser Tyr His Ser Arg Tyr
145                 150                 155                 160
Phe Thr Pro Lys Pro Val Leu Asp Arg Thr Ile Asp Tyr Phe Gln Pro
                165                 170                 175
```

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro
225             230

<210> SEQ ID NO 18
<211> LENGTH: 702
<212> TYPE: DNA
<213> ORGANISM: Porcine circovirus

<400> SEQUENCE: 18

```
atgacgtatc caaggaggcg tttccgcaga cgaagacacc gcccccgcag ccatcttggc      60
cagatcctcc gctgccgccc ctggctcgtc caccccccgcc accgttaccg ctggagaagg    120
aaaaatggca tcttcaacac ccgcctctcc cgcaccatgg ttatactgt caagaaaacc     180
acagtcagaa cgccctcctg gaatgtggac atgatgagat taatattaa tgatttctt      240
cccccaggag ggggctcaaa ccccctcact gtgcctttg aatactacag aataaggaag     300
gttaaggttg aattctggcc ctgctcccca accacccagg gtgacagggg agtgggctcc    360
actgctgtta ttctagatga taactttgta caaaaggcca atgccctaac ctatgacccc    420
tatgtaaact actcctcccg ccataccata acccagccct ctcctacca ctcccggtac     480
tttaccccga aacctgtcct tgataggaca atcgattact ccaacccaa taacaaaga     540
aatcaactct ggctgagact acaaactact ggaaatgtag accatgtagg cctcggcact    600
gcgttcgaaa acagtatata cgaccaggac tacaatatcc gtataaccat gtatgtacaa    660
ttcagagaat ttaatcttaa agaccccccca cttaaccctt aa                      702
```

<210> SEQ ID NO 19
<211> LENGTH: 234
<212> TYPE: PRT
<213> ORGANISM: Porcine circovirus

<400> SEQUENCE: 19

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Ala Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
            165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 20
<211> LENGTH: 705
<212> TYPE: DNA
<213> ORGANISM: Porcine circovirus

<400> SEQUENCE: 20
atgacgtatc caaggaggcg ttaccgcaga cgaagacacc gcccccgcag ccatcttggc      60
cagatcctcc gccgccgccc ctggctcgtc caccccgcc accgttaccg ctggagaagg     120
aaaaatggca tcttcaacac ccgcctctcc cgcaccatcg ttatactgt caaggctacc     180
acagtcagaa cgcccctg gaatgtggac atgatgagat taatattaa tgattttctt      240
cccccaggag ggggctcaaa ccccctcact gtgcccttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata ccccagccct ctcctacca ctcccggtac     480
tttaccccga aacctgtcct tgataggaca atcgattact ccaacccaa taacaaaga     540
aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa agaccccca cttaacccta agtga                     705

<210> SEQ ID NO 21
<211> LENGTH: 234
<212> TYPE: PRT
<213> ORGANISM: Porcine circovirus

<400> SEQUENCE: 21

Met Thr Tyr Pro Arg Arg Arg Phe Arg Arg Arg Arg His Arg Pro Arg
1               5                   10

```
Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
        130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
210                 215                 220

Asn Leu Lys Asp His Pro Leu Asn Pro Lys
225                 230

<210> SEQ ID NO 22
<211> LENGTH: 705
<212> TYPE: DNA
<213> ORGANISM: Porcine circovirus

<400> SEQUENCE: 22
atgacgtatc caaggaggcg tttccgcaga cgaagacacc gcccccgcag ccatcttggc      60
cagatcctcc gccgccgccc ctggctcgtc caccccgcc accgttaccg ctggagaagg     120
aaaaatggca tcttcaacac ccgcctctcc cgcaccatcg gttatactgt caagaaaacc     180
acagtcagaa cgccctcctg aatgtggaca tgatgagat ttaatattaa tgattttctt      240
cccccaggag ggggctcaaa ccccctcact gtgccctttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata acccagccct ctcctacca ctcccggtac      480 tttaccccga aacctgtcct tgataggaca atcgattact ccaacccaa taacaaaaga     540 aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa agaccaccca cttaaccta agtga                       705

<210> SEQ ID NO 23
<211> LENGTH: 234
<212> TYPE: PRT
<213> ORGANISM: Porcine circovirus

<400> SEQUENCE: 23

Met Thr Tyr Ser Arg Arg Arg Phe Arg Arg

Pro Pro Gly Gly Gly Ser Asn Pro Leu Thr Val Pro Phe Glu Tyr Tyr
              85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Ser Ala Asn
            180                 185                 190

Val Asp His Val Gly Leu Gly Thr Ala Phe Glu Asn Ser Lys Tyr Asp
            195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 24
<211> LENGTH: 705
<212> TYPE: DNA
<213> ORGANISM: Porcine circovirus

<400> SEQUENCE: 24
atgacgtatt ccaggaggcg tttccgcaga agaagacacc gcccccgcag ccatcttggc      60
cagatcctcc gccgccgccc ctggctcgtc caccccgcc accgttaccg ctggagaagg      120
aaaaatggca tcttcaacac ccgcctctcc cgcaccatcg ttatactgt gaagaaaacc      180
acagtcagaa cgccctcctg gaatgtggac atgatgagat taatattaa tgattttctt      240
cccccaggag ggggctcaaa ccccctcact gtgccctttg aatactacag aataaggaag      300
gttaaggttg aattctggcc ctgctcccca atcacccagg gtgacagggg agtgggctcc      360
actgctgtta ttctagatga taactttgta acaaaggcca atgccctaac ctatgacccc      420
tatgtaaact actcctcccg ccataccata cccagccct tctcctacca ctcccggtac      480
tttaccccga aacctgtcct tgataggaca atcgattact ccaacccaa taacaaaaga      540
aatcaactct ggctgagact acaaacctct gcaaatgtag accacgtagg cctcggcact      600
gcgttcgaaa acagtaaata cgaccaggac tacaatatcc gtataaccat gtatgtacaa      660
ttcagagaat ttaatcttaa agaccccca cttaaccccta atga                      705

<210> SEQ ID NO 25
<211> LENGTH: 234
<212> TYPE: PRT
<213> ORGANISM: Porcine circovirus

<400> SEQUENCE: 25

Met Thr Phe Pro Arg Arg Tyr Arg Arg Arg His Arg Pro Arg
1                5                  10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 26
<211> LENGTH: 705
<212> TYPE: DNA
<213> ORGANISM: Porcine circovirus

<400> SEQUENCE: 26

```
atgacgtttc caaggaggcg ttaccgaaga agaagacacc gcccccgcag ccatcttggc    60
cagatcctcc gccgccgccc tggctcgtc  caccccgcc  accgttaccg ctggagaagg   120
aaaaatggca tcttcaacac ccgcctctcc cgcaccatcg ttatactgt  caagaaaacc   180
acagtcagaa cgccctcctg gaatgtggac atgatgagat taatattaa  tgatttctct   240
ccccaggag  ggggctcaaa ccccctcact gtgccctttg aatactacag aataaggaag   300
gttaaggttg aattctggcc ctgctcccca atcacccagg gtgacagggg agtgggctcc   360
actgctgtta ttctagatga taactttgta acaaaggcca atgccctaac ctacgacccc   420
tatgtaaact actcctcccg ccataccata acccagccct ctcctacca  ctcccggtac   480
tttaccccga aacctgtcct tgataggaca atcgattact ccaacccaa  taacaaaaga   540
aatcaactgt ggctgagact acaaactact ggaaatgtag accatgtagg cctcggcact   600
gcgttcgaaa acagtatata cgaccaggac tacaatatcc gtataaccat gtatgtacaa   660
ttcagagaat taatcttaa  agaccccca  cttaacccta atga                   705
```

<210> SEQ ID NO 27
<211> LENGTH: 234
<212> TYPE: PRT
<213> ORGANISM: Porcine circovirus

<400> SEQUENCE: 27

Met Thr Tyr Pro Arg Arg Arg Tyr Arg Lys Arg His Arg Pro Arg
1               5                   10                  15

Ser His Leu Gly Gln Ile Leu Arg Arg Arg Pro Trp Leu Val His Pro
        20                  25                  30

Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 28
<211> LENGTH: 705
<212> TYPE: DNA
<213> ORGANISM: Porcine circovirus

<400> SEQUENCE: 28
atgacgtatc caaggaggcg ttaccggaaa agaagacacc gcccccgcag ccatcttggc      60
cagatcctcc gccgccgccc ctggctcgtc caccccgcc accgttaccg ctggagaagg     120
aaaaatggca tcttcaacac ccgcctctcc cgcaccatcg gttatactgt caagaaaacc     180
acagtcagaa cgccctcctg gaatgtggac atgatgagat taatattaa tgattttctt     240 cccccaggag ggggctcaaa cccctcact gtgccctttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata cccagccct tctcctacca ctcccggtac     480
tttaccccga aacctgtcct tgataggaca atcgattact ccaacccaa taacaaaaga     540 aatcaactgt ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa agacccccca cttaaccta agtga                      705

<210> SEQ ID NO 29
<211> LENGTH: 234
<212> TYPE: PRT
<213> ORGANISM: Porcine circovirus

<400> SEQUENCE: 29

```
Met Thr Tyr Ser Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 30
<211> LENGTH: 705
<212> TYPE: DNA
<213> ORGANISM: Porcine circovirus

<400> SEQUENCE: 30

```
atgacgtatt caaggaggcg tttccgcaga agaagacacc gcccccgcag ccatcttggc      60
cagatcctcc gccgccgccc ctggctcgtc cacccccgcc accgttaccg ctggagaagg     120
aaaaatggca tcttcaacac ccgcctctcc gcaccatcg  gttatactgt caagaaaacc     180
acagtcagaa cgccctcctg gaatgtggac atgatgagat taatattaa  tgattttctt     240
cccccaggag ggggctcaaa ccccctcact gtgccctttg aatactacag aataaggaag     300
gttaaggttg aattctggcc ctgctcccca atcacccagg gtgacagggg agtgggctcc     360
actgctgtta ttctagatga taactttgta acaaaggcca atgccctaac ctatgacccc     420
tatgtaaact actcctcccg ccataccata cccagccct  tctcctacca ctcccggtac     480
tttaccccga aacctgtcct tgataggaca atcgattact ccaacccaa  taacaaaaga     540
aatcaactgt ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa  agaccccca  cttaacccta agtga                    705
```

<210> SEQ ID NO 31
<211> LENGTH: 234
<212> TYPE: PRT
<213> ORGANISM: Porcine circovirus

<400> SEQUENCE: 31

```
Met Thr Tyr Ser Met Arg Arg Phe Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 32
<211> LENGTH: 705
<212> TYPE: DNA
<213> ORGANISM: Porcine circovirus

<400> SEQUENCE: 32

| | |
|---|---|
| atgacgtatt caatgaggcg tttccgcaga cgaagacacc gcccccgcag ccatcttggc | 60 |
| cagatcctcc gccgccgccc ctggctcgtc caccccgcc accgttaccg ctggagaagg | 120 |
| aaaaatggca tcttcaacac ccgcctctcc cgcaccatcg gttatactgt caagaaaacc | 180 |
| acagtcagaa cgccctcctg gaatgtggac atgatgagat taatattaa tgatttttctt | 240 |
| cccccaggag ggggctcaaa cccctcact gtgcccttg aatactacag aataaggaag | 300 |
| gttaaggttg aattctggcc ctgctcccca atcacccagg gtgacagggg agtgggctcc | 360 |
| actgctgtta ttctagatga taactttgta acaaaggcca atgccctaac ctatgacccc | 420 |
| tatgtaaact actcctcccg ccataccata acccagccct ctcctacca ctcccggtac | 480 |
| tttaccccga aacctgtcct tgataggaca atcgattact ccaacccaa taacaaaga | 540 |

```
aatcaactct ggctgagact acaaactact ggaaatgtag accatgtagg cctcggcact    600
gcgttcgaaa acagtatata cgaccaggac tacaatatcc gtataaccat gtatgtacaa    660
ttcagagaat ttaatcttaa agacccccca cttaacccta agtga                    705
```

<210> SEQ ID NO 33
<211> LENGTH: 234
<212> TYPE: PRT
<213> ORGANISM: Porcine circovirus

<400> SEQUENCE: 33

```
Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 34
<211> LENGTH: 702
<212> TYPE: DNA
<213> ORGANISM: Porcine circovirus

<400> SEQUENCE: 34

```
atgacgtatc caaggaggcg tttccgcaga cgaagacacc gcccccgcag ccatcttggc     60
cagatcctcc gccgccgccc ctggctcgtc caccccgcc accgttaccg ctggagaagg    120
aaaaatggca tcttcaacac ccgcctctcc cgcaccatcg gttatactgt caagaaaacc    180
acagtcagaa cgcccctcctg gaatgtggac atgatgagat ttaatattaa tgatttctt    240 cccccaggag ggggctcaaa cccctcact gtgccctttg aatactacag aataaggaag    300
gttaaggttg aattctggcc ctgctcccca atcacccagg gtgacagggg agtgggctcc    360
```

```
actgctgtta ttctagatga taactttgta acaaaggcca atgccctaac ctatgacccc    420
tatgtaaact actcctcccg ccataccata ccccagcccc tctcctacca ctcccgctat    480 ttcacccccca aacctgtcct tgataggaca atcgattact ccaacccaa taacaaaaga    540
```
*(note: line 540 as visible)*

```
aatcaactct ggctgagact acaaactact ggaaatgtag accatgtagg cctcggcact    600
gcgttcgaaa acagtatata cgaccaggac tacaatatcc gtataaccat gtatgtacaa    660
ttcagagaat ttaatcttaa agaccccca cttaaccta ag                          702
```

<210> SEQ ID NO 35
<211> LENGTH: 233
<212> TYPE: PRT
<213> ORGANISM: Porcine circovirus

<400> SEQUENCE: 35

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Asn Pro
225                 230
```

<210> SEQ ID NO 36
<211> LENGTH: 702
<212> TYPE: DNA
<213> ORGANISM: Porcine circovirus

<400> SEQUENCE: 36

```
atgacgtatc caaggaggcg ttaccggaga agaagacacc gccccgcag ccatcttggc     60 cagatcctcc gccgccgccc ctggctcgtc caccccgcc accgttaccg ctggagaagg    120
aaaaatggca tcttcaacac ccgcctctcc cgcaccatcg gttatactgt caagaaaacc    180
```

```
acagtcagaa cgccctcctg gaatgtggac atgatgagat ttaatattaa tgattttctt    240
cccccaggag ggggctcaaa cccctcact gtgcccttg aatactacag aataaggaag      300
```

```
acagtcagaa cgccctcctg gaatgtggac atgatgagat ttaatattaa tgattttctt    240
cccccaggag ggggctcaaa cccctcact gtgcccttg aatactacag aataaggaag      300
gttaaggttg aattctggcc ctgctcccca atcacccagg gtgacagggg agtgggctcc    360
actgctgtta ttctagatga taactttgta acaaaggcca atgccctaac ctatgacccc   420
tatgtaaact actcctcccg ccataccata acccagccct tctcctacca ctcccggtac   480
tttaccccga aacctgtcct tgataggaca atcgattact ccaacccaa taacaaaaga    540 aatcaactct ggctgagact acaaactact ggaaatgtag accatgtagg cctcggcact   600
gcgttcgaaa acagtatata cgaccaggac tacaatatcc gtgtaaccat gtatgtacaa   660
ttcagagaat ttaatcttaa agacccccca cttaaccctt aa                      702
```

<210> SEQ ID NO 37
<211> LENGTH: 234
<212> TYPE: PRT
<213> ORGANISM: Porcine circovirus

<400> SEQUENCE: 37

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Val Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 38
<211> LENGTH: 705
<212> TYPE: DNA
<213> ORGANISM: Porcine circovirus

<400> SEQUENCE: 38

```
atgacgtatc caaggaggcg tttccgcaga cgaagacacc gccccgcag ccatcttggc    60
cagatcctcc gccgccgccc ctggctcgtc caccccgcc accgttaccg ctggagaagg   120
aaaaatggca tcttcaacac ccgcctctcc cgcaccatcg gttatactgt caagaaaacc   180
acagtcagaa cgccctcctg gaatgtggac atggtgagat taatattaa tgattttctt   240
cccccaggag ggggctcaaa ccccctcact gtgcccttg aatactacag aataaggaag   300
gttaaggttg aattctggcc ctgctcccca atcacccagg gtgacagggg agtgggctcc   360
actgctgtta ttctagatga taactttgta acaaaggcca atgccctaac ctatgacccc   420
tatgtaaact actcctcccg ccataccata acccagcct tctcctacca ctcccggtac   480
tttacccccga aacctgtcct tgataggaca atcgattact ccaacccaa taacaaaga   540
aatcaactct ggctgagact acaaactact ggaaatgtag accatgtagg cctcggcact   600
gcgttcgaaa acagtatata cgaccaggac tacaatatcc gtataacgat gtatgtacaa   660
ttcagagaat taatcttaa agaccccca cttaaccta agtga             705
```

<210> SEQ ID NO 39
<211> LENGTH: 234
<212> TYPE: PRT
<213> ORGANISM: Porcine circovirus

<400> SEQUENCE: 39

```
Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Ala Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Gly Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230
```

<210> SEQ ID NO 40
<211> LENGTH: 705
<212> TYPE: DNA
<213> ORGANISM: Porcine circovirus

<400> SEQUENCE: 40

```
atgacgtatc caaggaggcg tttccgcaga cgaagacacc gcccccgcag ccatcttggc    60
cagatcctcc gccgccgccc ctggctcgtc caccccgcc accgttaccg ctggagaagg    120
aaaaatggca tcttcaacac ccgcctctcc cgcaccatcg gttatactgt caagaaaacc    180
acagtcagaa cgccctcctg gaatgtggac atgatgagat taatattaa tgattttctt     240
cccccaggag ggggctcaaa ccccctcact gtgccctttg aatactacag aataaggaag    300
gttaaggttg aattctggcc ctgctcccca atcacccagg gtgacagggg agtgggctcc    360
actgctgtta ttctagatga taactttgta gcaaaggcca atgccctaac ctatgacccc    420
tatgtaaact actcctcccg ccataccata acccagccct ctcctacca ctcccggtac    480
tttaccccga aacctgtcct tgatgggaca atcgattact ccaacccaa taacaaaaga    540
aatcaactct ggctgagact acaaactact ggaaatgtag accatgtagg cctcggcact    600
gcgttcgaaa acagtatata cgaccaggac tacaatatcc gtaaccat gtatgtacaa      660
ttcagagaat taaccttaa agacccccca cttaacccta agtga                    705
```

<210> SEQ ID NO 41
<211> LENGTH: 233
<212> TYPE: PRT
<213> ORGANISM: Porcine circovirus

<400> SEQUENCE: 41

```
Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
```

Asn Leu Lys Asp Pro Pro Leu Lys Pro
225                 230

<210> SEQ ID NO 42
<211> LENGTH: 718
<212> TYPE: DNA
<213> ORGANISM: Porcine circovirus

<400> SEQUENCE: 42

```
atgacgtatc caaggaggcg tttccgcaga cgaagacacc gcccccgcag ccatcttggc      60
cagatcctcc gccgccgccc ctggctcgtc caccccccgcc accgttaccg ctggagaagg    120
aaaaatggca tcttcaacac ccgcctctcc cgcaccatcg gttatactgt caaaaaaacc    180
acagtcagaa cgccctcctg gaatgtggac atgatgagat ttaatattaa tgatttctt    240
cccccaggag ggggctcaaa ccccctcact gtgccctttg aatactacag aataagaaag    300
gttaaggttg aattctggcc ctgctcccca atcacccagg gtgacagggg agtgggctcc    360
actgctgtta ttctagatga taactttgta acaaaggcca atgccctaac ctatgacccc    420
tatgtaaact actcctcccg ccataccata cccagccct ctcctacca ctcccggtac      480
tttaccccga aacctgtcct tgataggaca atcgattact ccaaccaaa taacaaaga     540
aatcaactct ggctgagact acaaactact ggaaatgtag accatgtagg cctcggcact    600
gcgttcgaaa acagtatata cgaccaggac tacaatatcc gtataaccat gtatgtacaa    660
ttcagagaat ttaatcttaa agaccccccca cttaaaccct aaatgaataa taaaaacc     718
```

<210> SEQ ID NO 43
<211> LENGTH: 233
<212> TYPE: PRT
<213> ORGANISM: Porcine circovirus

<400> SEQUENCE: 43

Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn

```
                180             185             190
Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
            210                 215                 220

Asn Leu Lys Asp Pro Pro Leu Lys Pro
225                 230

<210> SEQ ID NO 44
<211> LENGTH: 699
<212> TYPE: DNA
<213> ORGANISM: Porcine circovirus

<400> SEQUENCE: 44
atgacgtatc caaggaggcg tttccgcaga cgaagacacc gcccccgcag ccatcttggc     60
cagatcctcc gccgccgccc ctggctcgtc caccccccgcc accgttaccg ctggagaagg    120
aaaaatggca tcttcaacac ccgcctctcc cgcaccatcg gttatactgt caaaaaaacc    180
acagtcagaa cgccctcctg aatgtggac atgatgagat ttaatattaa tgattttctt     240
cccccaggag ggggctcaaa ccccctcact gtgcccttg aatactacag aataagaaag     300
gttaaggttg aattctggcc ctgctcccca atcacccagg gtgacagggg agtgggctcc    360
actgctgtta ttctagatga taactttgta acaaaggcca atgcctaac ctatgacccc     420 tatgtaaact actcctcccg ccataccata acccagccct ctcctacca ctcccggtac     480 tttaccccga aacctgtcct tgataggaca atcgattact ccaaccaaa taacaaaga     540 aatcaactct ggctgagact acaaactact ggaaatgtag accatgtagg cctcggcact    600
gcgttcgaaa acagtatata cgaccaggac tacaatatcc gtataaccat gtatgtacaa    660
ttcagagaat ttaatcttaa agacccccca cttaaaccc                            699

<210> SEQ ID NO 45
<211> LENGTH: 233
<212> TYPE: PRT
<213> ORGANISM: Porcine circovirus

<400> SEQUENCE: 45

Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Thr Val Arg Thr
            50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
            130                 135                 140

Ser Ser Arg His Thr Ile Thr Gln Pro Phe Ser Tyr His Ser Arg Tyr
```

```
              145                 150                 155                 160
         Phe Thr Pro Lys Pro Val Leu Asp Arg Thr Ile Asp Tyr Phe Gln Pro
                         165                 170                 175

Asn Asn Lys Arg Asn Gln Leu Trp Leu Arg Leu Gln Thr Thr Gly Asn
                         180                 185                 190

Val Asp His Val Gly Leu Gly Thr Ala Phe Glu Asn Ser Ile Tyr Asp
                         195                 200                 205

Gln Asp Tyr Asn Ile Arg Ile Thr Met Tyr Val Gln Phe Arg Glu Phe
                         210                 215                 220

Asn Leu Lys Asp Pro Pro Leu Lys Pro
         225                 230
```

<210> SEQ ID NO 46
<211> LENGTH: 699
<212> TYPE: DNA
<213> ORGANISM: Porcine circovirus

<400> SEQUENCE: 46

```
atgacgtatc caaggaggcg tttccgcaga cgaagacacc gcccccgcag ccatcttggc     60
cagatcctcc gccgccgccc ctggctcgtc caccccccgcc accgttaccg ctggagaagg    120
aaaaatggca tcttcaacac ccgcctctcc cgcaccatcg gttatactgt caaaaaaacc    180
acagtcagaa cgccctcctg gaatgtggac atgatgagat taatattaa tgattttctt      240
cccccaggag ggggctcaaa cccctcact  gtgccctttg aatactacag aataagaaag     300
gttaaggttg aattctggcc ctgctcccca atcacccagg gtgacagggg agtgggctcc    360
actgctgtta ttctagatga taactttgta acaaaggcca atgcctaac  ctatgacccc     420
tatgtaaact actcctcccg ccataccata cccagccct  tctcctacca ctcccggtac    480
tttaccccga aacctgtcct tgataggaca atcgattact ccaaccaaa  taacaaaaga    540
atcaactct  ggctgagact acaaactact ggaaatgtag accatgtagg cctcggcact    600
gcgttcgaaa acagtatata cgaccaggac tacaatatcc gtataaccat gtatgtacaa    660
ttcagagaat taatcttaa  agacccccca cttaaaccc                            699
```

<210> SEQ ID NO 47
<211> LENGTH: 233
<212> TYPE: PRT
<213> ORGANISM: Porcine circovirus

<400> SEQUENCE: 47

```
         Met Thr Tyr Pro Arg Arg Arg Phe Arg Arg Arg His Arg Pro Arg
         1               5                   10                  15

Ser His Leu Gly Gln Ile Leu Arg Arg Arg Pro Trp Leu Val His Pro
                         20                  25                  30

Arg His Arg Tyr Arg Trp Arg Arg Lys Asn Gly Ile Phe Asn Thr Arg
                     35                  40                  45

Leu Ser Arg Thr Ile Gly Tyr Thr Val Lys Lys Thr Thr Val Arg Thr
              50                  55                  60

Pro Ser Trp Asn Val Asp Met Met Arg Phe Asn Ile Asn Asp Phe Leu
         65                  70                  75                  80

Pro Pro Gly Gly Gly Ser Asn Pro Leu Thr Val Pro Phe Glu Tyr Tyr
                         85                  90                  95

Arg Ile Arg Lys Val Lys Val Glu Phe Trp Pro Cys Ser Pro Ile Thr
                     100                 105                 110

Gln Gly Asp Arg Gly Val Gly Ser Thr Ala Val Ile Leu Asp Asp Asn
```

```
                 115                 120                 125
        Phe Val Thr Lys Ala Asn Ala Leu Thr Tyr Asp Pro Tyr Val Asn Tyr
            130                 135                 140

Ser Ser Arg His Thr Ile Thr Gln Pro Phe Tyr His Ser Arg Tyr
        145                 150                 155                 160

Phe Thr Pro Lys Pro Val Leu Asp Arg Thr Ile Asp Tyr Phe Gln Pro
                        165                 170                 175

Asn Asn Lys Arg Asn Gln Leu Trp Leu Arg Leu Gln Thr Thr Gly Asn
                    180                 185                 190

Val Asp His Val Gly Leu Gly Thr Ala Phe Glu Asn Ser Ile Tyr Asp
                    195                 200                 205

Gln Asp Tyr Asn Ile Arg Ile Thr Met Tyr Val Gln Phe Arg Glu Phe
            210                 215                 220

Asn Leu Lys Gly Pro Pro Leu Lys Pro
        225                 230

<210> SEQ ID NO 48
<211> LENGTH: 699
<212> TYPE: DNA
<213> ORGANISM: Porcine circovirus

<400> SEQUENCE: 48
atgacgtatc caaggaggcg tttccgcaga cgaagacacc gcccccgcag ccatcttggc      60
cagatcctcc gccgccgccc ctggctcgtc caccccccgcc accgttaccg ctggagaagg    120
aaaaatggca tcttcaacac ccgcctctcc cgcaccatcg gttatactgt caaaaaaacc    180
acagtcagaa cgcctcctg gaatgtggac atgatgagat taatattaa tgattttctt      240 ccccaggag ggggctcaaa ccccctcact gtgccctttg aatactacag aataagaaag    300
gttaaggttg aattctggcc ctgctcccca atcacccagg gtgacagggg agtgggctcc   360
actgctgtta ttctagatga taactttgta acaaaggcca atgccctaac ctatgacccc   420 tatgtaaaact actcctcccg ccataccata acccagccct tctcctacca ctcccggtac   480
tttaccccga aacctgtcct tgataggaca atcgattact ccaaccaaa taacaaaaga   540 aatcaactct ggctgagact acaaactact ggaaatgtag accatgtagg cctcggcact   600
gcgttcgaaa acagtatata cgaccaggac tacaatatcc gtataaccat gtatgtacaa   660
ttcagagaat taatcttaa gggccccca cttaaaccc                              699

<210> SEQ ID NO 49
<211> LENGTH: 233
<212> TYPE: PRT
<213> ORGANISM: Porcine circovirus

<400> SEQUENCE: 49

Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Thr Val Arg Thr
        50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
```

85                  90                  95
Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
                180                 185                 190

Val Asp His Val Gly Leu Gly Thr Ala Phe Glu Asn Ser Ile Tyr Asp
                195                 200                 205

Gln Asp Tyr Asn Ile Arg Ile Thr Met Tyr Val Gln Phe Arg Glu Phe
            210                 215                 220

Asn Leu Lys Gly Pro Pro Leu Lys Pro
225                 230

<210> SEQ ID NO 50
<211> LENGTH: 699
<212> TYPE: DNA
<213> ORGANISM: Porcine circovirus

<400> SEQUENCE: 50
atgacgtatc caaggaggcg tttccgcaga cgaagacacc gcccccgcag ccatcttggc        60
cagatcctcc gccgccgccc ctggctcgtc caccccgcc accgttaccg ctggagaagg        120
aaaaatggca tcttcaacac ccgcctctcc cgcaccatcg gttatactgt caaaaaaacc        180
acagtcagaa cgcccctg gaatgtggac atgatgagat taatattaa tgatttttctt         240 cccccaggag ggggctcaaa cccctcact gtgcccttg aatactacag aataagaaag        300
gttaaggttg aattctggcc ctgctcccca atcacccagg gtgacagggg agtgggctcc       360
actgctgtta ttctagatga taactttgta acaaaggcca atgccctaac ctatgacccc      420
tatgtaaact actcctcccg ccataccata cccagccct tctcctacca ctcccggtac        480 tttacccga aacctgtcct tgataggaca atcgattact ccaaccaaa taacaaaaga        540 aatcaactct ggctgagact acaaactact ggaaatgtag accatgtagg cctcggcact      600
gcgttcgaaa acagtatata cgaccaggac tacaatatcc gtataaccat gtatgtacaa      660
ttcagagaat ttaatcttaa gggccccca cttaaaccc                              699

<210> SEQ ID NO 51
<211> LENGTH: 233
<212> TYPE: PRT
<213> ORGANISM: Porcine circovirus

<400> SEQUENCE: 51

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr

```
            50                  55                  60
Pro Ser Trp Asn Val Asp Met Met Arg Phe Asn Ile Asn Asp Phe Leu
 65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Gly Pro Pro Leu Lys Pro
225                 230

<210> SEQ ID NO 52
<211> LENGTH: 699
<212> TYPE: DNA
<213> ORGANISM: Porcine circovirus

<400> SEQUENCE: 52
atgacgtatc caaggaggcg tttccgcaga cgaagacacc gcccccgcag ccatcttggc      60
cagatcctcc gccgccgccc ctggctcgtc cacccccgcc accgttaccg ctggagaagg     120
aaaaatggca tctttaacac ccgcctctcc cgcaccatcg gttatactgt caaaaaaacc     180
acagtcagaa cgccctcctg gaatgtggac atgatgagat taatattaa tgattttctt     240 cccccaggag ggggctcaaa ccccctcact gtgccctttg aatactacag aataagaaag     300
gttaaggttg aattctggcc ctgctcccca atcacccagg tgacagggg agtgggctcc     360 actgctgtta ttctagatga taactttgta acaaaggcca atgccctaac ctatgacccc     420
tatgtaaact actcctcccg ccataccata acccagccct ctcctacca ctcccggtac     480 tttaccccga aacctgtcct tgataggaca atcgattact ccaaccaaa taacaaaga     540 aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa gggcccccca cttaaaccc                             699

<210> SEQ ID NO 53
<211> LENGTH: 233
<212> TYPE: PRT
<213> ORGANISM: Porcine circovirus

<400> SEQUENCE: 53

Met Thr Tyr Pro Arg Arg Arg Ph

```
                20                  25                  30
Arg His Arg Tyr Arg Trp Arg Arg Lys Asn Gly Ile Phe Asn Thr Arg
            35                  40                  45

Leu Ser Arg Thr Ile Gly Tyr Thr Val Lys Lys Thr Thr Val Arg Thr
 50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
            130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
            210                 215                 220

Asn Leu Lys Gly Pro Pro Leu Lys Pro
225                 230

<210> SEQ ID NO 54
<211> LENGTH: 699
<212> TYPE: DNA
<213> ORGANISM: Porcine circovirus

<400> SEQUENCE: 54
atgacgtatc caaggaggcg tttccgcaga cgaagacacc gcccccgcag ccatcttggc      60
cagatcctcc gccgccgccc ctggctcgtc caccccgcc accgttaccg ctggagaagg     120
aaaaatggca tcttcaacac ccgcctctcc cgcaccatcg ttatactgt caaaaaaacc     180 acagtcagaa cgccctcctg gaatgtggac atgatgagat taatattaa tgattttctt     240 cccccaggag ggggctcaaa ccccctcact gtgcccttg aatactacag aataagaaag     300
gttaaggttg aattctggcc ctgctcccca tcacccagg gtgacagggg agtgggctcc     360
actgctgtta ttctagatga taactttgta caaaaggcca atgccctaac ctatgacccc     420
tatgtaaact actcctcccg ccataccata cccagccct ctcctacca ctcccggtac      480 tttaccccga aacctgtcct tgataggaca atcgattact ccaaccaaa taacaaaga     540 aatcaactct ggctgagact acaaactact ggaaatgtag accatgtagg cctcggcact     600
gcgttcgaaa acagtatata cgaccaggac tacaatatcc gtataaccat gtatgtacaa     660
ttcagagaat taatcttaa gggccccca cttaaaccc                                699

<210> SEQ ID NO 55
<211> LENGTH: 234
<212> TYPE: PRT
<213> ORGANISM: Porcine circovirus
```

<400> SEQUENCE: 55

Met Thr Tyr Pro Arg Arg Phe Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Lys Asn Gly Ile Phe Asn Thr Arg
        35                  40                  45

Leu Ser Arg Thr Ile Gly Tyr Thr Val Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
                115                 120                 125

Phe Val Thr Lys Ala Asn Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Gly Thr Ile Asp Tyr Phe Gln Pro
                165                 170                 175

Asn Asn Lys Arg Asn Gln Leu Trp Leu Arg Leu Gln Thr Thr Gly Asn
                180                 185                 190

Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
        210                 215                 220

Asn Leu Lys Asp Pro Pro Leu Asn Pro Lys
225                 230

<210> SEQ ID NO 56
<211> LENGTH: 705
<212> TYPE: DNA
<213> ORGANISM: Porcine circovirus

<400> SEQUENCE: 56
atgacgtatc caaggaggcg tttccgcaga cgaagacacc gcccccgcag ccatcttggc    60
cagatcctcc gccgccgccc ctggctcgtc caccccgcc accgttaccg ctggagaagg   120
aaaaatggca tcttcaacac ccgcctctcc cgcaccatcg gttatactgt caagaaaacc   180
acagtcagaa cgccctcctg gaatgtggac atgatgagat taatattaa tgattttctt   240
cccccaggag ggggctcaaa ccccctcact gtgccctttg aatactacag aataaggaag   300
gttaaggttg aattctggcc ctgctcccca atcacccagg gtgacagggg agtgggctcc   360
actgctgtta ttctagatga taactttgta acaaaggcca atgccctaac ctatgacccc   420
tatgtaaact actcctcccg ccataccata acccagccct ctcctacca ctcccggtac   480
tttaccccga aacctgtcct tgatgggaca atcgattact ccaacccaa taacaaaaga   540
aatcaactct ggctgagact acaaactact ggaaatgtag accatgtagg cctcggcact   600
gcgttcgaaa acagtatata cgaccaggac tacaatatcc gtataaccat gtatgtacaa   660
ttcagagaat taatcttaa agacccccca cttaacccta agtga                    705

<210> SEQ ID NO 57
<211> LENGTH: 1767
<212> TYPE: DNA
<213> ORGANISM: Porcine circovirus

<400> SEQUENCE: 57

| | | | | | |
|---|---|---|---|---|---|
| aaatttctga | caaacgttac | agggtgctgc | tctgcaacgg | tcaccagact | cccgctctcc | 60 |
| aacaaggtac | tcacagcagt | agacaggtca | ctgcgttgtc | cttgagatct | aggagctcca | 120 |
| cactcgataa | gtaagttgcc | ttctttactg | cagtattctt | tattctgctg | gtctgttcct | 180 |
| ttcgctttct | cgatgtggca | gcgggcacca | aataccact | tcactttatt | aaaagtttgc | 240 |
| ttcttcacaa | aattagcgaa | ccctgtagg | tggggtgttc | ggccttcctc | attaccctcc | 300 |
| tcgccaacaa | taaataatc | aaataggag | attgggagct | cccgtatttt | cttgcgctcg | 360 |
| tcttcggaag | gattattgag | agtgaacacc | caccttttat | gtggttgggg | tccgcttctt | 420 |
| ccattcttct | tactgggcat | gttgctgctg | aggtgctgcc | gaggtgctgc | cgctgccgaa | 480 |
| gtgcgctggt | aatacttaca | gcgcacttct | ttcgttttca | gctatgacgt | atccaaggag | 540 |
| gcgtttccgc | agacgaagac | accgcccccg | cagccatctt | ggccagatcc | tccgccgccg | 600 |
| cccctggctc | gtccaccccc | gccaccgtta | ccgctggaga | aggaaaaatg | gcatcttcaa | 660 |
| cacccgcctc | tcccgcacca | tcggttatac | tgtcaagaaa | accacagtca | gaacgccctc | 720 |
| ctggaatgtg | gacatgatga | gatttaatat | taatgatttt | cttcccccag | gaggggggctc | 780 |
| aaacccctc | actgtgccct | ttgaatacta | cagaataagg | aaggttaagg | ttgaattctg | 840 |
| gccctgctcc | ccaatcaccc | aggtgacag | gggagtgggc | tccactgctg | ttattctaga | 900 |
| tgataacttt | gtaacaaagg | ccaatgccct | aacctatgac | ccctatgtaa | actactcctc | 960 |
| ccgccatacc | ataacccagc | ccttctccta | ccactcccgg | tactttaccc | cgaaacctgt | 1020 |
| ccttgatggg | acaatcgatt | acttccaacc | caataacaaa | agaaatcaac | tctggctgag | 1080 |
| actacaaact | actggaaatg | tagaccatgt | aggcctcggc | actgcgttcg | aaaacagtat | 1140 |
| atacgaccag | gactacaata | tccgtataac | catgtatgta | caattcagag | aatttaatct | 1200 |
| taaagacccc | ccacttaacc | ctaagtgaat | aataaaaacc | attacgaagt | gataaaaaag | 1260 |
| actcagtaat | ttatttcata | tggaaattca | gggcatgggg | gggaaagggt | gacgaactgg | 1320 |
| cccccttcct | ccgtggattg | ttctgtagca | ttcttccaaa | ataccaagga | agtaatcctc | 1380 |
| cgatagagag | cttctacagc | taggacagca | gttgaggagt | accattccaa | cggggtctga | 1440 |
| ttgctggtaa | tcagaatact | gcgggccaaa | aaaggtacag | ttccaccttt | agtctctaca | 1500 |
| gtcaatggat | atcgatcaca | cagtctcagt | agatcatccc | acggcagcca | accataaaag | 1560 |
| tcatcaataa | caaccacttc | ttcaccatgg | taaccatccc | accacttgtt | tcgaggtggt | 1620 |
| ttccagtatg | tggtttccgg | gtctgcaaaa | ttagcagccc | atttgctttt | accacaccca | 1680 |
| ggtggcccca | caatgacgtg | tacattggtc | ttccaatcac | gcttctgcat | tttcccgctc | 1740 |
| actttcaaaa | gttcagccag | cccgcgg | | | | 1767 |

<210> SEQ ID NO 58
<211> LENGTH: 233
<212> TYPE: PRT
<213> ORGANISM: Porcine circovirus

<400> SEQUENCE: 58

Met Thr Tyr Pro Arg Arg Arg Tyr Arg Arg Arg His Arg Pro Arg
1               5                   10                  15

```
Ser His Leu Gly Gln Ile Leu Arg Arg Arg Pro Trp Leu Val His Pro
            20                  25                  30

Arg His Arg Tyr Arg Trp Arg Lys Asn Gly Ile Phe Asn Thr Arg
        35                  40                  45

Leu Ser Arg Thr Phe Gly Tyr Thr Val Lys Ala Thr Thr Val Arg Thr
50                  55                  60

Pro Ser Trp Ala Val Asp Met Met Arg Phe Asn Ile Asp Asp Val Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
210                 215                 220

Asn Leu Lys Asp Pro Pro Leu Lys Pro
225                 230

<210> SEQ ID NO 59
<211> LENGTH: 702
<212> TYPE: DNA
<213> ORGANISM: Porcine circovirus

<400> SEQUENCE: 59
atgacgtatc caaggaggcg ttaccgcaga agaagacacc gcccccgcag ccatcttggc      60
cagatcctcc gccgccgccc ctggctcgtc caccccgcc accgctaccg ttggagaagg     120
aaaaatggca tcttcaacac ccgcctctcc cgcaccttcg gatatactgt caaggctacc    180
acagtcagaa cgccctcctg gcggtggac atgatgagat taatattga cgactttgtt     240 cccccgggag ggggaccaa caaaatctct ataccctttg aatactacag aataagaaag     300
gttaaggttg aattctggcc ctgctccccc atcacccagg gtgatagggg agtgggctcc    360
actgctgtta ttctagatga taactttgta acaaaggcca cagccctaac ctatgaccca    420
tatgtaaact actcctcccg ccatacaatc cccaaccct ctcctacca ctcccgttac     480 ttcacaccca aacctgttct tgactccacc attgattact ccaaccaaa taacaaaagg    540 aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat ttaatcttaa agaccccca cttaaccct aa                         702

<210> SEQ ID NO 60
<211> LENGTH: 233
<212> TYPE: PRT
<213> ORGANISM: Porcine circovirus
```

<400> SEQUENCE: 60

```
Met Thr Tyr Pro Arg Arg Tyr Arg Arg Arg His Arg Pro Arg
1               5                   10                  15

Ser His Leu Gly Gln Ile Leu Arg Arg Pro Trp Leu Leu His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Arg Thr Thr Val Thr Thr
    50                  55                  60

Pro Ser Trp Ala Val Asp Met Met Arg Phe Lys Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Gly Asn
            180                 185                 190

Val Asp His Val Gly Leu Gly Ile Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 61
<211> LENGTH: 702
<212> TYPE: DNA
<213> ORGANISM: Porcine circovirus

<400> SEQUENCE: 61

| | | |
|---|---|---|
| atgacgtatc caaggaggcg ttaccgcaga agaagacacc gcccccgcag ccatcttggc | 60 |
| cagatcctcc gccgccgccc ctggctcctc caccccgcc accgctaccg ttggagaagg | 120 |
| aaaaatggca tcttcaacac ccgcctctcc cgcaccttcg gatatactgt caagcgtacc | 180 |
| acagtcacaa cgccctcctg gcggtggac atgatgagat taaaattga cgactttgtt | 240 |
| cccccgggag gggggaccaa caaaatctct atacccttg aatactacag aataagaaag | 300 |
| gttaaggttg aattctggcc ctgctccccc atcacccagg gtgataggg agtgggctcc | 360 |
| actgctgtta ttctagatga taactttgta acaaaggcca cagccctaac ctatgaccca | 420 |
| tatgtaaact actcctcccg ccatacaatc cccaaccct ctcctacca ctcccgttac | 480 |
| ttcacaccca aacctgttct tgactccact attgattact ccaaccaaa taacaaaagg | 540 |
| aatcagcttt ggctgaggct acaaacctct ggaaatgtgg accacgtagg cctcggcatt | 600 |
| gcgttcgaaa acagtaaata cgaccaggac tacaatatcc gtgtaaccat gtatgtacaa | 660 |
| ttcagagaat taatcttaa agaccccca cttaaaccct aa | 702 |

<210> SEQ ID NO 62
<211> LENGTH: 233
<212> TYPE: PRT
<213> ORGANISM: Porcine circovirus

<400> SEQUENCE: 62

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Ile Lys Arg Thr Thr Val Arg Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro
225                 230

<210> SEQ ID NO 63
<211> LENGTH: 702
<212> TYPE: DNA
<213> ORGANISM: Porcine circovirus

<400> SEQUENCE: 63
atgacgtatc caaggaggcg ttaccggaga agaagacacc gccccgcag ccatcttggc      60 cagatcctcc gccgccgccc ctggctcgtc caccccgcc accgttaccg ctggagaagg     120
aaaaatggca tcttcaacac ccgcctatcc cgcaccttcg gatatactat caagcgaacc    180
acagtcagaa cgccctcctg ggcggtggac atgatgagat tcaatattaa tgactttctt    240
cccccaggag ggggctcaaa ccccgctct gtgccctttg aatactacag aataagaaag    300
gttaaggttg aattctggcc ctgctcccg atcacccagg gtgacagggg agtgggctcc     360
agtgctgtta ttctagatga taactttgta acaaggccca cagccctcac ctatgacccc   420
tatgtaaact actcctcccg ccataccata cccagccct ctcctaccca ctcccgctac    480
tttaccccca aacctgtcct agattccact attgattact ccaaccaaa caacaaaga    540

| | |
|---|---|
| aaccagctgt ggctgagact acaaactgct ggaaatgtag accacgtagg cctcggcact | 600 |
| gcgttcgaaa acagtatata cgaccaggaa tacaatatcc gtgtaaccat gtatgtacaa | 660 |
| ttcagagaat ttaatcttaa agaccccccca cttaaccctt aa | 702 |

<210> SEQ ID NO 64
<211> LENGTH: 234
<212> TYPE: PRT
<213> ORGANISM: Porcine circovirus

<400> SEQUENCE: 64

Met Thr Tyr Pro Arg Arg Arg Tyr Arg Arg Arg His Arg Pro Arg
1               5                   10                  15
Ser His Leu Gly His Ile Leu Arg Arg Arg Pro Trp Leu Val His Pro
            20                  25                  30
Arg His Arg Tyr Arg Trp Arg Arg Lys Asn Gly Ile Phe Asn Ala Arg
        35                  40                  45
Leu Ser Arg Ser Phe Val Tyr Thr Val Asn Ala Ser Gln Val Ser Pro
    50                  55                  60
Pro Ser Trp Ala Val Asp Met Met Arg Phe Asn Ile Asn Gln Phe Leu
65                  70                  75                  80
Pro Pro Gly Gly Gly Ser Asn Pro Leu Thr Val Pro Phe Glu Tyr Tyr
                85                  90                  95
Arg Ile Arg Lys Val Lys Val Glu Phe Ala Arg Ser Pro Ile Thr
            100                 105                 110
Gln Gly Asp Arg Gly Val Gly Ser Thr Ala Val Ile Leu Asn Asp Asn
        115                 120                 125
Phe Val Thr Lys Ala Thr Ala Leu Thr Tyr Asp Pro Tyr Val Asn Tyr
    130                 135                 140
Ser Ser Arg His Thr Ile Thr Gln Pro Phe Ser Tyr His Ser Arg Tyr
145                 150                 155                 160
Phe Thr Pro Lys Pro Val Leu Asp Ser Thr Ile Asp Tyr Phe Gln Pro
                165                 170                 175
Asn Asn Lys Arg Asn Gln Leu Trp Met Arg Leu Gln Thr Thr Gly Asn
            180                 185                 190
Val Asp His Val Gly Leu Gly His Ala Phe Gln Asn Ser Thr Asn Ala
        195                 200                 205
Gln Ala Tyr Asn Val Arg Val Thr Met Tyr Val Gln Phe Arg Glu Phe
    210                 215                 220
Asn Leu Lys Asp Pro Pro Leu Asn Pro Lys
225                 230

<210> SEQ ID NO 65
<211> LENGTH: 705
<212> TYPE: DNA
<213> ORGANISM: Porcine circovirus

<400> SEQUENCE: 65

| | |
|---|---|
| atgacgtatc caaggaggcg ttaccggaga agaagacacc gccccccgcag ccatcttggc | 60 |
| catatcctcc gccgccgccc ctggctcgtc caccccccgcc accgctaccg ttggagaagg | 120 |
| aaaaatggaa tcttcaatgc ccgcctctcc cgctcctttg tttataccgt taatgcctca | 180 |
| caggtctcac caccctcttg ggcggtggac atgatgagat ttaatattaa ccaatttctt | 240 |
| cccccaggag ggggctcaaa ccccctcact gtgccctttg aatactacag aataagaaag | 300 |
| gttaaagtgg aattctttgc aagatccccc atcacccaag gtgacagggg agtgggctcc | 360 |

```
actgctgtta ttctaaatga taactttgta acaaaggcca cagccctaac ctatgacccc    420
tatgtaaact actcctcccg ccataccata acccaccct tctcctacca ctcccgctac     480
tttaccccca aacctgtcct tgattccact attgattact tccaaccaaa taacaaaaga   540
aatcagctgt ggatgagact acaaactact ggaaatgtag accatgtagg cctcggacac   600
gcctttcaaa acagtacaaa tgcccaggcc tacaatgtcc gtgtaaccat gtatgtacaa   660
ttcagagaat ttaatcttaa agaccccca  cttaaccta agtga                     705

<210> SEQ ID NO 66
<211> LENGTH: 1767
<212> TYPE: DNA
<213> ORGANISM: Porcine circovirus

<400> SEQUENCE: 66 gtcttttta tcacttcgta atggttttta ttattcactt agggttaagt gggggggtctt    60 taagattaaa ttctctgaat tgtacataca tggttatacg atattgtag tcctggtcgt    120 atatactgtt ttcgaacgca gtgccgaggc ctacatggtc tacatttcca gtagtttgta   180
gtctcagcca gagttgattt cttttgttat tgggttggaa gtaatcgatt gtcctatcaa   240
ggacaggttt cggggtaaag taccgggagt ggtaggagaa gggctgggtt atggtatggc   300
gggaggagta gtttacatag gggtcatagg ttagggcatt ggcctttgtt acaaagttat   360
catctagaat aacagcagtg agcccactc ccctgtcacc ctgggtgatt ggggagcagg    420
gccagaattc aaccttaacc ttccttattc tgtagtattc aaagggcaca gtgagggggt   480
ttgagccccc tcctgggga  agaaaatcat taatattaaa tctcatcatg tccacattcc    540
aggagggcgt tctgactgtg gttttcttga cagtataacc gatggtgcgg agagggcggg   600
tgttgaagat gccatttttc cttctccagc ggtaacggtg gcggggtgg  acgagccagg    660 ggcggcggcg gaggatctgg ccaagatggc tgcgggggcg gtgtcttcgt ctgcggaaac   720
gcctccttgg atacgtcatc gctgaaaacg aaagaagtgc gctgtaagta ttaccagcgc   780
acttcggcag cggcagcacc tcggcagcac ctcagcagca acatgcccag caagaagagt   840
ggaagaagcg gaccccaacc acataaaagg tgggtgttca cgctgaataa tccttccgaa   900
gacgagcgca agaaaatacg ggagctccca atctccctat ttgattattt tattgttggc   960
gaggaaggta atgaggaggg ccgaacaccg cacctacagg ggttcgctaa ttttgtgaag  1020
aagcaaactt ttaataaagt gaagtggtat tttggtgccc gctgccacat cgagaaagcg  1080
aaaggaacag atcagcagaa taagaatat  tgcagtaaag aaggcaactt actgatagaa   1140
tgtggagctc ctagatctca aggacaacgg agtgacctct ctactgctgt gagtaccttg  1200
ttggagagcg ggagtctggt gaccgttgca gagcagcacc ctgtaacgtt tgtcagaaat  1260
ttccgcgggc tggctgaact tttgaaagtg agcgggaaaa tgcagaagcg tgattggaag  1320
acgaatgtac acgtcattgt ggggccacct gggtgtggca aaagcaaatg gctgctaat   1380 tttgcagacc cggaaaccac atactggaaa ccacctagaa acaagtggtg ggatggttac  1440
catggtgaag aagtggttgt tattgatgac ttttatggct ggctgccgtg gatgatcta   1500 ctgagactct gtgatcgata tccttgact  gttgagacta aggtggaac tgtacctttt    1560 ttggcccgca gtattctgat taccagcaat cagaccccgt tggaatggta ctcctcaact  1620
gctgtcccag ctgtagaagc tctctatcgg aggattactt ccttggtatt ttggaagaat  1680
gctacagaac aatccacgga ggaaggggc  cagttcgtca ccctttcccc cccatgccct   1740
```

```
gaatttccat atgaaataaa ttactga                                             1767
```

<210> SEQ ID NO 67
<211> LENGTH: 233
<212> TYPE: PRT
<213> ORGANISM: Artificial Sequence
<220> FEATURE:
<223> OTHER INFORMATION: majority sequence based on PCV2 strains NMB,
    ISU-40895 and PCV2B-DIV-MUT
<220> FEATURE:
<221> NAME/KEY: MISC_FEATURE
<222> LOCATION: (59)..(59)
<223> OTHER INFORMATION: Xaa can be ALA, ARG, or LYS
<220> FEATURE:
<221> NAME/KEY: MISC_FEATURE
<222> LOCATION: (89)..(89)
<223> OTHER INFORMATION: Xaa can be ILE, ARG, or LEU
<220> FEATURE:
<221> NAME/KEY: MISC_FEATURE
<222> LOCATION: (190)..(190)
<223> OTHER INFORMATION: Xaa can be SER, ALA, or THR

<400> SEQUENCE: 67

Met Thr Tyr Pro Arg Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Xaa Thr Thr Val Arg Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Xaa Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Xaa Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Asn Pro
225                 230

What is claimed is:

1. A vaccine composition for protecting pigs against PCV2, including a highly virulent porcine circovirus type 2b (PCV2b) divergent strain, the composition comprising a PCV2b ORF2 polypeptide encoded by a PCV2b divergent strain having at least 95% sequence identity with SEQ ID NO: 66, wherein the ORF2 polypeptide comprises Leucine (L) at position 89, Threonine (T) at position 90, and Asparagine (N) at position 134, according to the numbering of SEQ ID NO: 1; and an oil-in-water emulsion adjuvant.

2. The composition of claim 1, wherein the composition is in the form of an inactivated, PCV2b divergent whole virus that comprises the PCV2b ORF2 polypeptide as its viral capsid.

3. The composition of claim 1, wherein the composition is in the form of an inactivated chimeric porcine circovirus type 1-type2 whole virus, wherein said chimeric porcine circovirus comprises an inactivated recombinant porcine circovirus type 1 that comprises the PCV2b ORF2 polypeptide in place of the ORF2 capsid of PCV1.

4. The composition of claim 1, wherein the composition is in the form of an isolated, recombinant PCV2b ORF2 polypeptide.

5. The composition of claim 4, wherein the composition further includes an expression vector.

6. The composition of claim 5, wherein the vector is baculovirus or parapoxvirus.

7. The composition of claim 5, wherein the vector is a live or inactivated vector.

8. The composition of claim 1, wherein the PCV2b ORF2 polypeptide further comprises at least one residue selected from the group consisting of: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215 according to the numbering of SEQ ID NO: 1.

9. The composition of claim 1, wherein the PCV2b ORF2 polypeptide further comprises a Lysine (K) at residue 59 and a Lysine (K) at residue 234 according to the numbering of SEQ ID NO: 1.

10. The composition of claim 9, wherein the PCV2b ORF2 polypeptide further comprises a Threonine (T) at residue 190, an Isoleucine (I) at residue 53, an Asparagine (N) at residue 68, an Arginine (R) or Glycine (G) at residue 169, and an Isoleucine (I) at residue 215 according to the numbering of SEQ ID NO: 1.

11. The composition of claim 1, wherein the PCV2 ORF2 polypeptide is represented by the amino acid sequence of SEQ ID NO: 1, or an immunogenic portion thereof corresponding to a truncated form of the ORF2 polypeptide.

12. The composition of claim 1, further comprising at least one additional porcine antigen.

13. The composition of claim 12, wherein the at least one additional antigen is protective against a disease in pigs caused by a microorganism.

14. The composition of claim 13, wherein the microorganism comprises a bacterium, virus, or protozoan.

15. The composition of claim 14, wherein the microorganism is selected from the group consisting of *Mycoplasma hyopneumoniae* (M. hyo), porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacilllus pleuropneumoniae*, *Bordetella bronchiseptica*, *Salmonella choleraesuis*, *Salmonella enteritidis*, *Erysipeiothrix rhusiopathiae*, *Mycoplama hyorhinis*, *Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

16. The composition of claim 1, wherein the oil-in-water emulsion adjuvant is based on squalane and comprises a block copolymer.

17. The composition of claim 1, wherein the composition further comprises a pharmaceutically acceptable carrier.

18. A method of immunizing a pig against PCV2, including a highly virulent PCV2b divergent strain, the method comprising administering to the pig the composition of claim 1.

19. The method of claim 18, wherein the composition is administered intranasally, intramuscularly, intradermally, transdermally, subcutaneously, or orally.

20. The method of claim 18, wherein the composition is administered in a single dose.

21. The method of claim 18, wherein the composition is administered as two doses.

22. The method of claim 18, wherein the composition is administered to pigs having maternally-derived antibodies against PCV2.

23. The method of claim 18, wherein the composition is administered to pigs at 3 weeks of age or older.

24. A kit comprising: a bottle comprising a vaccine composition for protecting pigs against PCV2, including a highly virulent porcine circovirus type 2b (PCV2b) divergent strain, the composition comprising a PCV2b ORF2 polypeptide encoded by a PCV2b divergent strain having at least 95% sequence identity with SEQ ID NO: 66, wherein the ORF2 polypeptide comprises Leucine (L) at position 89, Threonine (T) at position 90, and Asparagine (N) at position 134 according to the numbering of SEQ ID NO: 1, and an oil-in-water emulsion adjuvant.

25. The kit of claim 24, wherein the PCV2b divergent ORF2 polypeptide further comprises at least one residue selected from the group consisting of: a Lysine (K) at residue 59, a Lysine (K) at residue 234, a Threonine (T) at residue 190, an Isoleucine (I) at residue 53, an Asparagine (N) at residue 68, an Arginine (R) or Glycine (G) at residue 169, and an Isoleucine (I) at residue 215 according to the numbering of SEQ ID NO: 1.

26. The kit of claim 25, wherein the composition in the bottle is provided as a ready-to-use liquid composition.

27. The kit of claim 24, wherein the composition is provided in a lyophilized form.

28. The kit of claim 27, further comprising a diluent.

* * * * *